US007230125B1

(12) United States Patent
Rawal et al.

(10) Patent No.: US 7,230,125 B1
(45) Date of Patent: Jun. 12, 2007

(54) METHODS OF PERFORMING CYCLOADDITIONS, REACTION MIXTURES, AND METHODS OF PERFORMING ASYMMETRIC CATALYTIC REACTIONS

(75) Inventors: Viresh H. Rawal, Chicago, IL (US); Yong Huang, Pasadena, CA (US); Aditya K. Unni, Chicago, IL (US); Avinash N. Thadani, Chicago, IL (US)

(73) Assignee: The University of Chicago, Chicago, IL (US)

( * ) Notice: Subject to any disclaimer, the term of this patent is extended or adjusted under 35 U.S.C. 154(b) by 329 days.

(21) Appl. No.: 10/629,537

(22) Filed: Jul. 28, 2003

Related U.S. Application Data

(60) Provisional application No. 60/398,696, filed on Jul. 26, 2002.

(51) Int. Cl.
*C07D 315/00* (2006.01)
(52) U.S. Cl. ............... 549/416; 549/330; 549/273; 546/16
(58) Field of Classification Search ............... 549/273, 549/416, 330; 546/16
See application file for complete search history.

(56) References Cited

U.S. PATENT DOCUMENTS 6,130,340 A * 10/2000 Jacobsen et al. ............ 549/273

OTHER PUBLICATIONS

Xu, M.; Pu, L., "A New 1,1'-Binaphthyl-Based Catalyst for the Enantioselective Phenylacetylene Addition to Aromatic Aldehydes without Using a Titanium Complex", *Organic Letters*, 2002, vol. 4, No. 25, pp. 4555-4557.
Guay, V.; Brassard, P., "Reactions of Ketene Acetals 15[1]. Regiospecific Syntheses of Erythrolaccin and "7-Hydroxyerythrolaccin".", *Tetrahedron*, 1984, vol. 40, No. 24, pp. 5039-5045.
Schiess, P.; Erberle, M.; Huys-Francotte, M.; Wirz, J., "Thermal Addition Reactions to Benzocyclobutenones Studied by Flash Photolysis", *Tetrahedron Letters*, 1984, vol. 25, No. 21, pp. 2201-2204.
Midland, M. M.; Graham, R. S., "High Threo Diastereoselectivity via Europium(III)-Catalyzed Cyclocondensation of a Silyloxy Diene with α-Alkoxy Aldehydes. Synthesis of (−)-Pestalotin", *J. Am. Chem. Soc.*, 1984, vol. 106, No. 15, pp. 4294-4296.
Daniewski, W. M.; Kubak, E.; Jurczak, J.; "High-Pressure Approach to the Total Synthesis of (±)-Ambreinolide and (±)-8-Epiambreinolide", *J. Org. Chem.*, 1985, vol. 50, No. 21, pp. 3963-3965.
Rigby, J. H.; Wilson, J. A. Z., "A General Approach to the Synthesis of $C_8$-Oxygenated Guaianolides", *J. Org. Chem.*, 1987, vol. 52, No. 1, pp. 34-44.
Kozmin, S. A.; Janey, J. M.; Rawal, V. H., "1-Amino-3-siloxy-1,3-butadienes: Highly Reactive Dienes for the Diels-Alder Reaction", *J. Org. Chem.*, 1999, vol. 64, No. 9, pp. 3039-3052.

Huang, Y.; Rawal, V. H., "Hetero Diels-Alder Reactions of 1-Amino-3-siloxy-1,3-butadienes under Strictly Thermal Conditions", *Organic Letters*, 2000, vol. 2, No. 21, pp. 3321-3323.
Kozmin, S. A.; Green, M. T.; Rawal, V. H., "On the Reactivity of 1-Amino-3-siloxy-1,3-dienes: Kinetics Investigation and Theoretical Interpretation", *J. Org. Chem.*, 1999, vol. 64, No. 21, pp. 8045-8047.
Kozmin, S. A.; Rawal, V. H., "Chiral Amino Siloxy Dienes in the Diels-Alder Reaction: Applications to the Asymmetric Synthesis of 4-Substituted and 4,5-Disubstituted Cyclohexenones and the Total Synthesis of (−)-α-Elemene", *J. Am. Chem. Soc.*, 1999, vol. 121, No. 41, pp. 9562-9573.
Huang, Y.; Iwama, T.; Rawal, V. H., "Highly Enantioselective Diels-Alder Reactions of 1-Amino-3-siloxy-dienes Catalyzed by Cr(III)-Salen Complexes", *J. Am. Chem. Soc.*, 2000, vol. 122, No. 32, pp. 7843-7844.
Steiner, T., "Donor and acceptor strengths in C-H•••O hydrogen bonds quantified from crystallographic data of small solvent molecules", *New J. Chem*, 1998, pp. 1099-1103.
Kryachko, E. S.; Zeegers-Huyskens, T., "Theoretical Study of the CH•••O Interaction in Fluoromethanes·$H_2O$ and Chloromethanes·$H_2O$ Complexes", *J. Phys. Chem. A.*, 2001, Vol. 105, No. 29, pp. 7118-7125.
Breslow, R., "Hydrophobic Effects on Simple Organic Reactions in Water", *Accounts of Chemical Research*, 1991, vol. 24, No. 6, pp. 159-164.
Kelly, T. R.; Meghani, P.; Ekkundi, V. S., "Diels-Alder Reactions: Rate Acceleration Promoted By A Biphenylenediol", *Tetrahedron Letters*, 1990, vol. 31, No. 24, pp. 3381-3384.
Schmidt, R. R., "Hetero-Diels-Alder Reaction in Highly Functionalized Natural Product Synthesis", *Accounts of Chemical Research*, 1986, vol. 19, pp. 250-259.
Schuster, T.; Kurz, M.; Göbel, M. W., "Catalysis of a Diels-Alder Reaction by Amidinium Ions", *J. Org. Chem.*, 2000, vol. 65, No. 6, pp. 1697-1701.
Schreiner, P. R.; Wittkopp, A., "H-Bonding Additives Act Like Lewis Acid Cataysts", *Organic Letters*, 2002, vol. 4, No. 2, pp. 217-220.
Martin, T.W., Derewenda, Z. S., "The name is bond—H bond", *Nature Structural Biology*, 1999, vol. 6, No. 5, pp. 403-406.
Vachal, P.; Jacobsen, E. N., "Structure-Based Analysis and Optimization of a Highly Enantioselective Catalyst for the Strecker Reaction", *J. Am. Chem. Soc.*, 2002, vol. 124, No. 34, pp. 10012-10014.

(Continued)

*Primary Examiner*—Amelia A. Owens
(74) *Attorney, Agent, or Firm*—Brinks Hofer Gilson & Lione; Gregory H. Zayla

(57) ABSTRACT

Methods of performing cycloadditions are described that include (a) combining a first reactant and a second reactant in a hydrogen bonding solvent to form a reaction mixture; and (b) reacting the first reactant and the second reactant to form a cycloadduct. Methods of performing asymmetric catalytic reactions are also described that include (a) combining a first reactant, a second reactant, and a catalytic amount of a chiral hydrogen-bond donor in a solvent to form a reaction mixture; and (b) reacting the first reactant and the second reactant to form an enantiomeric excess of a reaction product. Reaction mixtures corresponding to these methods are also described.

39 Claims, 47 Drawing Sheets

OTHER PUBLICATIONS

Schuster, T.; Bauch, M.; Dürner, G.; Göbel, M. W., "Axially Chiral Amidinium Ions as Inducers of Enantioselectivity in Diels-Alder Reactions", *Organic Letters*, 2000, vol. 2, No. 2, pp. 179-181.

Jørgensen, K. A., "Catalytic Asymmetric Hetero-Diels-Alder Reactions of Carbonyl Compounds and Imines", *Angew. Chem. Int. Ed.*, 2000, vol. 39, pp. 3558-3588.

Prins, L. J.; Reinhoudt, D. N.; Timmerman, P., "Noncovalent Synthesis Using Hydrogen Bonding", *Angew. Chem. Int. Ed.*, 2001, vol. 40, pp. 2382-2426.

Huang, Y.; Rawal, V. H., "Hydrogen-Bond-Promoted Hetero-Diels-Alder Reactions of Unactivated Ketones", *J. Am. Chem. Soc.*, 2002, Vol. 124, No. 33, pp. 9662-9663.

Seebach, D.; Beck, A. K.; Heckel, A., "TADDOLs, Their Derivatives, and TADDOL Analogues: Versatile Chiral Auxiliaries", *Angew. Chem. Int. Ed.*, 2001, vol. 40, pp. 92-138.

Dalko, P. I.; Moisan, L., "Enantioselective Organocatalysts", *Angew. Chem. Int. Ed.*, 2001, vol. 40, pp. 3726-3748.

Bednarski, M.; Danishefsky, S., "Interactivity of Chiral Catalysts and Chiral Auxiliaries in the Cycloaddition of Activated Dienes with Aldehydes: A Synthesis of L-Glucose", *J. Am. Chem. Soc.*, 1986, vol. 108, No. 22, pp. 7060-7067.

Corey, E. J.; Cywin, C. L.; Roper, T. D., "Enantioselective Mukaiyama-Aldol and Aldol-Dihydropyrone Annulation Reactions Catalyzed by a Tryptophan-Derived Oxazaborolidine", *Tetrahedron Letters*, 1992, vol. 33, No. 46, pp. 6907-6910.

Wang, B.; Feng, X.; Huang, Y.; Liu, H.; Cui, X.; Jiang, Y., "A Highly Enantioselective Hetero-Diels-Alder Reaction of Aldehydes with Danishefshy's Diene Catalyzed by Chiral Titanium(IV) 5,5′,6,6′,7,7′,8,8′-Octahydro-1,1′-bi-2-naphthol Complexes", *J. Org. Chem.*, 2002, vol. 67, No. 7, pp. 2175-2182.

Long, J.; Hu, J.; Shen, X.; Ji, B.; Ding, K., "Discovery of Exceptionally Efficient Catalysts for Solvent-Free Enantioselective Hetero-Diels-Alder Reaction", *J. Am. Chem. Soc.*, 2002, vol. 124, No. 1, pp. 10-11.

Kezuka, S.; Mita, T.; Ohtsuki, N.; Ikeno, T.; Yamada, T., "Highly Active 3-Oxobutylideneaminatocobalt Complex Catalysts for an Enantioselective Hetero Diels-Alder Reaction", *Bull. Chem. Soc. Jpn.*, 2001, vol. 74, No. 7, pp. 1333-1342.

Hanamoto, T.; Furuno, H.; Sugimoto, Y.; Inanaga, J., "Asymmetric Hetero Diels-Alder Reaction Catalyzed by Chiral Ytterbium(III) Phosphate {Yb[(R)-(–)-BNP]$_3$}: Remarkable Ligand Effect on the Enantioselectivity", *Synlett*, 1997, pp. 79-80.

Schaus, S. E.; Brånalt, J.; Jacobsen, E. N., "Asymmetric Hetero-Diels-Alder Reactions Catalyzed by Chiral (Salen)Chromium(III) Complexes", *J. Org. Chem.*, 1998, vol. 63, No. 2, pp. 403-405.

Aikawa, K.; Irie, R.; Katsuki, T., "Asymmetric hetero Diels-Alder reaction using chiral cationic metallosalen complexes as catalysts", *Tetrahedron*, 2001, vol. 57, pp. 845-851.

Huang, Y.; Unni, A. K.; Thadani, A. N.; Rawal, V. H., "Hydrogen Bonding: Single Enantiomers from a chiral-alcohol catalyst", *Nature*, 2003, vol. 424, p. 146.

Pindur, U.; Lutz, G.; Otto, C., "Acceleration and Selectivity Enhancement of Diels-Alder Reactions by Special and Catalytic Methods", *Chem. Rev.*, 1993, vol. 93, No. 2, pp. 741-761.

Kumar, A., "Salt Effects on Diels-Alder Reaction Kinetics", *Chemical Reviews*, 2001, vol. 101, No. 1, pp. 1-19.

Tietze, L. F.; Kettschau, G., "Hetero Diels-Alder Reactions in Organic Chemistry", *Topics in Current Chemistry*, 1997, vol. 189, pp. 1-120.

Bednarski, M. D.; Lyssikatos, J. P., "Reactions of Activated Dienes with Aldehydes", *Comprehensive Organic Synthesis*, 1991, vol. 2, pp. 661-706.

Beck, A. K.; Bastani, B.; Plattner, D. A.; Petter, W.; Seebach, D.; Braunschweiger, H.; Gysi, P.; La Vecchia, L., "Grossansätze zur Herstellung von α,α,α$^1$,α$^1$-Tetraaryl-1,3-dioxolan-4,5-dimethanolen (TADDOLe): Nützliche Hilfsstoffe für die EPC-Synthese und ihre Struktur im Festkörper", *Chimia*, 1991, vol. 45, pp. 238-244.

Lubineau, A.; Augé, J., "Water as Solvent in Organic Synthesis", *Topics in Current Chemistry*, 1999, vol. 206, pp. 1-39.

Brouard, C.; Pornet, J.; Miginiac, L., "A Convenient Synthesis of 3,4-Bis(Trimethylsilylmethyl)-5,6-Dihydro-2H-Pyrans Through a Catalyzed Hetero Diels-Alder Reaction", *Synthetic Communications*, 1994, vol. 24, No. 21, pp. 3047-3053.

Chino, K.; Takata, T.; Endo, T., "A Novel Synthesis of 1-Isochromanols Via Hetero Diels-Alder Reaction of Carbonyl Compounds with 1-Trimethylsilyloxy-Benzocyclobutene as a Precursor of α-OXY-o-Quinodimethane Under Mild Condition", *Synthetic Communications*, 1996, vol. 26, No. 11, pp. 2145-2154.

Danishefsky, S. J.; DeNinno, M. P., "Totally Synthetic Routes to the Higher Monosaccharides", *Angew. Chem. Int. Ed. Engl.*, 1987, vol. 26, pp. 15-23.

Kametani, T.; Hibino, S., "The Synthesis of Natural Heterocyclic Products by Hetero Diels-Alder Cycloaddition Reactions", *Advances in Heterocyclic Chemistry*, 1987, vol. 42, pp. 245-333.

Grieco, P. A., "Organic Chemistry in Unconventional Solvents", *Aldrichimica Acta*, 1991, vol. 24, No. 3, pp. 59-66.

\* cited by examiner

FIG. 8
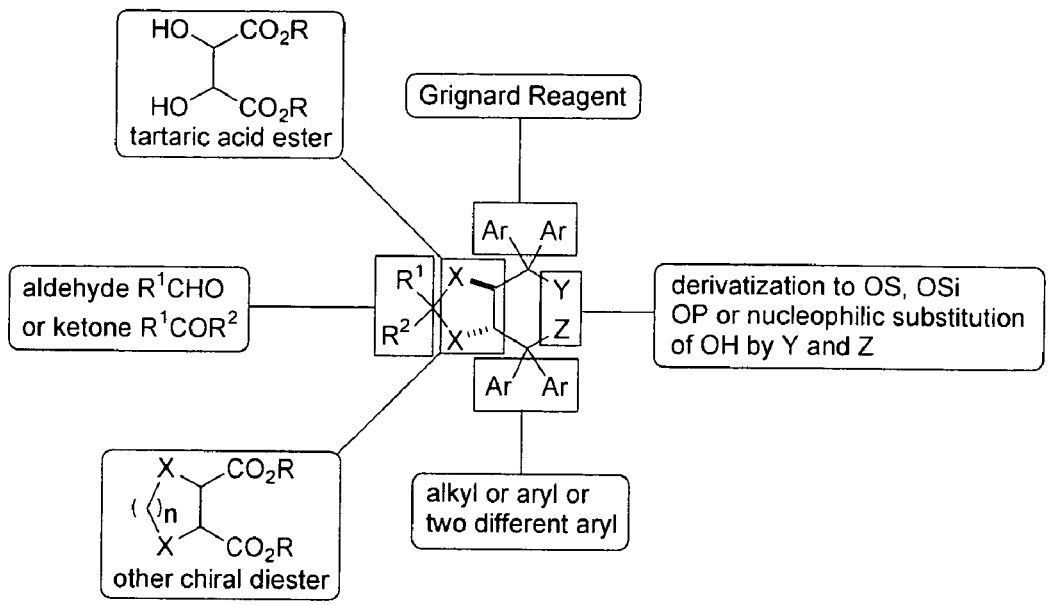
FIG. 9
(a) (b)
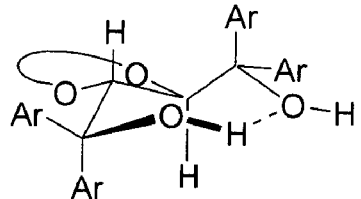 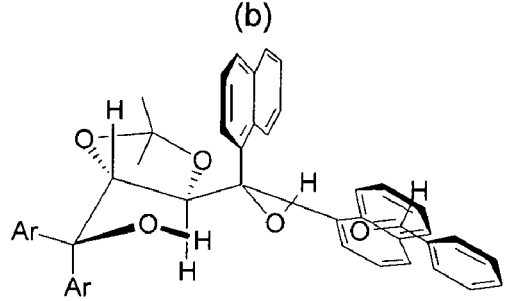
FIG. 10
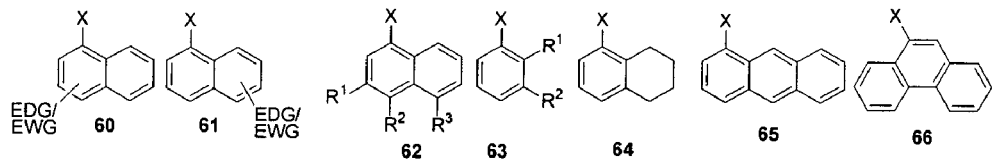
FIG. 11
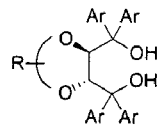

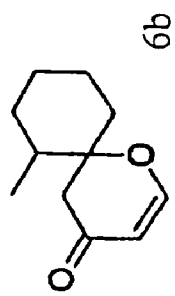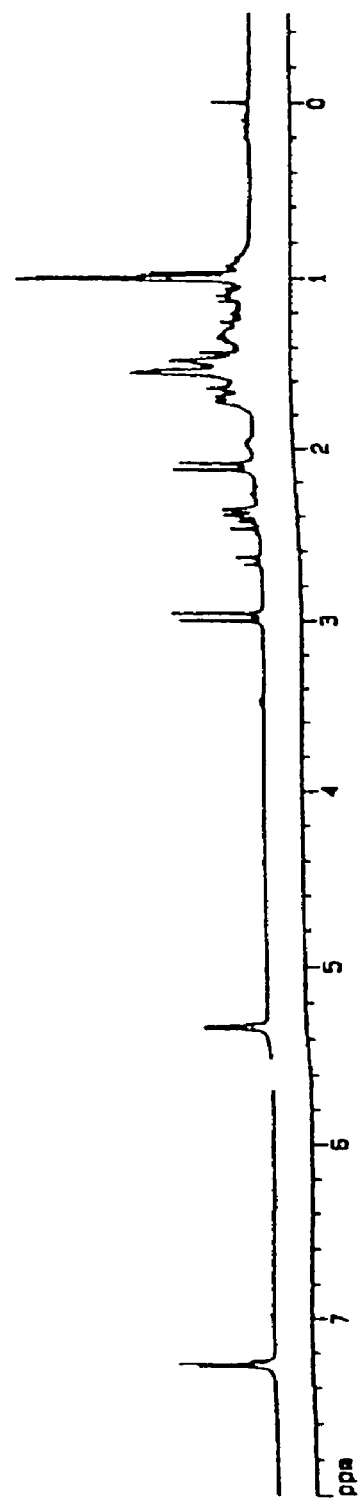
FIGURE 14

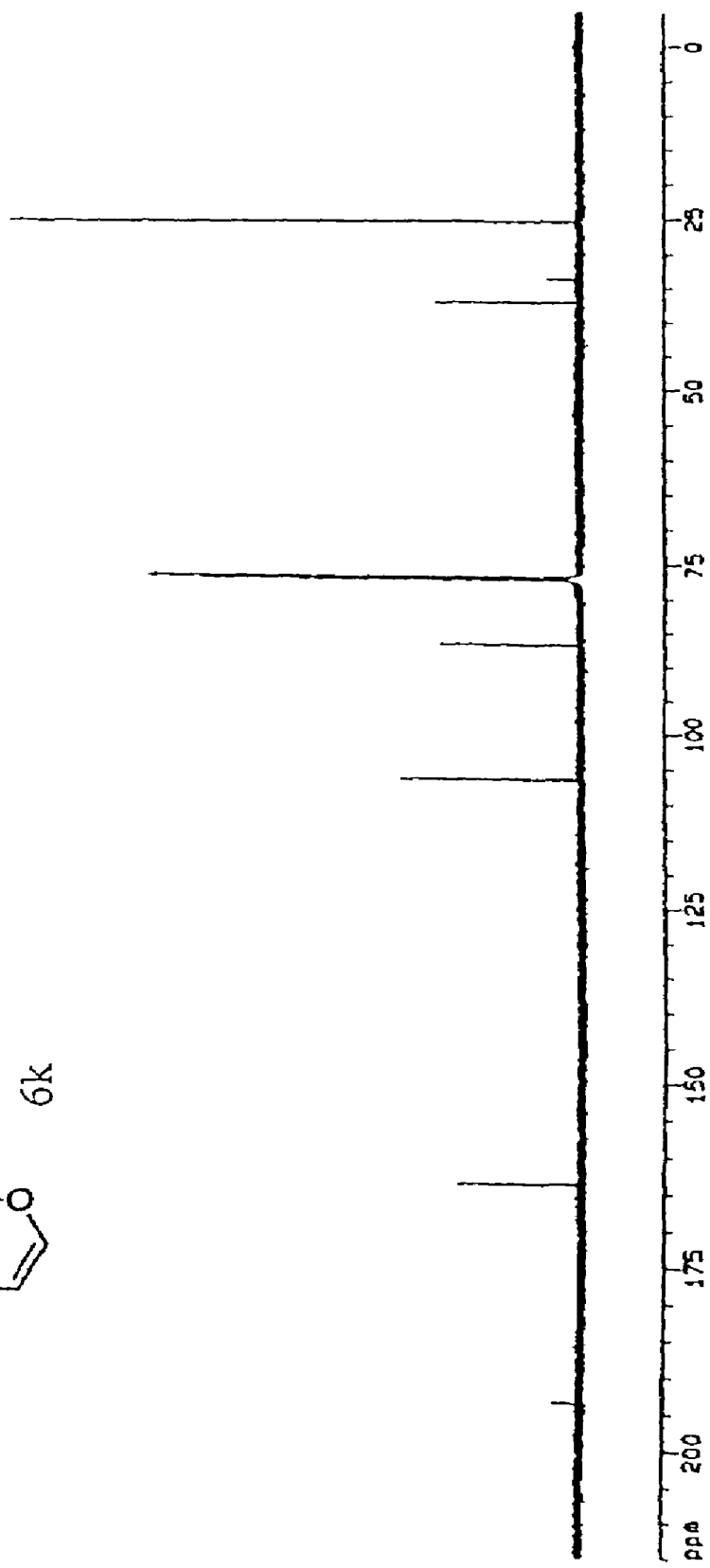
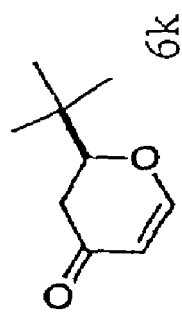
FIGURE 35

Sample: AKU.II.175A
Chiracel OD-H, 25cm
10% i-PrOH/Hexane, 0.9 mL/min

Method: 0.9mL/Min.
Sampling Int: 0.1 Seconds

Data:

4a

[Chiralcel OD-H, hexane:*i*-propanol = 9:1, 0.9 mL/min]

Analysis: Channel A

| Peak No. | Time | Type | Height(µV) | Area(µV-sec) | Area% |
|---|---|---|---|---|---|
| 1 | 3.576 | N1 | 9215 | 100994 | 0.504 |
| 2 | 3.886 | N2 | 26062 | 363490 | 1.813 |
| 3 | 4.370 | N3 | 2613 | 30416 | 0.151 |
|   | 4.858 | N | 832 | 5627 | 0.028 |
| 4 | 5.456 | N | 2006 | 26731 | 0.133 |
| 5 | 6.615 | N | 1779 | 17149 | 0.085 |
| 6 | 12.885 | N | 956520 | 19340950 | 96.519 |
| 7 | 14.998 | N | 6812 | 153023 | 0.763 |
| Total Area |  |  |  | 20038380 | 99.996 |

Sample: AKU.II.145A
Chiracel OD-H, 25cm
10% i-PrOH/Hexane, 0.9 mL/min

Method: 0.9mL/Min.
Sampling Int: 0.1 Seconds
Data:

racemic
[Chiralcel OD-H, hexane:i-propanol = 9:1, 0.9 mL/min]

Analysis: Channel A

| Peak No. | Time | Type | Height(μV) | Area(μV-sec) | Area% |
|---|---|---|---|---|---|
| | 3.503 | N1 | 562 | 2651 | 0.006 |
| 1 | 3.826 | N2 | 1893 | 15956 | 0.039 |
| | 4.046 | N3 | 971 | 5725 | 0.014 |
| | 5.006 | N1 | 718 | 2973 | 0.007 |
| | 5.241 | N2 | 233 | 1869 | 0.004 |
| 2 | 7.813 | N1 | 2964 | 30947 | 0.076 |
| 3 | 8.115 | N2 | 1962 | 20583 | 0.050 |
| 4 | 11.876 | N1 | 3520 | 61696 | 0.152 |
| 5 | 12.655 | Err! | 1035167 | 20146444 | 49.752 |
| 6 | 14.731 | N | 883568 | 20204608 | 49.895 |
| Total Area | | | | 40493452 | 99.995 |

Sample: AKU.II.227A
Chiracel OD-H, 25cm
10% i-PrOH/Hexane, 0.5 mL/min

Method: 0.5mL/Min.
Sampling Int: 0.1 Seconds
Data:

[Chiralcel OD-H, hexane:*i*-propanol = 9:1, 0.5 mL/min]
(tentative assignment based on 4a)

0.0                                                              60.0
Analysis: Channel A

| Peak No. | Time   | Type | Height(μV) | Area(μV-sec) | Area%  |
|----------|--------|------|------------|--------------|--------|
| 1        | 20.176 | E2   | 177        | 2916         | 0.029  |
| 2        | 24.183 | E1   | 175        | 918          | 0.009  |
| 3        | 24.811 | E2   | 90         | 1073         | 0.010  |
| 4        | 28.543 | E2   | 223631     | 9478845      | 97.085 |
| 5        | 32.026 | N    | 6108       | 279641       | 2.864  |
| Total Area |      |      |            | 9763393      | 99.997 |

Sample: AKU.II.145B
Chiracel OD-H, 25cm
10% i-PrOH/Hexane, 0. 5 mL/min

Method: 0.5mL/Min.
Sampling Int: 0.1 Seconds

Data:

racemic
Chiralcel OD-H, hexane:*i*-propanol = 9:1, 0.5 mL/min]

Analysis: Channel A

| Peak No. | Time | Type | Height(μV) | Area(μV-sec) | Area% |
|---|---|---|---|---|---|
| 1 | 12.905 | N | 1970 | 30188 | 0.026 |
| 2 | 31.618 | Err! | 1197506 | 56719898 | 49.888 |
| 3 | 33.961 | Err! | 1110108 | 56943876 | 50.085 |
| Total Area | | | | 113693962 | 99.999 |

FIG. 40

Sample:
pyran-3-bromophenyl
OD-H
20% i-PrOH/Hexane, 1.0 ML/min

Processing File:
Method: general condition-30min
Sampling Int: 0.1 Seconds
Data:

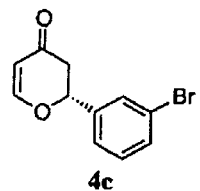

4c
crude
[Chiralcel OD-H, hexane:*i*-propanol = 4:1, 1.0 mL/min]
(tentative assignment based on 4a)
note: ent-2 was used as the catalyst

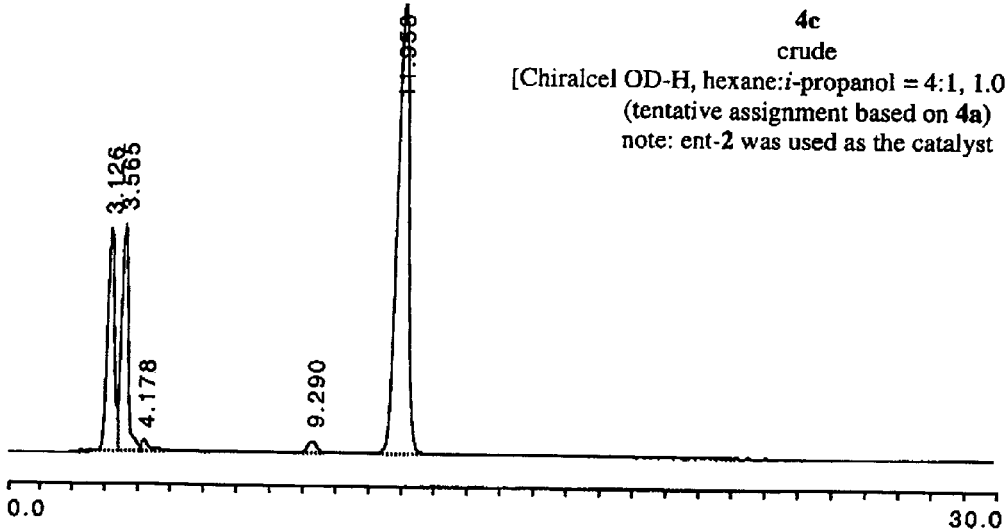

0.0                                                                 30.0

Analysis: Channel A

| Peak No. | Time | Type | Height(µV) | Area(µV-sec) | Area% |
|---|---|---|---|---|---|
|   | 2.245 | Errl | 1147 | 633 | 0.005 |
|   | 2.645 | Errl | 543 | 2336 | 0.020 |
| 1 | 3.126 | N1 | 174081 | 1923918 | 16.718 |
| 2 | 3.565 | N2 | 176533 | 2034916 | 17.683 |
| 3 | 4.178 | Errl | 7530 | 88623 | 0.770 |
|   | 4.555 | Errl | 1062 | 7197 | 0.062 |
|   | 6.066 | Errl | 401 | 1315 | 0.011 |
|   | 8.678 | Errl | 385 | 135 | 0.001 |
|   | 8.776 | Errl | 243 | 191 | 0.001 |
| 4 | 9.290 | Errl | 8197 | 130505 | 1.134 |

| Peak No. | Time | Type | Height(µV) | Area(µV-sec) | Area% |
|---|---|---|---|---|---|
| 5 | 11.958 | N | 350239 | 7317384 | 63.586 |
|   | 17.498 | Errl | 257 | 551 | 0.004 |
| Total Area |   |   |   | 11507704 | 99.995 |

Sample:
pyran-3-bromophenyl
OD-H
20% i-PrOH/Hexane, 1.0 ML/min

Processing File:
Method: general condition-30min
Sampling Int: 0.1 Seconds
Data:

racemic
[Chiralcel OD-H, hexane:*i*-propanol = 4:1, 1.0 mL/min]
crude

Analysis: Channel A

| Peak No. | Time | Type | Height(μV) | Area(μV-sec) | Area% |
|---|---|---|---|---|---|
| 1 | 3.580 | N1 | 929950 | 18672350 | 15.123 |
| 2 | 3.918 | Errl | 1578446 | 44994432 | 36.443 |
| 3 | 4.301 | Errl | 1251011 | 26245272 | 21.257 |
| 4 | 5.023 | N4 | 221661 | 5347249 | 4.330 |
| 5 | 6.036 | N5 | 40524 | 835084 | 0.676 |
| 6 | 6.573 | Errl | 18597 | 557508 | 0.451 |
| 7 | 7.380 | N7 | 40756 | 792924 | 0.642 |
| 8 | 8.225 | Errl | 2766 | 48066 | 0.038 |
| 9 | 9.346 | N | 790975 | 13368844 | 10.828 |
| 10 | 12.061 | N | 602050 | 12510882 | 10.133 |

Data: AT.4-CF3.20mol%.L.-78.48h.0.9

Method: 0.9mL/Min.
Sampling Int: 0.1 Seconds
Data:

[Chiralcel OD-H, hexane:*i*-propanol = 10:1, 0.9 mL/min]
(tentative assignment based on 4a)

Analysis: Channel A

| Peak No. | Time | Type | Height(µV) | Area(µV-sec) | Area% |
|---|---|---|---|---|---|
| 1 | 3.421 | N | 16523 | 279041 | 5.146 |
| 2 | 9.315 | N | 1831 | 23937 | 0.441 |
| 3 | 12.208 | N | 254842 | 4991673 | 92.064 |
| 4 | 16.100 | N | 5165 | 127294 | 2.347 |
| Total Area | | | | 5421945 | 99.998 |

FIG. 43
Data: AKU.II.145C 4-F3C rac
Sample: AKU.II.145C
Chiracel OD-H, 25cm
10% i-PrOH/Hexane, 0.9 mL/min
Method: 0.9mL/Min.
Sampling Int: 0.1 Seconds
Data:
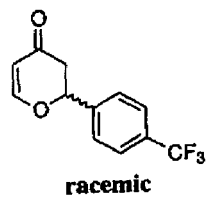
racemic
[Chiralcel OD-H, hexane:$i$-propanol = 9:1, 0.9 mL/min]
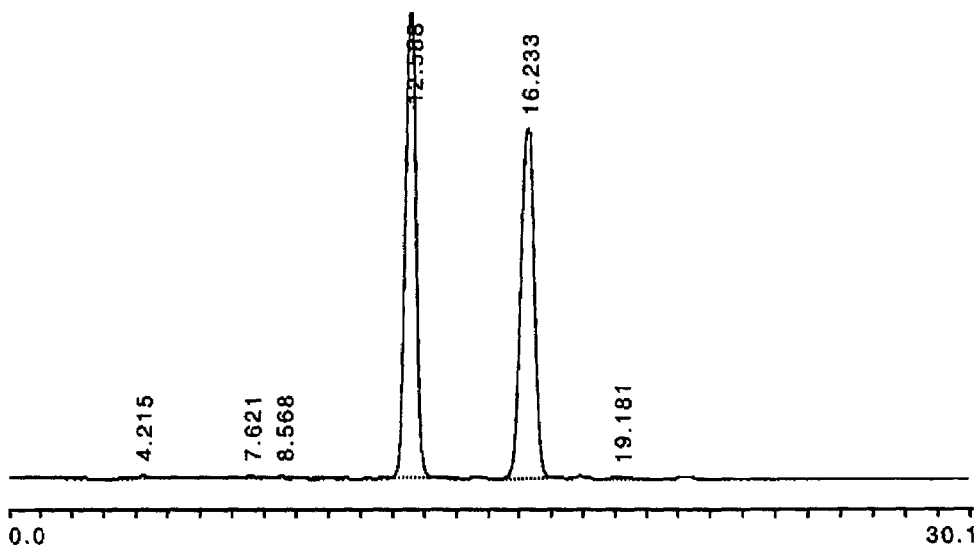
Analysis: Channel A
| Peak No. | Time | Type | Height(μV) | Area(μV-sec) | Area% |
|---|---|---|---|---|---|
| | 3.901 | N | 452 | 2495 | 0.010 |
| 1 | 4.215 | N1 | 2600 | 20244 | 0.088 |
| | 4.436 | N2 | 1156 | 8533 | 0.037 |
| | 5.408 | N | 921 | 6206 | 0.027 |
| 2 | 7.621 | N | 3893 | 40499 | 0.177 |
| 3 | 8.566 | N | 2653 | 25293 | 0.110 |
| 4 | 12.588 | N | 585042 | 11355290 | 49.815 |
| 5 | 16.233 | N | 440367 | 11268832 | 49.436 |
| 6 | 19.181 | N | 2648 | 67138 | 0.294 |
| | 28.736 | N | 159 | 191 | 0.000 |
| Total Area | | | | 22794721 | 99.994 |

Data: AT.1-naph.L.-78.48h(5%,1.4mL)

Sample: AT
1-naphthaldehyde, -78C, 48 h
OD-H, 5% iPrOH/hexanes, 1.4 mL/min

Processing File: aku1
Method: 1.4mL/Min.
Sampling Int: 0.1 Seconds

Data:

[Chiralcel OD-H, hexane:$i$-propanol = 19:1, 1.4 mL/min]
(tentative assignment based on 4a)

Analysis: Channel A

| Peak No. | Time | Type | Height(μV) | Area(μV-sec) | Area% |
|---|---|---|---|---|---|
| 1 | 26.160 | N | 29209 | 1383795 | 1.510 |
| 2 | 30.245 | Errl | 1140658 | 89644942 | 97.850 |
| 3 | 37.280 | N | 8712 | 585517 | 0.639 |
| Total Area | | | | 91614254 | 99.999 |

Sample: AKU.II.145G
Chiracel OD-H, 25cm
5% i-PrOH/Hexane, 1.4 mL/min

Method: 1.4mL/Min.
Sampling Int: 0.1 Seconds
Data:

racemic
[Chiralcel OD-H, hexane:*i*-propanol = 19:1, 1.4 mL/min]

Analysis: Channel A

| Peak No. | Time | Type | Height(μV) | Area(μV-sec) | Area% |
|---|---|---|---|---|---|
|  | 2.501 | N1 | 1416 | 5660 | 0.007 |
| 1 | 2.680 | N2 | 2174 | 11129 | 0.015 |
|  | 2.873 | N3 | 958 | 4 | 0.000 |
|  | 3.246 | N4 | 2289 | 3206 | 0.004 |
|  | 3.423 | N5 | 126 | 125 | 0.000 |
|  | 3.905 | N | 1121 | 9160 | 0.012 |
|  | 4.445 | N | 264 | 1584 | 0.002 |
| 2 | 5.056 | N | 5253 | 48998 | 0.068 |
|  | 6.221 | N | 1103 | 6385 | 0.008 |
| 3 | 7.725 | N | 1247 | 16261 | 0.022 |
| 4 | 10.313 | N | 6814 | 115950 | 0.162 |
| 5 | 12.068 | N | 6028 | 116445 | 0.162 |
| 6 | 30.988 | N1 | 525795 | 35549454 | 49.694 |
| 7 | 34.260 | N2 | 463757 | 35651328 | 49.837 |
| Total Area |  |  |  | 71535689 | 99.993 |

Data: AKU.II.222A-2Naphthyl

Sample:

Method: 1.0ml/Min
Sampling Int: 0.1 Seconds

Data:

[Chiralcel OD-H, hexane:*i*-propanol = 9:1, 1.0 mL/min]
(tentative assignment based on 4a)

0.0                                                        60.0

Analysis: Channel A

| Peak No. | Time | Type | Height(μV) | Area(μV-sec) | Area% |
|---|---|---|---|---|---|
|  | 3.195 | N | 562 | 2743 | 0.003 |
| 1 | 3.555 | N | 4237 | 32922 | 0.045 |
| 2 | 5.150 | N | 2066 | 31910 | 0.043 |
| 3 | 6.508 | N | 1790 | 15877 | 0.021 |
| 4 | 11.273 | N | 6316 | 120143 | 0.165 |
| 5 | 24.163 | Err! | 1601505 | 70209318 | 96.655 |
| 6 | 39.588 | N | 32426 | 2226042 | 3.064 |
| Total Area |  |  |  | 72638955 | 99.996 |

Data: AKU.II.145H 2-nap rac

Sample: AKU.II.145H
Chiracel OD-H, 25cm
10% i-PrOH/Hexane, 1.0 mL/min

Method: 1.0ml/Min
Sampling Int: 0.1 Seconds
Data:

racemic
[Chiralcel OD-H, hexane:*i*-propanol = 9:1, 1.0 mL/min]

Analysis: Channel A

| Peak No. | Time | Type | Height(μV) | Area(μV-sec) | Area% |
|---|---|---|---|---|---|
|  | 3.175 | N1 | 734 | 4123 | 0.008 |
| 1 | 3.451 | N2 | 2334 | 19682 | 0.039 |
| 2 | 3.823 | N3 | 1164 | 11387 | 0.022 |
|  | 4.556 | N1 | 983 | 5966 | 0.011 |
|  | 4.906 | N2 | 586 | 3850 | 0.007 |
|  | 5.160 | N3 | 1336 | 7364 | 0.014 |
| 3 | 6.313 | N1 | 123201 | 1137325 | 2.255 |
| 4 | 6.961 | N2 | 4382 | 89106 | 0.176 |
| 5 | 7.406 | N3 | 2798 | 32542 | 0.064 |
| 6 | 10.105 | N1 | 5044 | 82768 | 0.164 |
| 7 | 10.500 | N2 | 5499 | 99853 | 0.198 |
| 8 | 23.148 | N | 580150 | 24297556 | 48.180 |
| 9 | 28.153 | N | 8242 | 410122 | 0.813 |
| 10 | 36.568 | N | 361504 | 24228328 | 48.043 |
| Total Area |  |  |  | 50429972 | 99.994 |

Data: AKU.II.230D-furfural

Sample: AKU.II.230D
Chiracel OD-H, 25cm
10% i-PrOH/Hexane, 0.5 mL/min

Method: 0.5mL/Min.
Sampling Int: 0.1 Seconds
Data:

[Chiralcel OD-H, hexane:*i*-propanol = 9:1, 0.5 mL/min]

0.0                  51.2

Analysis: Channel A

| Peak No. | Time | Type | Height(μV) | Area(μV-sec) | Area% |
|---|---|---|---|---|---|
| 1 | 6.411 | N | 1714 | 25728 | 0.104 |
| 2 | 7.098 | N | 13543 | 191717 | 0.781 |
| 3 | 9.935 | N | 4187 | 130271 | 0.531 |
| 4 | 22.700 | N1 | 29171 | 931259 | 3.796 |
| 5 | 24.241 | N2 | 651282 | 23248690 | 94.785 |
| Total Area | | | | 24527665 | 99.997 |

Data: AKU.II.192C-racfufural

Sample: AKU.II.192C
Chiracel OD-H, 25cm
10% i-PrOH/Hexane, 0.5 mL/min

Method: 0.5mL/Min.
Sampling Int: 0.1 Seconds
Data:

racemic
[Chiralcel OD-H, hexane:*i*-propanol = 9:1, 0.5 mL/min]

Analysis: Channel A

| Peak No. | Time | Type | Height(μV) | Area(μV-sec) | Area% |
|---|---|---|---|---|---|
| 1 | 11.193 | N1 | 1918 | 30005 | 0.116 |
| 2 | 11.505 | N2 | 2075 | 33399 | 0.129 |
| 3 | 12.016 | N3 | 1705 | 28762 | 0.111 |
| 4 | 20.595 | N1 | 6701 | 124528 | 0.484 |
| 5 | 20.973 | N2 | 9347 | 317259 | 1.233 |
| 6 | 24.536 | N | 347076 | 12620834 | 49.085 |
| 7 | 26.988 | N | 314549 | 12557414 | 48.838 |
| Total Area | | | | 25712201 | 99.996 |

Data: AT.cyclohexyl.20mol%.L.-40.24h

Method: 0.2ml/Min
Sampling Int: 0.1 Seconds
Data:

4h
crude
[Chiralcel OD-H, hexane:i-propanol = 10:1, 0.2 mL/min]

| Peak No. | Time | Type | Height(µV) | Area(µV-sec) | Area% |
|---|---|---|---|---|---|
| 1 | 17.546 | N | 5980 | 174728 | 0.346 |
| 2 | 26.008 | N | 230323 | 13633398 | 27.041 |
| 3 | 31.078 | N | 785682 | 34237770 | 67.909 |
| 4 | 33.510 | N | 52307 | 2370768 | 4.702 |
| Total Area | | | | 50416664 | 99.998 |

Analysis: Channel A

Data: AKU.II.145M cyclohex rac

Sample:

Method: 0.3ml/Min
Sampling Int: 0.1 Seconds
Data:

racemic
[Chiralcel OD-H, hexane:*i*-propanol = 9:1, 0.3 mL/min]

0.0                           35.9

Analysis: Channel A

| Peak No. | Time | Type | Height(μV) | Area(μV-sec) | Area% |
|---|---|---|---|---|---|
|  | 14.186 | N | 338 | 1570 | 0.001 |
| 1 | 26.388 | Err! | 1753734 | 63525716 | 50.011 |
| 2 | 29.236 | Err! | 1574118 | 63493906 | 49.986 |
| Total Area |  |  |  | 127021192 | 99.998 |

Data: AKU.II.228A-propyl

Sample: AKU.II.228A
Chiracel OD-H, 25cm
1% i-PrOH/Hexane, 0.5 mL/min

Method: 0.1ml/Min
Sampling Int: 0.1 Seconds

Data:

[Chiralcel OD-H, hexane:*i*-propanol = 99:1, 0.5 mL/min]

0.0                        45.1

Analysis: Channel A

| Peak No. | Time | Type | Height(μV) | Area(μV-sec) | Area% |
|---|---|---|---|---|---|
| 1 | 6.233 | N1 | 74384 | 16438908 | 63.336 |
| 2 | 10.205 | N2 | 20930 | 1335791 | 5.146 |
| 3 | 23.515 | N | 231589 | 7483275 | 28.831 |
| 4 | 26.505 | N | 19769 | 696990 | 2.685 |
| Total Area | | | | 25954964 | 99.998 |

Data: AKU.II.224B-racpropyl

Sample: AKU.II.224B
Chiracel OD-H, 25cm
1% i-PrOH/Hexane, 0.5 mL/min

Method: 0.5mL/Min.
Sampling Int: 0.1 Seconds

Data:

racemic
[Chiralcel OD-H, hexane:i-propanol = 99:1, 0.5 mL/min]

Analysis: Channel A

| Peak No. | Time | Type | Height(µV) | Area(µV-sec) | Area% |
|---|---|---|---|---|---|
|  | 4.206 | N1 | 84 | 58 | 0.000 |
|  | 4.663 | N2 | 731 | 6970 | 0.017 |
| 1 | 6.548 | N3 | 15822 | 1110879 | 2.743 |
| 2 | 8.590 | N | 1569 | 15858 | 0.039 |
| 3 | 10.055 | N1 | 18436 | 897070 | 2.215 |
| 4 | 11.036 | N2 | 1532 | 36228 | 0.089 |
| 5 | 27.716 | N | 482954 | 19209732 | 47.436 |
| 6 | 31.815 | N | 421016 | 19218838 | 47.459 |
| Total Area |  |  |  | 40495633 | 99.998 |

Sample:
    pyran-styryl
    OD-H
    20% i-PrOH/Hexane, 1.0    ML/min

Method: general condition
Sampling Int: 0.1 Seconds

Data:

4j
crude
[Chiralcel OD-H, hexane:i-propanol = 4:1, 1.0 mL/min]
note: ent-2 was used as the catalyst Analysis: Channel A

| Peak No. | Time | Type | Height(µV) | Area(µV-sec) | Area% |
|---|---|---|---|---|---|
| | 2.821 | N1 | 2189 | 880 | 0.002 |
| 1 | 3.126 | N2 | 224396 | 2978829 | 6.902 |
| 2 | 3.571 | N3 | 306241 | 4112288 | 9.529 |
| 3 | 3.885 | N4 | 242989 | 5920349 | 13.719 |
| 4 | 4.271 | N5 | 184504 | 3709344 | 8.595 |
| 5 | 5.018 | N6 | 29215 | 642371 | 1.488 |
| 6 | 6.170 | N7 | 8060 | 159135 | 0.368 |
| 7 | 7.230 | N | 2209 | 22532 | 0.052 |
| 8 | 8.965 | N1 | 4560 | 71179 | 0.164 |
| 9 | 9.486 | N2 | 4266 | 75218 | 0.174 |
| 10 | 11.926 | N1 | 10308 | 204240 | 0.473 |
| 11 | 12.790 | N2 | 29826 | 673380 | 1.560 |
| 12 | 24.488 | N | 554249 | 24583814 | 56.967 |
| | 37.145 | Errl | 423 | 642 | 0.001 |
| Total Area | | | | 43154201 | 99.994 |

FIG. 55
Sample:
pyran-cinnamyl
OD-H
20% i-PrOH/Hexane, 1.0 mL/min
Method: general condition-30min
Sampling Int: 0.1 Seconds
Data:
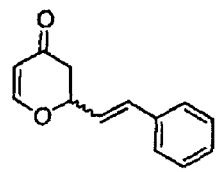
racemic
[Chiralcel OD-H, hexane:*i*-propanol = 4:1, 1.0 mL/min]
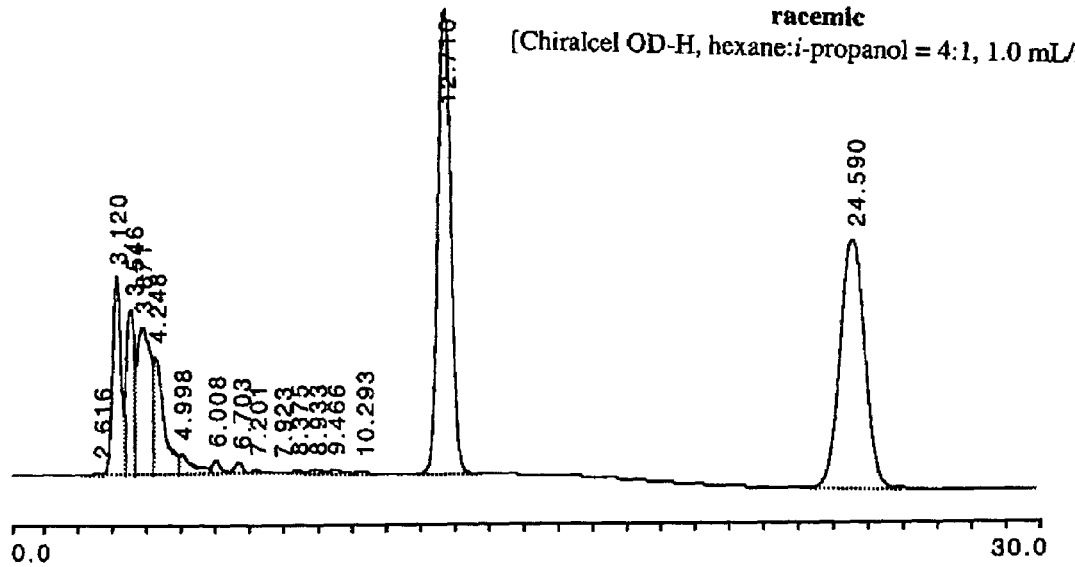
Analysis: Channel A
| Peak No. | Time | Type | Height(µV) | Area(µV-sec) | Area% |
|---|---|---|---|---|---|
| 11 | 8.375 | N2 | 6633 | 106844 | 0.115 |
| 12 | 8.933 | N3 | 8896 | 160544 | 0.172 |
| 13 | 9.466 | N4 | 7911 | 150553 | 0.162 |
| 14 | 10.293 | N | 3046 | 47285 | 0.050 |
| 15 | 12.710 | Err! | 1253481 | 28325212 | 30.501 |
| 16 | 24.590 | N | 671365 | 30885282 | 33.258 |
| Total Area | | | | 92865604 | 99.993 |

METHODS OF PERFORMING CYCLOADDITIONS, REACTION MIXTURES, AND METHODS OF PERFORMING ASYMMETRIC CATALYTIC REACTIONS

RELATED APPLICATIONS

This application claims the benefit of priority under 35 U.S.C. § 119(e) to U.S. provisional patent application Ser. No. 60/398,696, filed Jul. 26, 2002, the entire contents of which are incorporated herein by reference, except that in the event of any inconsistent disclosure or definition from the present application, the disclosure or definition herein shall be deemed to prevail.

FEDERALLY SPONSORED RESEARCH OR DEVELOPMENT

This application was funded in part under National Institutes of Health grant NIH R01-GM-55998. The U.S. Government may have rights in this invention.

FIELD OF THE INVENTION

The present invention relates generally to enantioselective catalysis and to cycloaddition reactions.

BACKGROUND

The [4+2] cycloaddition reaction between dienes and compounds containing a carbonyl group provides one of the most direct methods available for the synthesis of six-membered oxygen-containing heterocycles.

The hetero Diels-Alder (HDA) reaction has been studied extensively as a potential route for the preparation of oxygen-containing heterocycles, a class of biologically important molecules. Notwithstanding, the scope of the HDA reaction remains extremely limited. Nearly all such known cycloadditions have been reported using aldehydes and, even then, require highly specialized reaction conditions, such as high temperatures, high pressures, or Lewis acid catalysis.

For steric and electronic reasons, the ketone group is a substantially less reactive heterodienophile as compared to the aldehyde group. As a result, there have been extremely few reports of successful HDA reactions using simple ketones. Moreover, the use of ketones in these types of reactions is far from having general applicability. Accordingly, the development of a HDA reaction that is suitable for use with heterodienophiles such as ketones would be extremely advantageous.

Conventional methods for catalyzing asymmetric Diels-Alder reactions typically use metals and Lewis acids, which are often undesirable from the point of view of cost as well as safety (e.g., the presence of trace amounts of residual metals in the Diels-Alder cycloadduct may limit the pharmaceutical use of that compound due to strict federal regulations). Accordingly, the development of metal-free asymmetric variants of the Diels-Alder and HDA reaction would be highly desirable.

SUMMARY

The scope of the present invention is defined solely by the appended claims, and is not affected to any degree by the statements within this summary.

By way of introduction, a method of performing a cycloaddition reaction embodying features of the present invention includes: (a) combining a first reactant and a second reactant in a hydrogen bonding solvent to form a reaction mixture; and (b) reacting the first reactant and the second reactant to form a cycloadduct.

A first reaction mixture embodying features of the present invention includes: (a) a diene; (b) a dienophile; and (c) a hydrogen bonding solvent.

A method of performing an asymmetric catalytic reaction embodying features of the present invention includes: (a) combining a first reactant, a second reactant, and a catalytic amount of a chiral hydrogen-bond donor in a solvent to form a reaction mixture; and (b) reacting the first reactant and the second reactant to form an enantiomeric excess of a reaction product.

A first reaction mixture embodying features of the present invention includes: (a) a first reactant selected from the group consisting of diene and an alkyne; (b) a second reactant selected from the group consisting of a dienophile and an aldehyde, wherein the second reactant is complementary in reactivity to the first reactant; (c) a solvent; and (d) a catalytic amount of a chiral hydrogen-bond donor.

An improvement embodying features of the present invention to a method of performing a hetero-Diels-Alder reaction includes reacting a diene with a heterodienophile in a hydrogen bonding solvent selected from the group consisting of chloroform, t-butanol, i-propanol, 2-butanol, and combinations thereof.

BRIEF DESCRIPTION OF THE DRAWINGS

FIG. 8 shows components for the preparation of TADDOLs and their analogues.

FIG. 9 shows the staggered, $C_2$-symmetric conformation of the TADDOL skeleton.

FIG. 10 shows a series of 1-halo-naphthyl derivatives embodying features of the present invention.

FIG. 11 shows TADDOL structure with a generic acetonide in accordance with the present invention.

FIG. 12 shows a $^1$H NMR spectrum of spiro-dihydropyrone 6a.

FIG. 13 shows a $^{13}$C NMR spectrum of spiro-dihydropyrone 6a.

FIG. 14 shows a $^1$H NMR spectrum of spiro-dihydropyrone 6b.

FIG. 35 shows a $^{13}$C NMR spectrum of spiro-dihydropyrone 6k.

FIG. 36 shows an HPLC scan of a single enantiomer of 4a.

FIG. 37 shows an HPLC scan of racemic 4a.

FIG. 40 shows an HPLC scan of a single enantiomer of 4c.

FIG. 43 shows an HPLC scan of racemic 4d.

FIG. 55 shows an HPLC scan of racemic 4j.

DETAILED DESCRIPTION

Figure 1:
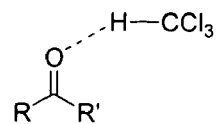
FIG. 1 shows a schematic representation of a C—H—O hydrogen bond formed between chloroform and the oxygen atom of a carbonyl group.

The first general method for performing HDA reactions with unactivated ketones has been discovered and will be described below. This method involves a hitherto unrecognized hydrogen-bond promoted acceleration of the HDA reaction.

In addition, catalysts have been discovered and will be described below that enable an enantioselective version of the HDA reaction using unactivated ketones.

Furthermore, it has been discovered that the above-mentioned catalysts may also be used in a variety of other enantioselective reactions, such as traditional Diels-Alder reactions at the olefin portions of $\alpha$, $\beta$-unsaturated carbonyl compounds, as well as enantioselective non-cycloaddition reactions including the alkynylation of aldehydes.

Throughout this description and in the appended claims, the following definitions are to be understood:

The phrase "complementary to" refers to the reactivity of a first reagent being complementary to the reactivity of a second reagent, such that the first reagent and the second reagent are configured to couple together in a cycloaddition reaction. By way of illustration, a representative pair of complementary first and second reagents corresponds to a diene and a dienophile, which may be coupled together in a Diels-Alder [4+2] cycloaddition to form a 6-membered cycloadduct.

The term "diene" refers to a molecule containing at least two conjugated double bonds. The atoms forming the double bonds may be carbon atoms, heteroatoms, or a combination thereof. The double bonds may be substituted (e.g., with one or more electron donating or electron withdrawing groups) or unsubstituted. Preferably, the double bonds are substituted with one or more electron donating groups.

The term "dienophile" refers to a molecule containing at least one unsaturated bond (e.g., a double bond, a triple bond). The atoms forming the unsaturated bond may be carbon atoms, heteroatoms, or a combination thereof. The unsaturated bond may be substituted (e.g., with one or more electron donating or electron withdrawing groups) or unsubstituted.

The term "alkyl" refers to a substituted or unsubstituted, straight, branched or cyclic hydrocarbon chain containing, preferably, from 1 to 20 carbon atoms. Representative examples of unsubstituted alkyl groups for use in accordance with the present invention include but are not limited to methyl, ethyl, propyl, iso-propyl, cyclopropyl, butyl, iso-butyl, tert-butyl, sec-butyl, cyclobutyl, pentyl, cyclopentyl, hexyl, cyclohexyl, and the like.

The term "alkenyl" refers to a substituted or unsubstituted, straight, branched or cyclic, unsaturated hydrocarbon chain that contains at least one double bond and, preferably, from 2 to 20 carbon atoms. Representative unsubstituted alkenyl groups for use in accordance with the present invention include but are not limited to ethenyl or vinyl (—CH=CH$_2$), 1-propenyl, 2-propenyl or allyl (—CH$_2$—CH=CH$_2$), 1,3-butadienyl (—CH=CHCH=CH$_2$), 1-butenyl (—CH=CHCH$_2$CH$_3$), hexenyl, pentenyl, 1, 3, 5-hexatrienyl, and the like. Preferred cycloalkenyl groups are those having from five to eight carbon atoms and at least one double bond. Representative cycloalkenyl groups for use in accordance with the present invention include but are not limited to cyclohexadienyl, cyclohexenyl, cyclopentenyl, cycloheptenyl, cyclooctenyl, cyclohexadienyl, cycloheptadienyl, cyclooctatrienyl, and the like.

The term "alkoxy" refers to a substituted or unsubstituted —O-Alkyl group. Representative unsubstituted alkoxy groups for use in accordance with the present invention include but are not limited to methoxy, ethoxy, n-propoxy, iso-propoxy, n-butoxy, t-butoxy, and the like.

The terms "siloxy" and "silyloxy" refer to silicon substituted oxygen groups. The silicon-containing portion of the siloxy group may be substituted or unsubstituted. Representative siloxy groups for use in accordance with the present invention include but are not limited to trimethylsilyloxy (—OSi(CH$_3$)$_3$), triethylsilyloxy (—OSi(CH$_2$CH$_3$)$_3$), triisopropylsiloxy (—OSi(i-Pr)$_3$), t-butyldimethylsilyloxy (—OSi(t-Bu)(CH$_3$)$_2$), and the like.

The term "alkynyl" refers to a substituted or unsubstituted, straight, branched or cyclic unsaturated hydrocarbon chain containing at least one triple bond and, preferably, from 2 to 20 carbon atoms.

The term "amino" refers to an unsubstituted or substituted amino (—NH$_2$) group. The amine may be primary (—NH$_2$), secondary (—NHR$^a$) or tertiary (—NR$^a$R$^b$, wherein R$^a$ and R$^b$ are the same or different). Representative substituted amino groups for use in accordance with the present invention include but are not limited to methylamino, dimethylamino, ethylamino, diethylamino, 2-propylamino, 1-propylamino, di(n-propyl)amino, di(iso-propyl)amino, methyl-n-propylamino, t-butylamino, and the like.

The term "halogen" refers to fluorine, chlorine, iodine or bromine.

The term "heterocyclic" refers to a saturated, partially unsaturated, or aromatic ring system containing from 3 to 20, preferably 4 to 8, carbon atoms, and at least one, preferably 1 to 3, heteroatoms. The ring may optionally be substituted with one or more substituents. Moreover, the ring may be mono-, bi- or polycyclic. Preferred heteroatoms for inclusion in the ring include but are not limited to nitrogen, oxygen, and sulfur. Representative heterocyclic groups for use in accordance with the present invention include but are not limited to acridine, benzathiazoline, benzimidazole, benzofuran, benzothiapene, benzthiazole, benzothiophenyl, carbazole, cinnoline, furan, imidazole, 1H-indazole, indole, isoindole, isoquinoline, isothiazole, morpholine, oxazole (i.e. 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i.e. 1,2,3-triazole), and the like.

The term "reactant" refers to a functional group that will react with a second functional group to form at least one bond.

The term "substituted" refers to the optional attachment of one or more substituents onto a backbone structure (e.g., an alkyl group, an alkenyl group, etc.). Representative substituents for use in accordance with the present invention include but are not limited to hydroxyl, amino (—NH$_2$, —NHR$^a$, —NR$^a$,R$^b$), oxy (—O—), carbonyl (—CO—), thiol, alkyl, alkenyl, alkynyl, alkoxy, halo, nitrile, nitro, aryl and heterocyclyl groups. These substituents can optionally be further substituted with 1–3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclyl, heterocyclylaryl, haloalkyl, and the like. The substituent should not substantially interfere chemically with the reaction of the invention (e.g., cross react with reactants, terminate the reaction or the like). When necessary, protecting groups may used to protect functional substituents, as is well known in the art (see: *Protective Groups in Organic Synthesis,* 3$^{rd}$ *Edition* by Theodora W. Greene and Peter G. M. Wuts, John Wiley & Sons, Inc., New York, 1999).

Hydrogen-Bond Promoted Acceleration of HDA Reactions

A variety of spiro-fused dihydropyrans have been synthesized in good yields using the new procedure, which represents an attractive and operationally simple alternative to conventional, Lewis acid catalysis. A representative and non-limiting example of a HDA reaction embodying features of the present invention is shown in the following equation:

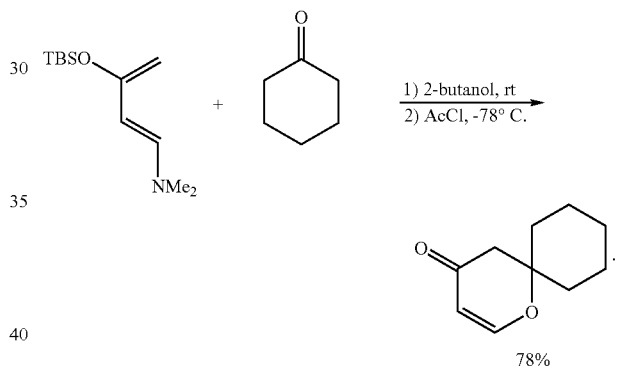

While investigating the solvent effect on the HDA reaction between aldehydes and 1-amino-3-siloxybutadiene, a surprisingly and unexpectedly higher reaction rate in chloroform was observed as compared to other organic solvents that are not capable of participating in hydrogen bonding (e.g., aprotic organic solvents). To more precisely assess the solvent effect, the rate of the HDA reaction between diene 1 and p-anisaldehyde 2 was examined in several different solvents, as shown in Table 1. It is clear from the data in Table 1 that the rate differences do not correlate with the dielectric constant of the solvent: the reaction in chloroform was 10 times faster than in the more polar solvent acetonitrile. Moreover, the higher rate in chloroform cannot be explained by merely invoking catalysis from trace amounts of acid that might be present in the chloroform, since the same rate was observed even after rigorous purification of the solvent. Furthermore, the addition of triethylamine or a catalytic amount of HCl did not affect the rate one way or another (it should be noted, however, that even if there were a trace amount of acid in the solvent, it would be neutralized by the basic nitrogen in the cycloadduct).

TABLE 1

Rates of HDA reactions in different solvents

[Reaction scheme: TBSO-diene with NMe₂ group (1) + MeO-C₆H₄-CHO (2) → TBSO-pyran-Ar with NMe₂ (3), d-solvents, rt]

| entry | solvent | dielectric constant[a] | rate constant (k)[b] | relative rate |
|---|---|---|---|---|
| 1 | THF-$d_8$ | 7.6 | $1.0 * 10^{-5}$ | 1 |
| 2 | benzene-$d_6$ | 2.3 | $1.3 * 10^{-5}$ | 1.3 |
| 3 | acetonitrile-$d_3$ | 37.5 | $3.0 * 10^{-5}$ | 3.0 |
| 4 | chloroform-d | 4.8 | $3.0 * 10^{-4}$ | 30 |
| 5 | t-butanol-$d_{10}$ | 10.9 | $2.8 * 10^{-3}$ | 280 |
| 6 | i-propanol-$d_8$ | 18.3 | $6.3 * 10^{-3}$ | 630 |

[a] For the corresponding undeuterated solvent, at 25° C. ± 5°.
[b] Kinetics measured by NMR integration using internal standard.

Without wishing to be bound by a particular theory or to in any way limit the scope of the appended claims or their equivalents, it is presently believed that the increased reaction rate in chloroform arises from a C—H—O hydrogen bond between chloroform and the carbonyl oxygen, which would render the carbonyl group a stronger hetero-dienophile, as shown in FIG. 1. The rate of the HDA reaction in deuteriochloroform was the same, within experimental error, as that in chloroform.

As the data in Table 1 above show, the cycloadditions are accelerated to a much greater extent in hydrogen bonding solvents, in which the OH group may be expected to form a strong hydrogen bond to the aldehyde oxygen. Thus, the HDA reaction of 1 and anisaldehyde is 630 times faster in deuterated isopropanol than in deuterated THF, which corresponds to a ΔΔG‡ of −3.77 kcal/mol.

Surprisingly and unexpectedly, the activation provided by hydrogen bonding solvents is sufficient to enable even simple ketones, which according to conventional wisdom have generally been considered unreactive, to undergo the HDA reaction. Initially, the HDA reaction of cyclohexanone and diene 1 in chloroform was examined, as shown in Table 2 below. Remarkably, although slow, the cycloaddition with this unactivated ketone proceeded cleanly and gave, upon acetyl chloride mediated elimination of the amino group, the desired spiro-fused dihydropyrone in 45% yield, along with E-4-(N,N-dimethylamino)-3-buten-2-one 5 (which may be obtained readily from the hydrolysis or solvolysis of diene 1).

TABLE 2

Reactions of Cyclohexanone and 1 in Hydrogen-bonding Solvents.

[Reaction scheme: TBSO-diene with NMe₂ (1) + cyclohexanone → spiro dihydropyrone 6a; 1) solvent, rt; 2) AcCl, −78° C.]

| entry | solvent | time (h) | solvolysis (%)[a] | yield (%)[c] |
|---|---|---|---|---|
| 1 | chloroform | 48 | 20–25 | 45 |
| 2 | t-butanol | 24 | <5 | 71 |
| 3 | i-propanol | 3 | 10–15 | 60 |
| 4 | ethanol | 0.5 | ~50[b] | 30 |
| 5 | methanol | 0.5 | ~40[b] | 0 |
| 6 | 2-butanol | 5 | <5 | 78 |

[a] Percentage of hydrolysis was calculated by NMR integration.
[b] A significant amount of other type of decomposition took place as well as hydrolysis.
[c] Yields refer to isolated, chromatographically purified products, except for entries 4 and 5, in which the yields are based on NMR integration of cycloadduct.

As the data in Table 2 show, the cycloaddition was considerably faster in hydrogen bonding solvents. The reaction went to completion in 1 day in t-BuOH and, upon acetyl chloride workup, afforded the expected spiro product in 71% yield. Solvents with less shielded hydroxyl groups were more effective at accelerating the HDA reaction.

The reaction went to completion in just 3 h in i-propanol, but the desired cycloadduct was accompanied by a significant amount (10–15%) of the solvolysis byproduct 5. Diene solvolysis predominated in ethanol and methanol. The results indicate that although better hydrogen bonding alcohols promote faster reactions, they also solvolyze the diene. The use of 2-butanol (entry 6) provides a good compromise: the reaction was reasonably fast and was accompanied by little of the undesired solvolysis byproduct.

This hydrogen bond promoted protocol represents the first general method for achieving the HDA reactions of unactivated ketones. A series of reactions was carried out conveniently by mixing the diene and the ketone in 2-butanol and letting the resulting solution stir at room temperature for the indicated time. The results are shown in Table 3 below. The alcohol was removed in vacuo and replaced with dichloromethane. After cooling to −78° C., acetyl chloride was added, and the resulting solution subjected to an aqueous workup and chromatographic purification. This simple, one-pot procedure allows the preparation of a variety of structurally novel spiro-dihydropyrones in good yields.

TABLE 3

Cycloaddition Reactions of Diene 1 and Unactivated Ketones

| entry | ketone | time[a] | product | ratio | yield (%)[c] |
|---|---|---|---|---|---|
| 1 | cyclohexanone | 5 h | 6a | | 78 |
| 2 | 2-methylcyclohexanone | 4 d | 6b | | 35 |
| 3 | 3-methylcyclohexanone | 5.5 h | 6c | 4.2:1 | 75 |
| 4 | 4-methylcyclohexanone | 5.5 h | 6d | 2.8:1 | 74 |
| 5 | 4-tert-butylcyclohexanone | 5.5 h | 6e | 3:1 | 76 |
| 6[b] | 2-methoxycyclohexanone | 8 h | 6f | 1.5:1 | 81 |
| 7 | N-Cbz-4-piperidone | 3 h | 6g | | 82 |
| 8 | cyclopentanone | 19 h | 6h | | 41 |

TABLE 3-continued

Cycloaddition Reactions of Diene 1 and Unactivated Ketones

| entry | ketone | time[a] | product | ratio | yield (%)[c] |
|---|---|---|---|---|---|
| 9 | acetone | 30 h | 6i | | 40 |
| 10 | methoxyacetone | 6 h | 6j | | 33[d] |
| 11 | pivaldehyde (tBu-CHO) | 1.5 h | 6k | | 77 |

[a]All reactions were carried out on an approximately 0.5 mmol scale in 0.5 mL 2-butanol using 2 equivalents of ketone.
[b]The ketone was dissolved in 0.2 mL of benzene.
[c]Yields refer to chromatographically purified products.
[d]An equal amount of the Mukaiyama aldol side product was formed.

Figure 2:
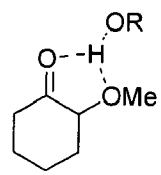
FIG. 2 shows a schematic representation of a hydrogen bond formed between the methoxy oxygen of 2-methoxycyclohexanone and the proton of the hydroxyl group of an alcohol solvent.

HDA reactions in accordance with the present invention are sensitive to steric and electronic variations in the ketone. Whereas the reaction of diene 1 and cyclohexanone went to completion in just 5 hours, the reaction with 2-methylcyclohexanone was only ca. 50% complete after 4 days (entry 2). By contrast, 2-methoxycyclohexanone was comparable in reactivity to cyclohexanone (entry 6). Evidently, the inductive effect of the methoxy group and its capacity to hydrogen bond override the steric effect, as shown in FIG. 2.

Substituents at the 3 or 4 positions of cyclohexanone do not retard the reaction (entries 3–4). In general, six-membered ring ketones are more effective as heterodienophiles than other ketones (cf. entries 8–10). Finally, the HDA reaction of the hindered aldehyde, pivaldehyde, is greatly accelerated in a hydrogen bonding solvent (entry 11). The corresponding reaction in chloroform was considerably slower and afforded the product in 54% product after 2 days (cf. Huang, Y.; Rawal, V. H. *Org. Lett.*, 2000, 2, 3321).

The above-described results demonstrate the HDA reactions are greatly accelerated in hydrogen bonding solvents in accordance with the present invention. This activation protocol represents an attractive and operationally simple alternative to conventional, Lewis acid catalysis.

Based on a joint consideration of the description herein and the representative procedures described below, the manner of making and using the present invention will be abundantly clear to one of ordinary skill in the art. For direction and guidance of a more general nature, the following representative literature materials are provided.

For further description of hydrogen-bond promoted acceleration HDA reactions in accordance with the present invention, see: Huang, Y.; Viresh, V. H. *J. Am. Chem. Soc.*, 2002, 124, 9662–9663, the entire contents of which are incorporated herein by reference, except that in the event of any inconsistent disclosure or definition from the present application, the disclosure or definition herein shall be deemed to prevail.

For a summary of conventional HDA chemistry, see: (a) Tietze, L. F.; Kettschau, G. *Top. Curr. Chem.*, 1997; 189, 1, and references therein. For earlier work, see: (b) Boger, D. L.; Weinreb, S. M. *Hetero Diels-Alder Methodology in Organic Synthesis*, Wasserman, H. H., Ed.; Academic Press: San Diego, Calif., 1987; Vol. 47.

For reviews on oxygen heterocycles, see: (a) Schmidt, R. R. *Acc. Chem. Res.*, 1986, 19, 250. (b) Danishefsky, S. J.; DeNinno, M. P. *Angew. Chem. Int Ed. Engl.*, 1987, 15, 5. (c) Kametani, T.; Hibino, S. *Adv. Heterocycl. Chem.*, 1987, 42, 245. (d) Bednarski, M. D.; Lyssikatos, J. P. In: *Comprehensive Organic Synthesis*; Trost, B. M., Heathcock, C. H., Ed.; Pergamon Press: New York, 1991; Vol. 2, pp 661.

For a description of the special reaction conditions (e.g., high temperature, high pressure, Lewis acid catalysis) required to perform conventional HDA reactions, see: (a) Pindur, U.; Lutz, G.; Otto, C. *Chemical Reviews*, 1993, 93, 741. (b) Klärner, F.-G.; Wurche, F. J. Prak. Chem., 2000, 342, 609. (c) Kumar, A. *Chem. Rev.*, 2001, 101, 1.

For examples of the difficulty of performing HDA reactions using simple ketones, compare inter alia: (a) Guay, V.; Brassard, P. *Tetrahedron*, 1984, 40, 5039. (b) Schiess, P.; Eberle, M.; Huys-Francotte, M.; Wirz, J. *Tetrahedron Lett.*, 1984, 25, 2201. (c) Midland, M. M.; Graham, R. S. *J. Am. Chem. Soc.*, 1984, 106, 4294. (d) Daniewski, W. M.; Kubak, E.; Jurczak, J. *J. Org. Chem.* 1985, 50, 3963. (e) Rigby, J. H.; Wilson, J. A. Z. *J. Org. Chem.*, 1987, 52, 34. (f) Chino, K.; Takata, T.; Endo, T. *Synth. Commun.*, 1996, 26, 2145. (g) Brouard, C.; Pornet, J.; Miginiac, L. *Synth. Commun.*, 1994, 24, 3047; (h) Huang, Y.; Rawal, V. H. Org. Left., 2000, 2, 3321.

For a description of the HDA reaction between aldehydes and 1-amino-3-siloxybuadiene, see: (a) Huang, Y.; Rawal, V.

H. *Org. Lett.*, 2000, 2, 3321. See also: (b) Kozmin, S. A.; Janey, J. M.; Rawal, V. H. *J. Org. Chem.*, 1999, 64, 3039. (c) Kozmin, S. A.; Green, M. T.; Rawal, V. H. *J. Org. Chem.*, 1999, 64, 8045. (d) Kozmin, S. A.; Rawal, V. H. *J. Am. Chem. Soc.*, 1999, 121, 9562. (e) Huang, Y.; Iwama, T.; Rawal, V. H. *J. Am. Chem. Soc.*, 2000, 122, 7843.

For information regarding the C—H—O hydrogen bond between chloroform and carbonyl oxygens, see: (a) Green, R. D. Hydrogen Bonding by C—H Groups; Wiley: New York, 1974. (b) Steiner, T. *New. J. Chem.*, 1998, 1099. (c) Kryachko, E. S.; Zeegers-Huyskens, Z. *J. Phys. Chem. A.*, 2001, 105, 7118, and citations therein.

For information relating to the well-established acceleration of Diels-Alder reactions in water, see: (a) Breslow, R. *Acc. Chem. Res.*, 1991, 24, 159. (b) Grieco, P. A. 133 *Aldrichimica Acta*, 1991, 24, 59. (c) Labineau, A.; Augé, J. *Top. Curr. Chem.*, 1999, 206, 2.

For information relating to the hydrogen bond activation of dienophiles in standard Diels-Alder reactions, see: (a) Kelly, T. R.; Meghani, P.; Ekkundi, V. S. *Tetrahedron Lett.*, 1990, 31, 3381. (b) Schuster, T.; Kurz, M.; Göbel, M. W. *J. Org. Chem.*, 2000, 65, 1697. (c) Schreiner, P. R.; Wittkopp, A. *Org. Lett.*, 2002, 4, 217.

Asymmetric Catalysis of Cycloaddition Reactions

Despite the central role of hydrogen bonding in determining the structure and function of proteins, nucleic acids, and many supramolecular assemblies, this weak interaction has hitherto been rarely utilized as a force for promoting chemical reactions. However, it has now been discovered that a chiral alcohol—through H-bonding—not only effectively catalyzes an important family of cycloaddition reactions, but does so with exquisite levels of enantioselectivity.

Since most molecules of life (e.g., DNA, proteins, etc.) and many pharmaceutical drugs are chiral (i.e., not superimposable on their mirror images or enantiomers), reactions that selectively produce one enantiomer of a chiral compound are vitally important. Chemical catalysts that have been developed to address this need are generally based on Lewis acidic metals. The above-described discovery that the HDA reactions of unactivated ketones and 1-amino-3-siloxy diene may be significantly accelerated in hydrogen bonding solvents prompted an investigation of the use of chiral alcohols for the catalysis of such cycloadditions.

Surprisingly and unexpectedly, the catalytic effect provided by hydrogen-bond donors can be extended to asymmetric or enantioselective synthesis. Throughout this description and in the appended claims, the terms "asymmetric" and "enantioselective" are used interchangeably. Presently preferred chemical reactions that may be used in accordance with the present invention are reactions in which chiral hydrogen-bond donors can produce products having an excess of one enantiomer in relation to the other possible enantiomer. Representative chemical reactions include but are not limited to, Diels-Alder reactions, dipolar cycloadditions, carbene additions, cyclopropanation, aziridination, additions of nucleophiles to carbonyl groups (e.g., by Grignard reagents, stannanes, silanes, organozines, and other organometallics), addition of nucleophiles to alpha, beta-unsaturated carbonyls (e.g., by Grignard reagents, stannanes, silanes, organozincs, cuprates, organomaganese compounds, and other organometallics), nucleophilic addition to imines, cyanohydrin formation, cyanoamine formation, reductions of ketones and imines, and the like.

Without wishing to be bound by a particular theory or to in any way limit the scope of the appended claims or their equivalents, it is presently believed that an enantioselective reaction occurs due to coordination of a hetero-olefin, such as a carbonyl group or an imine group, to the chiral hydrogen-bond donor, such as an alcohol. This coordination is presently believed to occur through hydrogen bonding and/or other non-bonding interactions and to hinder the approach of the reactant to one face of the hetero-olefin in relation to the other face of the hetero-olefin. Consequently, the addition of the reactant takes place selectively to one face of the hetero-olefin over the other face. Similarly, with alpha, beta-unsaturated carbonyl compounds and alpha, beta-unsaturated imine compounds, the coordination to the chiral hydrogen-bond donor is presently believed to selectively block the carbonyl carbon (or the imine carbon) in addition to the alpha and beta carbons. The result is that reactants are presently believed to selectively react on one face of these planar groups over the other. Thus, the two faces of the hetero-olefin become prochiral. Such selectively is also commonly referred to as enantiofacial selectivity.

In a presently preferred embodiment, highly enantioselective HDA reactions are catalyzed with chiral hydrogen-bond donors, including alcohols. The resultant cycloadduct products are produced in good yields with extremely high optical purity. In addition, metal and Lewis acid free hydrogen-bond donor catalysts are provided that offer advantages over conventional metal catalyzed reactions. These benefits include but are not limited to lower cost, increased sensitivity, and increased environmental friendliness. The extension of the above-described hydrogen bond acceleration concept to asymmetric synthesis is further explained below.

Asymmetric synthesis or enantioselective synthesis occurs when one of two possible enantiomeric products is preferentially formed from a reaction. Enantiomeric excess (ee) is a measure of the preference for one enantiomer over the other. Thus, if R and S type enantiomers are possible and a reaction produces more of the R enantiomer than the S enantiomer, the ee for the reaction will reflect the degree of preference for formation of the R enantiomer.

A hydrogen bond may form when a covalently bonded hydrogen atom is in close proximity to a heteroatom. For example, if the hydrogen atom covalently bonded to the oxygen atom of an alcohol comes in close contact with the oxygen of a carbonyl group, a hydrogen bonding interaction can occur between the hydrogen atom and the oxygen of the carbonyl. The alcohol having the hydrogen atom covalently bonded to the oxygen serves as a hydrogen-bond donor. The carbonyl group serves as a hetero-olefin. If the carbonyl were to be further reacted with a diene in a Diels-Alder type reaction, the carbonyl would serve as a hetero-dienophile. Representative heteroatoms for participation in the formation of hydrogen bonds include but are not limited to oxygen, nitrogen, sulfur, fluorine, and chlorine.

Catalytic, enantioselective HDA reactions are an efficient method for the construction of optically active six-membered heterocycles. In these reactions, a diene, which includes two or more conjugated double bonds is reacted with a hetero-olefin. Hetero-olefins used in Diels-Alder reactions are often referred to as hetero-dienophiles or, more generally, dienophiles.

A typical, asymmetric catalyzed Diels-Alder reaction between a diene and a hetero-olefin (dienophile) is shown in Scheme 1 below:

Scheme 1

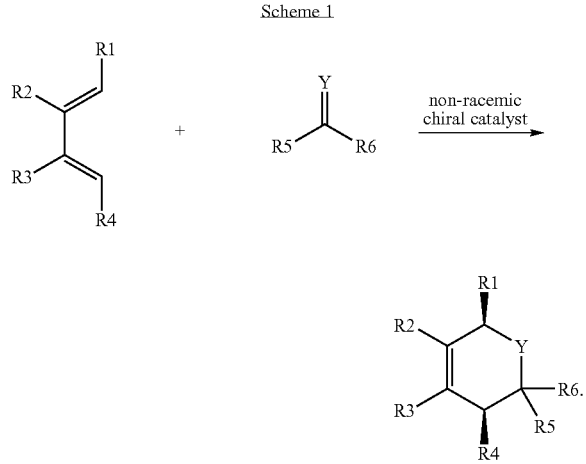

Y represents O, S, or NR7. R1, R2, R3, R4, R5 and R6 each independently represents hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$— R8. Any two or more of the substituents R1, R2, R3, R4, R5 and R6 taken together may form a carboxylic or heterocyclic ring having from 4 to 8 atoms in the ring structure. R8 represents an aryl, a cycloalkyl, a cycloalkenyl, a heterocycle or a polycycle; and m is an integer from 0 to 8. In certain embodiments, R1, R2, R3, and R4 are chosen such that the substrate has a plane of symmetry.

Exemplary dienophiles suitable for use in accordance with the present invention include but are not limited to aldehydes, ketones, esters, amides, carbonates, thioaldehydes, thioamides, thiocarbonates, lactones, lactams, thiolactones, thiolactams, imines, oximes, hydrazones, thionoesters, thioesters, dithioesters, thionolactones, dithiolactones, phosphorus ylides, thioketones, acid halides, anhydrides, iminium ions, nitroso-containing compounds, nitro-containing compounds, compounds containing a phosphorus-oxygen π-bond, and compounds containing a phosphorus-sulfur π-bond.

As noted above, conventional methods for catalyzing asymmetric Diels-Alder reactions typically involve the use of metals, such as Lewis acids. Examples of the conventional methodologies are shown in Schemes 2–7 below.

Scheme 2-Asymmetric Diels-Alder reactions with a Lewis Acid catalyst.

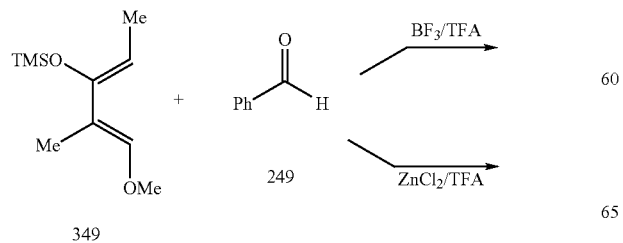

Lewis acid catalysis has been extended to use chiral ligands for asymmetric induction. With a sterically demanding chiral ligand in proximity, the two pro-chiral faces of a carbonyl group can be differentiated. The change in hybridization of oxygen from Sp$^2$ to Sp$^3$ favors turnover of the precious chiral catalyst.

Scheme 3-Enantioselective HDA Reactions Catalyzed by a Metal Catalyst.

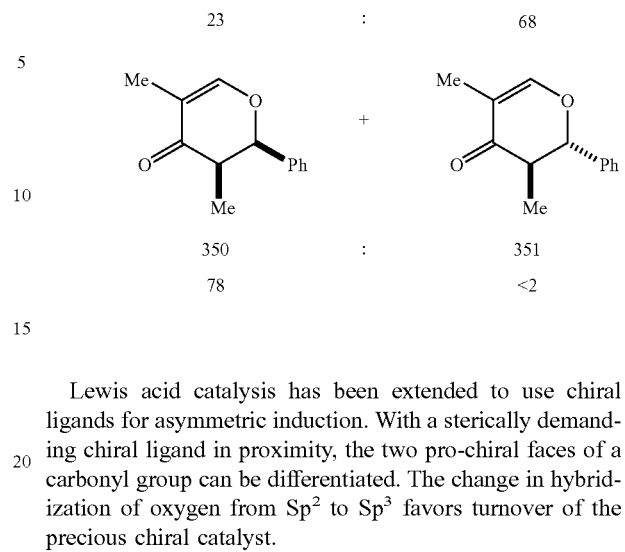

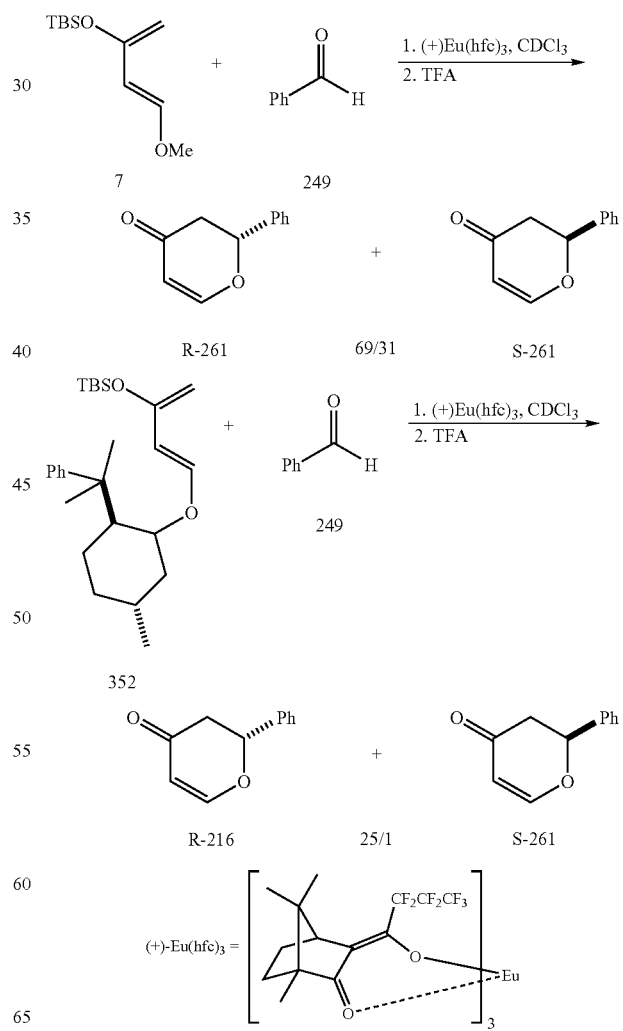

Scheme 4-
Enantioselective HDA Reactions of Aldehydes with a Metal Catalyst
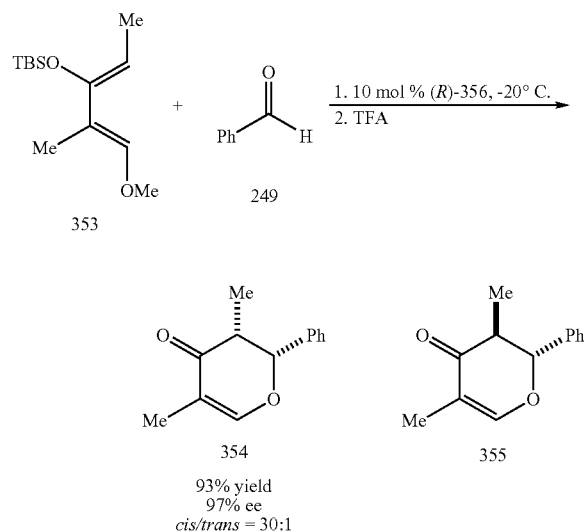
Scheme 5-
HDA Reactions Catalyzed by Tryptophan-derived Lewis Acid Catalyst
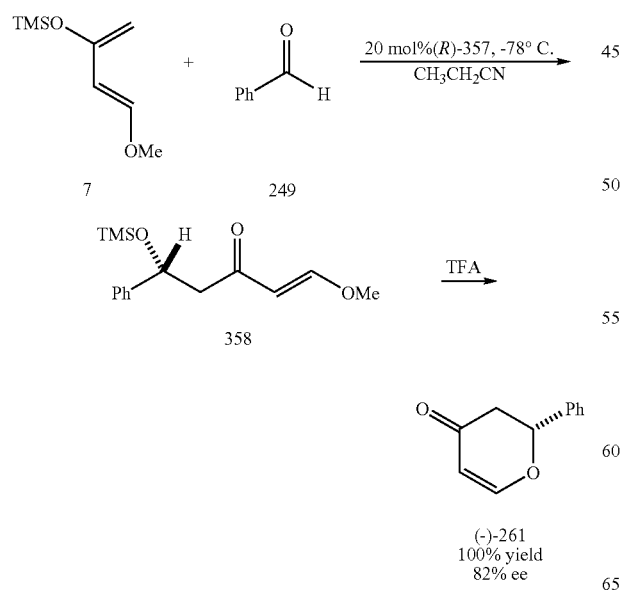
Scheme 6-HDA and Ene Reactions Catalyzed by Metal Catalysts
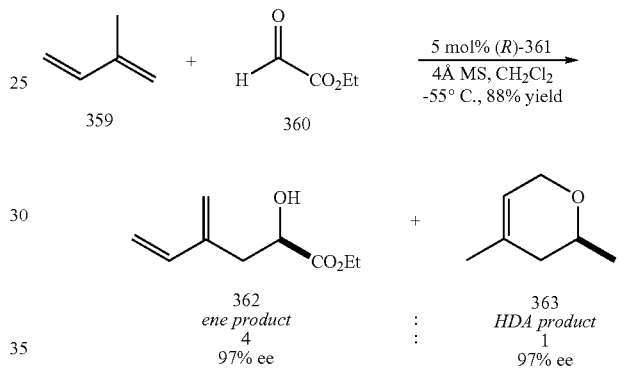
Scheme 7-
Chemoselective HDA Reactions Catalyzed by Metal Catalyst
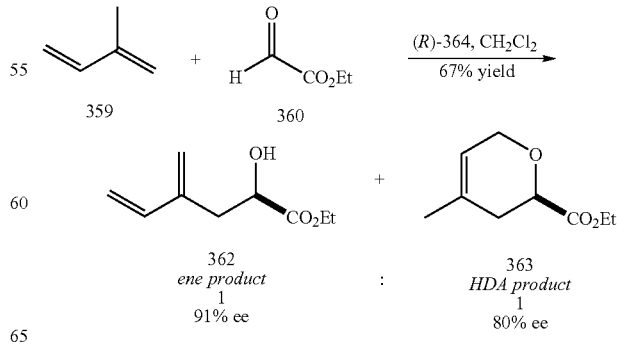

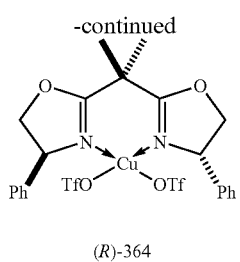

(R)-364

Figure 3:
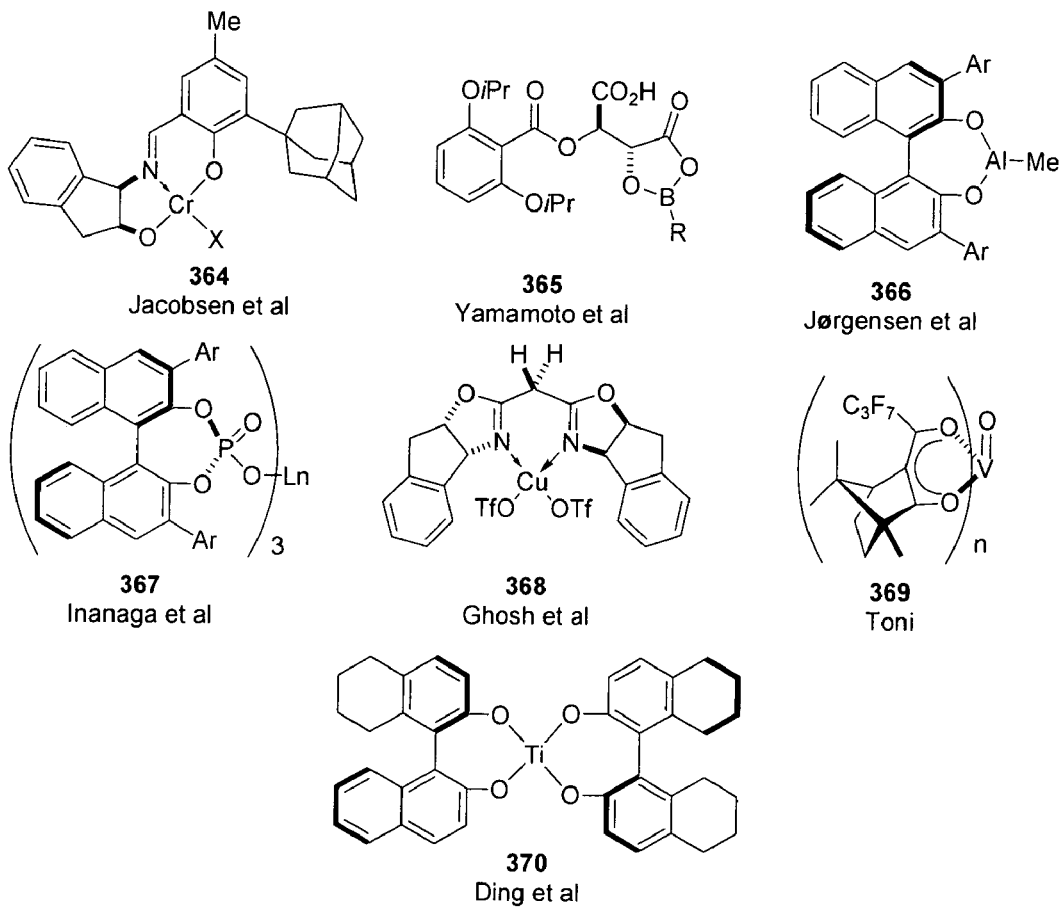
FIG. 3 shows a group of metal-containing and Lewis acid catalysts that have been used for conventional HDA reactions.

FIG. 3 shows a group of representative metal-containing and Lewis acid catalysts that have been used for HDA reactions.

Hydrogen bonds may activate certain types of chemical reactions. However, too little reaction activation from the hydrogen bonding interaction can be a limiting factor since the strength of a hydrogen bonding interaction is generally less than that of a Lewis acid.

As noted above, HDA reactions in accordance with the present invention are greatly accelerated by solvents capable of hydrogen bonding. For example, as shown in Scheme 8 below, the reaction rate in 2-butanol was >600 times faster than in benzene and THF. The rate difference accounts for more than a 3.5 kcal/mol activation energy drop at 25° C. Surprisingly and unexpectedly, good enantioselectivity is achieved when an appropriate chiral alcohol is used.

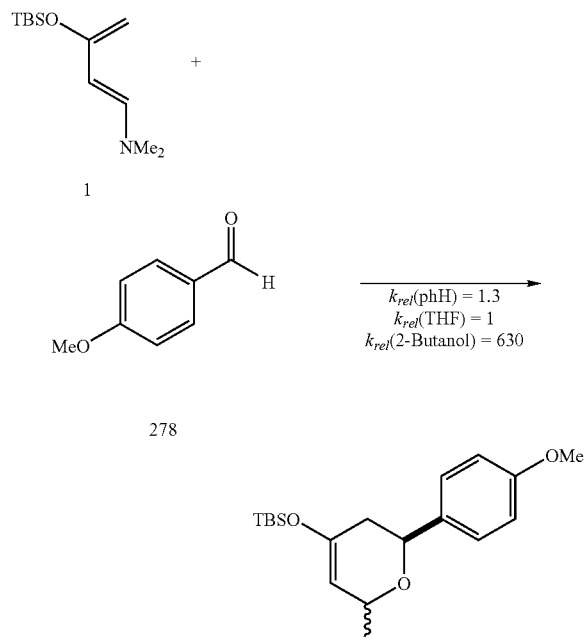

Figure 4:
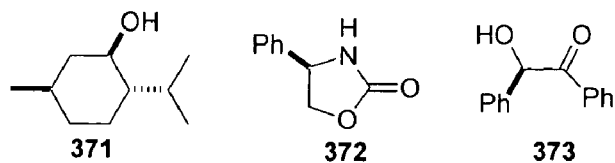
FIG. 4 shows three chiral acidic hydrogen-bond donors, each having one acidic proton, which were examined in accordance with the development of the present invention.

The reaction between diene 1 and benzaldehyde 278 shown in Scheme 8 above was used as a model for examining several chiral acidic hydrogen-bond donors which have one acidic proton. These hydrogen-bond donors are shown in FIG. 4. The reaction was carried out using 2 equivalents of chiral hydrogen-bond donor. Under these conditions, oxazolidinone 372 and benzoin 373 caused significant diene decomposition, resulting in little product being isolated. Additionally, menthol 371 failed to provide decent activation. The reaction was also very slow at low temperature (−78 to 0° C.). However, the product obtained from room temperature reaction was isolated in poor yields and with a low enantiomeric excess of only about 3%. Although low, a slight enantioselectivity was thus demonstrated. Accordingly, these conditions were further optimized.

Figure 5:
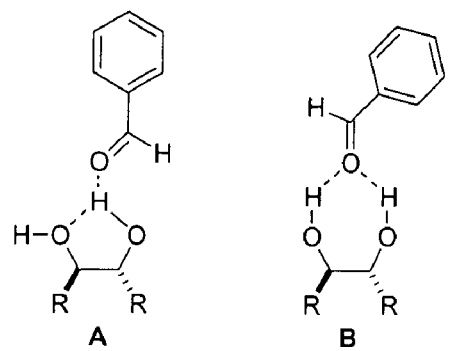
FIG. 5 shows two models for chiral diol activation in accordance with the present invention.

Without wishing to be bound by a particular theory or to in any way limit the scope of the appended claims or their equivalents, it is presently believed that 1,2-diols potentially have the benefit of forming complexes of type A or type B shown in FIG. 5. In model A, intramolecular hydrogen-bonding of the catalyst may provide additional activation. In model B, a possible di-hydrogen-bonding interaction of the catalyst with the aldehyde could potentially double the degree of activation provided.

Figure 6:
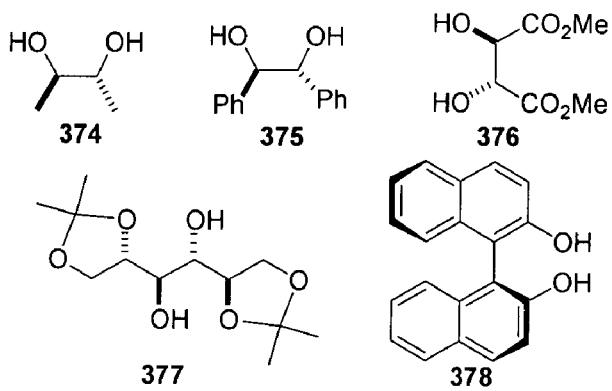
FIG. 6 shows a series of chiral diols tested in accordance with the development of the present invention.

Under one set of conditions, (R)-BINOL 378 and L-tartaric acid dimethyl ester 376 resulted in diene decomposition. It is now believed that these alcohols may be too acidic to be compatible with diene 1. Under similar conditions, (R,R)-hydrobenzoin 375 did not significantly catalyze the HDA reaction, and the diene was slowly hydrolyzed. (R,R)-2,3-Butanediol 374 and D-mannitol diacetonide 377 did catalyze the HDA reaction, but only to a slight degree (ee value of 3% and 6%, respectively, were determined by chiral HPLC). FIG. 6 shows a series of chiral diols tested during this stage of the development. Further optimization of the conditions for catalyzing HDA reactions with these alcohols was performed as described below.

Figure 7:
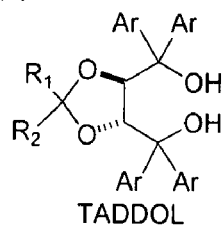
FIG. 7 shows a generic structure of TADDOL.

A class of chiral diols known as TADDOLs was next examined in connection with the HDA reaction between diene 1 and benzaldehyde. TADDOL is an abbreviation for α,α,α′,α′-tetraaryl-2,2-dimethyl-1,3-dioxolan-4,5-dimethanol, shown in FIG. 7, which include a series of acetals and ketals of 1,1,4,4-tetraarylthreitols (see, for example: Seebach, D.; Beck, A. K.; Heckel, A. *Angew. Chem. Int. Ed.,* 2001, 40, 92–138).

Surprisingly and unexpectedly, TADDOL type diols provided excellent results, as shown in Scheme 9 below. TADDOL 379 was moderately soluble in toluene at room temperature. Upon addition of 2 equivalents of benzaldehyde, the opaque mixture turned clear immediately and remained clear even at −78° C. The increased solubility of TADDOL in the presence of benzaldehyde suggested a strong interaction between the diol and the carbonyl. A smooth HDA reaction occurred upon addition of 1-amino-3-siloxybutadiene 1 at −78° C. Crude $^1$H NMR indicated that a single diastereomer was being formed, tentatively believed to be an endo isomer. Acetyl chloride workup afforded dihydropyran 261 in 47% yield. The product was separated on a chiral HPLC column (Diacel OD-H) and the ee was determined to be 37%.

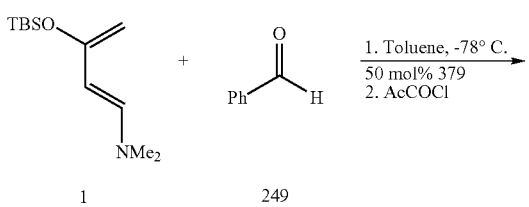

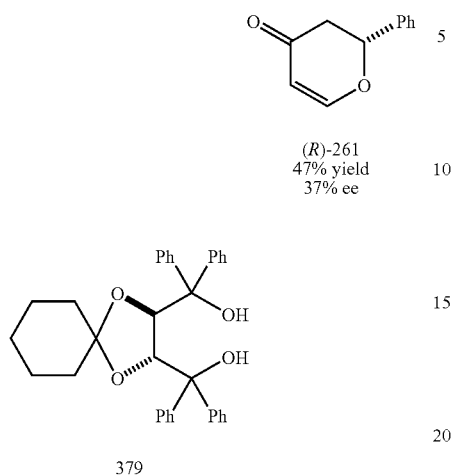

(R)-261
47% yield
37% ee

379

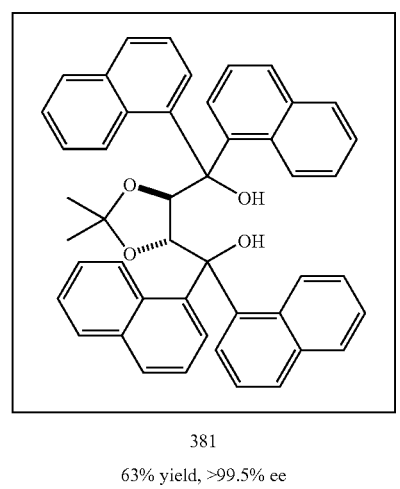

381
63% yield, >99.5% ee

Scheme 9 clearly demonstrates the concept of asymmetric catalysis by a chiral hydrogen bond donor. A sub-stoichiometric amount of chiral diol was used, and good catalyst turnover was achieved.

Two additional TADDOLs, as shown in Scheme 10 below, were purchased from Aldrich Chemical Co. (Milwaukee, Wis.) and used to catalyze the HDA reaction between 1 and 249. 2-Naphthyl TADDOL 380 resulted in more undesirable products being formed than with TADDOL 379. A NMR calculated yield for the reaction was ~30%. However, the product had an enantiomeric excess of 68%, demonstrating the significant enantioselectivity of the reaction. Surprisingly and unexpectedly, 1-naphthyl TADOOL 381 afforded a very clean reaction with few side products and the desired cycloadduct product was isolated in 63% yield. Remarkably, the ee of the cycloadduct approached nearly 100%, giving a greater than 200:1 enantiomeric ratio in the chiral HPLC spectrum.

Scheme 10-Results with Naphthyl-TADDOLs

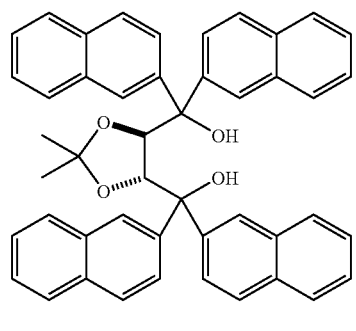

380
<30% yield, 68% ee

The catalyst loading was further lowered to 20 mmol %. Nonetheless, the HDA reaction was almost complete after 48 hours at −78° C. and, remarkably, Dihydropyran 261 was separated in a 70% yield and >99% ee after silica gel chromatography.

TADDOL is readily prepared from tartaric acid diesters through a Barbier-Wieland reaction sequence: addition of excess aryl Grignard reagent to ester affords the corresponding diarylcarbinol functionality of TADDOL. The tertiary alcohols allow convenient derivatization in a sense of combinatorial optimization. Heteroatoms including but not limited to halogens, O, N, P, S, Si, and B can be easily incorporated into the TADDOL framework. Other small chiral molecules (as opposed to tartrates) can also be introduced for asymmetry. Thousands of versatile ligands and catalysts bearing the TADDOL skeleton have been prepared and utilized in asymmetric reactions, as shown in FIG. 8.

An advantageous property of TADDOLs is their tendency to form crystalline solids. There are roughly 120 crystal structures of compounds of the type shown in FIG. 8. The TADDOL skeleton adopts a nearly perfect staggered, $C_2$-symmetric conformation, as shown in FIG. 9. A vast number of reactions in which TADDOL and TADDOL derivatives are used to activate hetero-olefins for further reaction are contemplated in accordance with the present invention particularly vis-à-vis Diels-Alder reactions in which a hetero-olefin serves as a dienophile.

Without wishing to be bound by a particular theory or to in any way limit the scope of the appended claims or their equivalents, it is presently believed that the chirality from the stereogenic centers on the dioxolane ring was amplified through a propeller-shape structure. Two of the aryl groups are presently believed to orient axially, while the other two aryl groups are presently believed to orient equatorially. At least one of the alcoholic protons is presently believed to participate in an intramolecular hydrogen bond, leaving the other alcoholic proton free for intermolecular interaction with the hetero-olefin.

Without wishing to be bound by a particular theory or to in any way limit the scope of the appended claims or their equivalents, it is further presently believed that hydrogen bonding plays a very important role in TADDOL based asymmetric synthesis. The formation of an inclusion complex may be energetically driven by hydrogen bonding between TADDOL and the electronegative atoms in the substrates. The success in the resolution of racemic mixtures clearly shows that TADDOLs are able to bind to one enantiomer from a racemic mixture with a selectivity greater than 100:1. Thus, it is presently believed that TADDOLs may also provide significant activation of carbonyls through a hydrogen bonding interaction.

All manner of aldehydes and ketones are contemplated for use as hetero-olefins for use in accordance with HDA reactions embodying features of the present invention. As shown by the data in Table 4 below, both aromatic and aliphatic aldehydes participated in HDA reactions at low temperature in the presence of 20 mol % of 1-naphthyl-TADDOL. Dihydropyrans 4 were isolated in 50–97% yields with excellent ee.

TABLE 4

Highly Enantioselective HDA Reactions Catalyzed by 1-Naphthyl

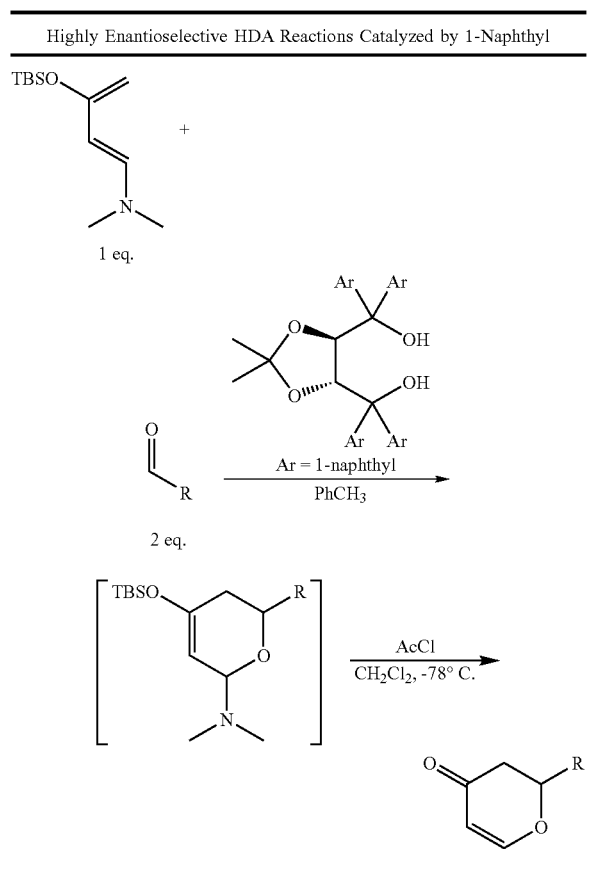

| Entry | R | Temp (° C.) | Time (h) | Yield (%) | ee (%) |
|---|---|---|---|---|---|
| 1 | Ph | −78 | 48 | 70 | 98 |
| 2 | 4-MeO—$C_6H_4$ | −40 | 24 | 68 | 94 |
| 3 | 2-$O_2$N$C_6H_4$ | −20 | 24 | 69 | 80 |
| 4 | 4-$F_3$C—$C_6H_4$ | −78 | 48 | 68 | 95 |
| 5 | 1-naphthyl | −78 | 48 | 69 | 99 |
| 6 | 4-Me$C_6H_4$ | −78 | 48 | 68 | 98 |
| 7* | 4-Cl$C_6H_4$ | −78 | 48 | 60 | 85 |
| 8 | $C_6H_5$C$H_2$O$CH_2$ | −78 | 48 | 40 | 97 |
| 9 | $C_6H_{11}$ | −40 | 24 | 64 | 87 |
| 10 | PhC$H_2$C$H_2$ | −40 | 48 | 73 | 71 |
| 11 | 2-naphthyl | −40 | 24 | 97 | 94 |
| 12 | 2-furyl | −78 | 48 | 67 | 92 |
| 13 | propyl | −40 | 10 | 71 | 88 |
| 14 | m-Br-phenyl | −78 | 24 | 61 | 97 |
| 15 | trans-styrenyl | −45 | 20 | 52 | 95 |

*A 1:1 mixture of toluene and methylene chloride was used to dissolve the substrate at −78° C.

A suspension of 0.25 mmol of (R,R)-1-naphthyl TADDOL (381, purchased from Aldrich) in toluene at −78° C. became homogeneous upon addition of 1.0 mmol of benzaldehyde. Subsequent addition of 0.5 mmol of 1-amino-3-siloxybutadiene 1 caused a smooth HDA reaction to take place. Analysis of the crude reaction mixture by $^1$H NMR indicated the formation of the expected cycloadduct as a single diastereomer (R=$C_6H_5$), tentatively assigned as endo. Upon treatment with acetyl chloride (1.0 mmol, −78° C.), the cycloadduct was converted to a dihydropyrone (R=$C_6H_5$), which was isolated in 63% overall yield. Chiral HPLC analysis showed that the reaction had produced the S-enantiomer preferentially over the R with >99:1 enantiomer ratio (r). The reaction was equally effective using only 20 mol % of catalyst 2 (70% yield,>99:1 r). The reaction rate acceleration provided by TADDOL 381 is considerable: in its absence, no reaction took place under otherwise identical conditions. The full hydrogen bonding capability of 381 is presently believed to facilitate catalysis. The dimethylether derivative of 381 was ineffective as a catalyst and the monomethyl ether gave poor catalysis.

This metal-free asymmetric catalysis method, which does not involve a covalent connection between the catalyst and the reactant (see: Dalko, P. I.; Moisan, L. Angew. Chem. Int. Ed., 2001, 40, 3726–3748) is useful for the cycloadditions between 1 and a range of aldehydes.

Aromatic aldehydes were particularly effective as dienophiles in these catalyzed HDA reactions. The resultant dihydropyrone products were obtained in uniformly high enantiomer ratios. However, the conditions were not optimized. The reaction required slightly higher temperature and ee dropped to 88% for n-butyraldehyde. Nevertheless, this methodology represents enantioselective HDA reactions catalyzed by chiral hydrogen-bond donors (organocatalysts). The successful use of aliphatic and α,β-unsaturated aldehydes (e.g., entry 15) in these reactions is noteworthy.

Based on a joint consideration of the description herein and the representative procedures described below, the manner of making and using the present invention will be abundantly clear to one of ordinary skill in the art. For further description of asymmetric catalysis of cycloaddition reactions in accordance with the present invention, see: Huang, Y.; Unni, A. K.; Thadani, A. N.; Rawal, V. H. Nature, 2003, 424, 146, the entire contents of which are incorporated herein by reference, except that in the event of any inconsistent disclosure or definition from the present application, the disclosure or definition herein shall be deemed to prevail.

Asymmetric Catalysis of Diels-Alder Reactions with α,β-Unsaturated Carbonyl Dienophiles It has further been discovered that the above-described catalysts are not limited to the catalysis of HDA reactions but rather are also useful for the catalysis of traditional (i.e., non-hetero) Diels-Alder cycloadditions with dienophiles including but not limited to α,β-unsaturated carbonyl compounds. A presently preferred class of dienophiles for use in accordance with this aspect of the present invention is α,β-unsaturated aldehydes, such as the acrolein class of compounds.

Examples of TADDOL-catalyzed Diels-Alder reactions of 1-amino-3-siloxy dienes with acroleins are shown in Table 5 below.

TABLE 5

TADDOL Catalyzed Diels-Alder Reactions of 1-Amino-3-Siloxy Dienes with Acroleins

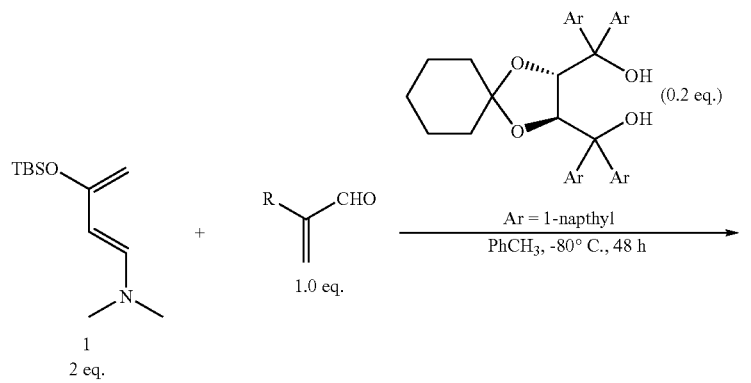

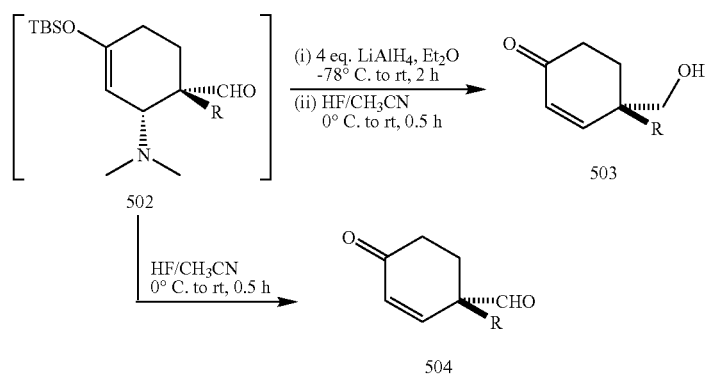

| Entry | R | yield of 504 (%) | yield of 503 (%) | ee of 503 (%) |
|---|---|---|---|---|
| 1 | H | a | 81 | 81 |
| 2 | Me | 87 | 85 | 93 |
| 3 | Et | 83 | 81 | 91 |
| 4 | $^i$Pr | 87 | 83 | 93 |
| 5 | Bn | 84 | 80 | 95 |
| 6 | $CH_2CH_2OTBS$ | 81 | 81 | 90 |

[a]Product was unstable: rapid decomposition upon removal of solvent at rt

It should be noted that while 1-amino-3-siloxybutadiene 1 is a presently preferred diene for use in accordance with the present invention, other less electron rich dienes, such as 1-amino dienes, also have been used and shown to work. Examples of the reaction between a 1-amino-diene with acroleins are shown in Table 6 below.

TABLE 6

TADDOL Catalyzed Diels-Alder Reactions of 1-Amino-Dienes with Acroleins

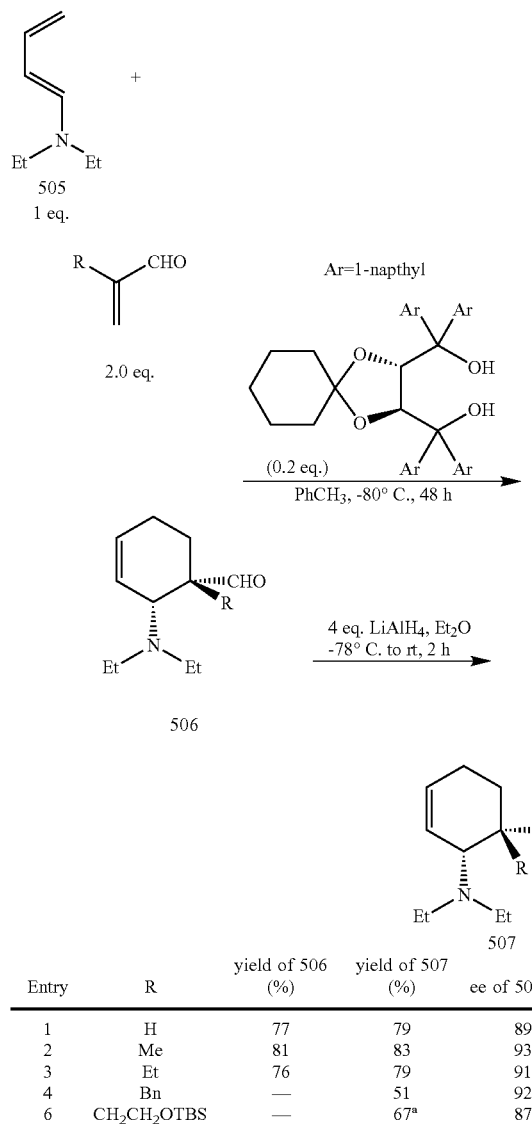

| Entry | R | yield of 506 (%) | yield of 507 (%) | ee of 507 (%) |
|---|---|---|---|---|
| 1 | H | 77 | 79 | 89 |
| 2 | Me | 81 | 83 | 93 |
| 3 | Et | 76 | 79 | 91 |
| 4 | Bn | — | 51 | 92 |
| 6 | $CH_2CH_2OTBS$ | — | 67[a] | 87 |

[a]Contaminated with Ca. 15% of a byproduct derived from 507.

In view of the very promising results of the 1-napthyl TADDOL-catalyzed Diels-Alder reaction of aminosiloxy diene 505, it is of interest to understand the mechanism and reactivity profile of this novel process. The gross structural features of the TADDOL class of ligands have been studied. At present, there are over 50 X-ray crystal structures of TADDOLs with a hydrogen bond acceptor (typically simple aliphatic alcohols, such as MeOH). All of the TADDOLs display $C_2$ symmetry with a propeller-type arrangement of the aryl rings. Unfortunately, there are no X-ray crystal structures of TADDOLs with an aldehyde. Results to date have suggested that the solvent plays an important role in the actual crystallization of the complex.

In the absence of structural data, molecular modeling studies have been conducted. A presently preferred model that accurately explains the activation of the dienophile and correctly predicts the absolute stereochemical outcome for the reaction of both aliphatic and aromatic aldehydes is shown in FIG. 9.

Without wishing to be bound by a particular theory or to in any way limit the scope of the appended claims or their equivalents, it is presently believed that the dienophile (benzaldehyde is shown) is activated through a two-point interaction. First, an intermolecular hydrogen bond between the hydrogen of one of the hydroxyl groups and the carbonyl provides the necessary lowering of the LUMO energy through a Lewis acid like mechanism. Second, the carbonyl double bond is located in proximity to the π system of one of the 1-napthyl rings and is stabilized through a π—π interaction, wherein one component is electron rich and the other component is electron poor.

Based on the above-described model, the aryl or alkyl substituent is positioned away from the naphthalene ring. This model suggests that the Si face of the aldehyde is accessible to the aminosiloxy diene and correctly predicts the absolute configuration of the obtained cycloadduct.

As is well known in the art, an elucidation of the true mechanism of the catalyzed reaction may be investigated by analyzing the kinetics and thermodynamics of the reaction. Rate constants and the orders of the reactants may be obtained by carefully monitoring the progress of the reaction by integration of the reactants and product signals in high field proton NMR experiments. Data taken at different reactant concentrations will determine the order of each reactant and the overall order of the reaction, thereby determining the overall rate law for this reaction. A similar process of monitoring the course of the reaction over a range of temperatures using variable temperature high field proton NMR would provide data to determine critical thermodynamic parameters ($E_a$, $\Delta H$, and $\Delta G$) of the reaction. Lastly, the possibility of aggregate or other complex behavior of the catalyst during the course of the reaction could be investigated through the presence of a non-linear relationship between the enantiomeric purity of the catalyst and that of the product (for example, see: Blackmond, D. G. "Description of the condition for asymmetric amplification in autocatalytic reactions," *Adv. Synth. Catal.*, 2002, 344, 156–158; Blackmond, D. G. "Kinetic Aspects of Nonlinear Effects in Asymmetric Catalysis," *Acc. Chem. Res.*, 2000, 33, 402–411; and Bolm, C. "Non-linear effects in enantioselective synthesis: asymmetric amplification," *Advanced Asymmetric Synthesis*, 1996, 9–26).

Tuning of the electronic and steric properties of TADDOLs is guided according to the above-described model for rationalizing the outcome of the 1-naphthyl TADDOL catalyzed HDA reactions. As noted above, this model highlights the importance of π-stacking in the TADDOL-aldehyde complex. This, in turn, suggests that fine tuning the electronic (and possibly steric) properties of the 1-naphthyl ring system would be desirable for the development of even more highly enantioselective catalysts.

By way of example, preferred modifications of the TADDOL skeleton include introducing electron-rich and/or electron-poor substituents, such as the 1-halo-naphthyl derivatives shown in FIG. 10. These may be synthesized according to well-established procedures and converted into the corresponding TADDOL ligands. All manner of chemical transformations known in the art—including but not limited to those described in treatises such as *Comprehensive Organic Transformations*, 2nd *Edition* by Richard C. Larock (Wiley-VCH, New York, 1999) and *March's Advanced Organic Chemistry*, 5th Edition by Michael B. Smith and Jerry March (John Wiley & Sons, Inc., 2001), and references cited therein, are contemplated for use in accordance with the present invention. The tuning of the electronic properties of the α-ring (i.e., the ring directly connected to the remaining part of TADDOL) (FIG. 10, 60) and/or the β-ring of the naphthyl system (61) would provide an indication of which of the two π systems is more important for increasing the enantioselectivity of the HDA reaction. To probe the importance of π stacking, fully saturated versions (e.g., a cyclohexane based motif) and partially saturated (e.g., cyclohexene-based motif) versions of TADDOL may be synthesized and tested.

Other preferred modifications to the TADDOL skeleton include structural modifications of the aryl rings. Strategic placement of methyl (or even bulkier aliphatic groups) around the 1-naphthyl ring system 62 may result in a better overall catalyst. Alternatively, it might be possible to simply use a phenyl-based catalyst appropriately substituted with aliphatic groups (63, 64). Two other derivatives that are presently preferred include the 1-anthracenyl and phenanthrenyl variants of TADDOL 65 and 66. As used herein, the term "derivative" is to be understood as referring to a chemical compound made from a parent compound by one or more chemical reactions.

Further preferred modifications to the TADDOL skeleton include changing the structure of the acetonide region of the molecule, shown in FIG. 11, which is presently believed to have an effect on the selectivity and efficiency of the catalysts.

Other catalysts in accordance with the present invention are based on chiral 1,2-diols, 1,4-diols, 1,3-diols, and 1,6-diols (e.g., binap-type compounds). $C_2$-Symmetrical diols with the possibility of π—π interactions are presently preferred. Other chiral diols embodying features of the present invention include the BINOL ligands and their derivatives and other tartrate-derived 1,4-diols. In addition, chiral amino alcohols (or di- and tripeptides) are also presently preferred templates for hydrogen bond donors.

In summary, alcohols have been discovered that promote HDA reactions of 1-amino-3-siloxybutadiene at much higher rates than other solvents. Hydrogen bonding is believed to be a primary reason for this unusual acceleration. Unactivated, simple ketones reacted readily with 1-amino-3-siloxydienes in 2-butanol to give dihydropyrans having a quaternary carbon. Moreover, it has been discovered that the hydrogen-bond strategy may be successfully extended to asymmetric catalysis. Successful hydrogen-bond catalyzed asymmetric reactions were developed using chiral TADDOLs. The reactions proceeded at low temperature, with good yields and with excellent ee demonstrating that hydrogen bonding by a simple chiral alcohol to a carbonyl group may accomplish what previously had been considered the domain of chiral metal-based Lewis acids. Catalytic amounts of chiral TADDOL were used to demonstrate the catalytic nature of the reaction. Furthermore, it has been discovered that the TADDOL-type catalysts are not limited to the catalysis of HDA reactions but rather are also useful for the catalysis of traditional (i.e., non-hetero) Diels-Alder cycloadditions with dienophiles such as α,β-unsaturated carbonyl compounds.

Asymmetric Catalysis of the Alkynylation of Aldehydes

It has further been discovered that the above-described catalysts are not limited to the catalysis of cycloaddition reactions but are also useful for the catalysis of a variety of non-cycloaddition asymmetric reactions including but not limited to 1,2-addition reactions to carbonyl compounds. A presently preferred 1,2-addition reaction for use in accordance with the present invention is the alkynylation of aldehydes.

A presently preferred class of catalysts for performing asymmetric alkynylations of aldehydes in accordance with the present invention is the TADDOL family of catalysts described above. Table 7 below shows data for enantioselective alkynylation of aldehydes in accordance with the present invention.

TABLE 7

Enantioselective Alkynylation of Aldehydes

| Equiv. of TADDOL | solvent | temp (° C.) | yield (%) | ee (%) |
|---|---|---|---|---|
| 0.1 | PhCH₃ | rt | 76 | 13 |
| 0.2 | PhCH₃ | rt | 77 | 15 |
| 0.1 | PhCH₃ | −10 | 79 | 16 |
| 0.1 | THF | rt | <40% conversion | — |

The following examples and representative procedures illustrate features in accordance with the present invention, and are provided solely by way of illustration. They are not intended to limit the scope of the appended claims or their equivalents.

EXAMPLES

General Procedure for HDA Reactions Shown in Table 3

General: All reactions were carried out under a nitrogen atmosphere. Common solvents were purified before use. Tetrahydrofuran (THF) and diethyl ether ($Et_2O$) were purified by distillation from potassium-benzophenone ketyl. Other solvents were freshly distilled from calcium hydride prior to use. All commercial chemicals were reagent grade and purified as necessary. KHMDS was used from newly opened 100 mL bottles, purchased from Aldrich, Inc. Reactions were monitored by thin layer chromatography (TLC) using 250 mm Whatman precoated silica gel plates. Flash column chromatography was performed over Fisher or EM Science Laboratories silica gel (230–400 mesh). Melting points were measured on a Thomas Hoover capillary melting point apparatus and are uncorrected. Carbon and proton NMR spectra were recorded on Bruker DRX-500 spectrometer. $^1H$ NMR chemical shifts are reported as δ values (ppm)

relative to internal tetramethylsilane and splitting patterns are designated as: s=singlet, d=doublet, t=triplet, q=quartet, m=multiplet, br=broad. Coupling constants are given in hertz (Hz).

Materials: N,N-dimethyl-1-amino-3-'Butyldimethylsilyloxy-1,3-butadiene was prepared according to our published procedures and redistilled prior to use. For example, see: (a) Kozmin, S. A.; Janey, J. M.; Rawal. V. H. *J. Org. Chem.* 1999, 64, 3039 and (b) Kozmin, S. A.; He, S.; Rawal, V. H. *Org. Synth.* 2000, 78, 152–159; ibid, p160. Ketones were purchased from Aldrich, Inc. and freshly distilled or recrystallized prior to use. Acetyl chloride was purchased from Aldrich, Inc. and freshly distilled from N,N-dimethylaniline prior to use. Anhydrous grade 2-butanol was purchased from Aldrich, Inc. and freshly distilled from calcium hydride prior to use.

Procedure: To a 10 mL oven-dried flask was added (1.0 mmol, 2.0 eq.) ketone and 0.5 mL 2-butanol. Diene 1 (114 mg, 0.5 mmol, 1.0 eq.) was then added slowly at room temperature. The reaction mixture was stirred until diene was fully consumed (NMR). The solvent was removed in vacuo and the residue was redissolved in 4 mL of ether. The pale yellow solution was cooled to −78° C., and 43 μL acetyl chloride (0.6 mmol, 1.2 eq.) in 1 mL ether was added slowly. The mixture was stirred at −78° C. for ca. 10 min and quenched with 5 mL saturated sodium bicarbonate solution. The organic layer was separated, and the aqueous phase extracted twice with ether. The combined organic phase was dried with magnesium sulfate, filtered, and concentrated. The yellow residue was purified by flash chromatography to afford the desired spirodihydropyrone compounds 6.

Figure 12:
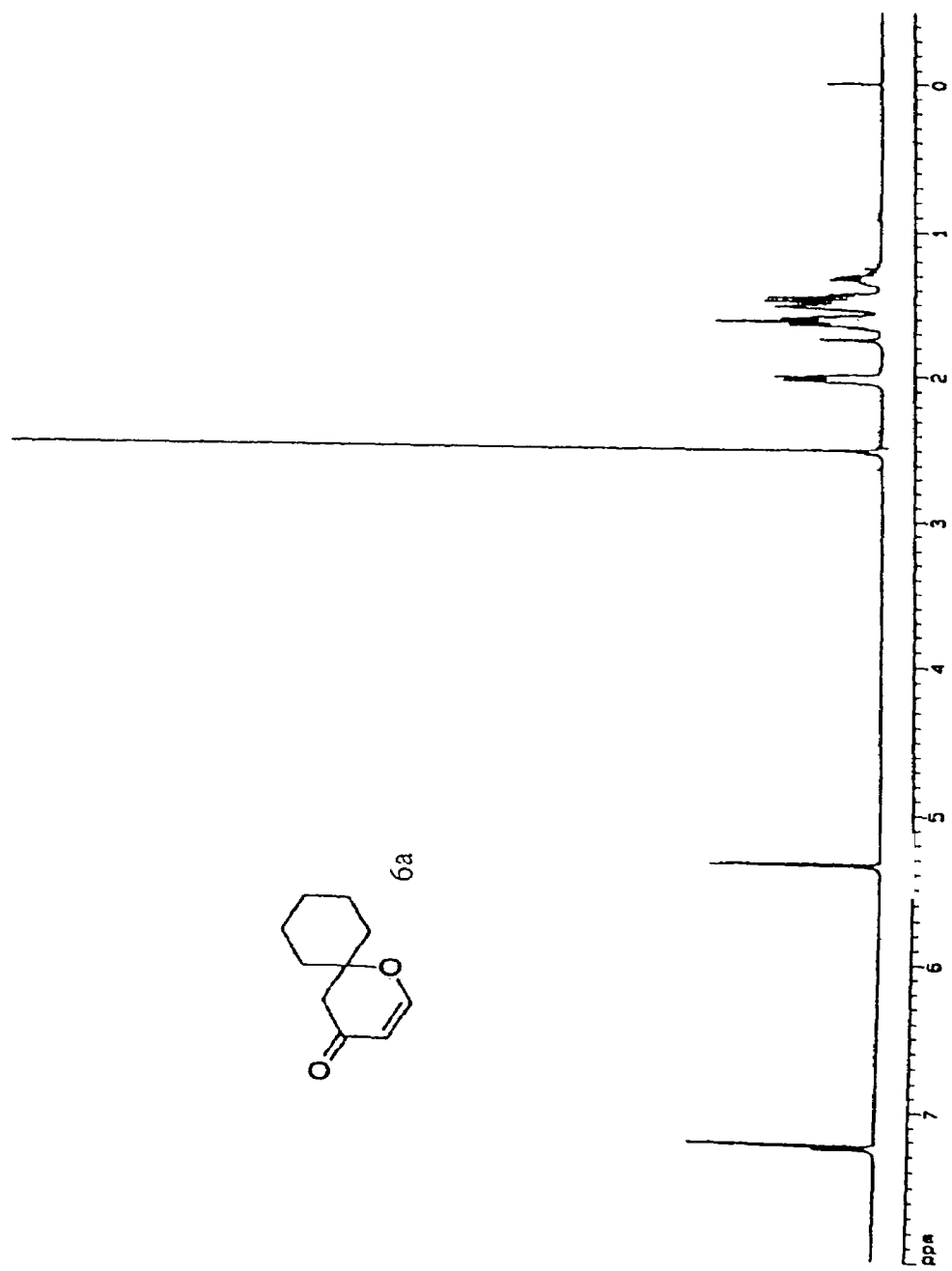
Figure 13:
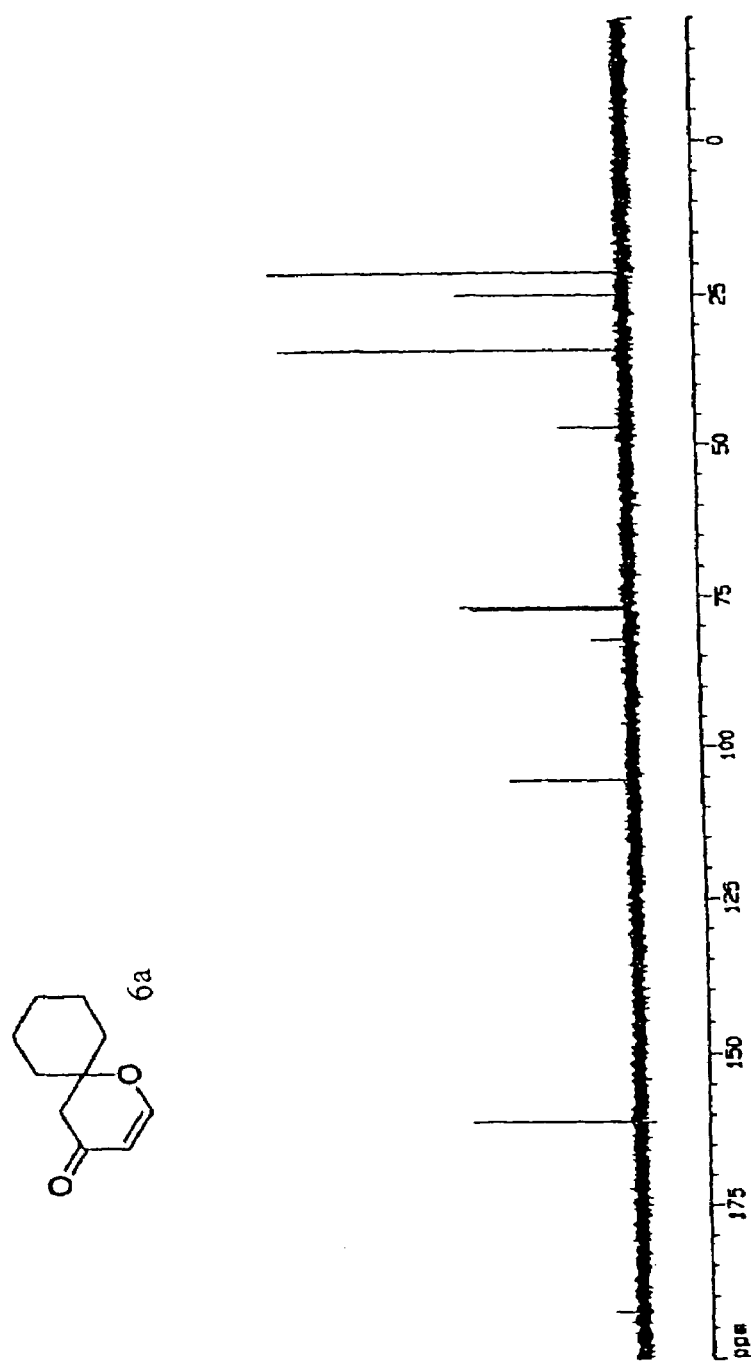

6a (1-oxaspiro[5,5]undec-2-en-4-one): Flash chromatography on silica gel (10% ethylacetate/hexane) gave 65 mg (78%) of 6a, a light yellow oil. $^1$H NMR (500 MHz, CDCl$_3$, ppm) δ 7.25 (d, J=6 Hz, 1 H), 5.35 (d, J=6 Hz, 1 H), 2.50 (s, 2H), 2.02 (br d, J=13 Hz, 2 H), 1.50 (m, 8H). $^{13}$C NMR (125 MHz, CDCl$_3$, ppm) δ 192.4, 161.1, 105.6, 82.3, 47.2, 34.2, 25.0, 21.4. FIGS. 12 and 13 show the $^1$H NMR spectrum and $^{13}$C NMR spectrum, respectively, of spiro-dihydropyrone 6a.

Figure 15:
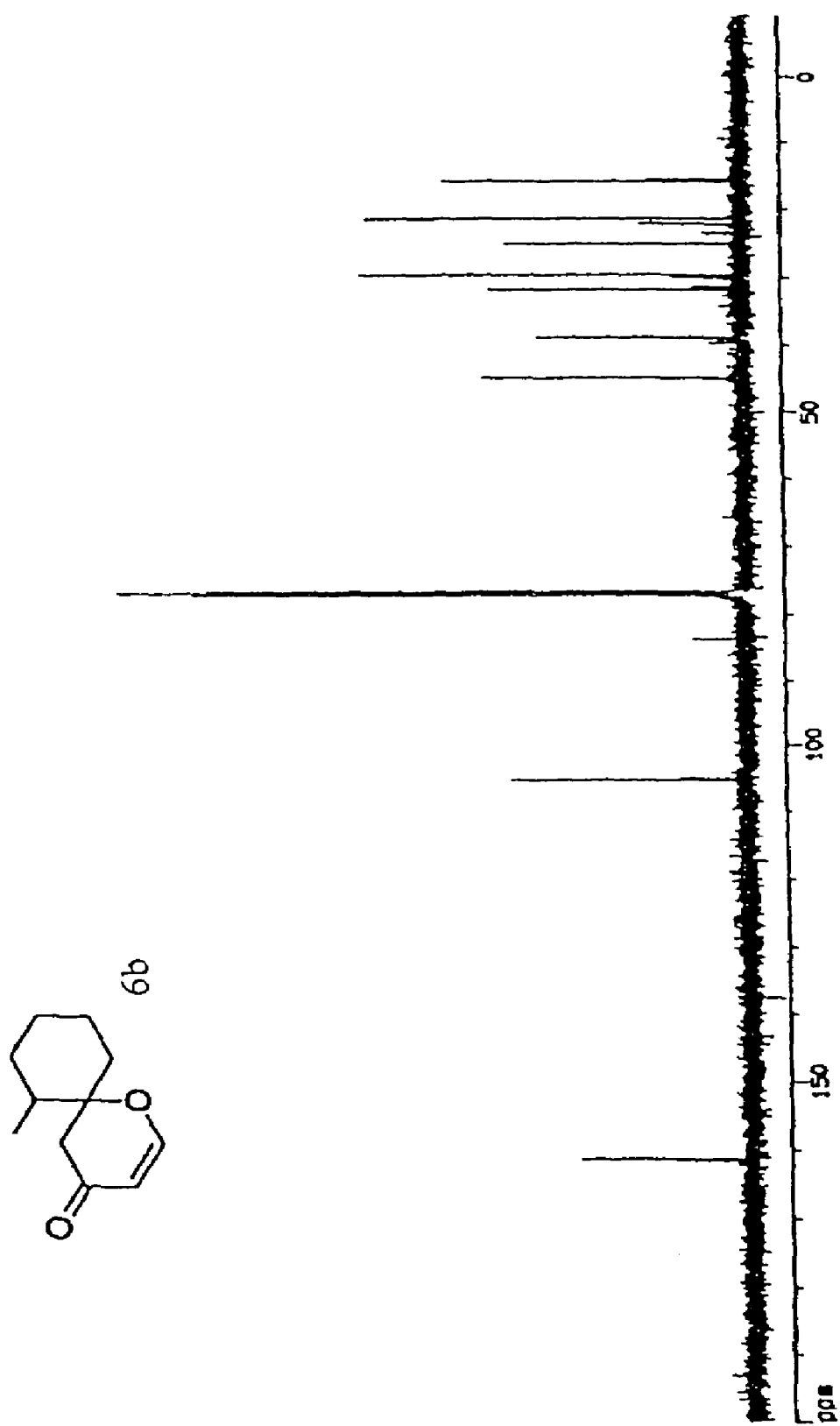
FIG. 15 shows a $^{13}$C NMR spectrum of spiro-dihydropyrone 6b.

6b (6-methyl-1-oxaspiro[5,5]undec-2-en-4-one): Flash column on silica gel (25% ether/hexane) gave 32 mg (35%) of 6d, a light yellow oil. NMR showed that the product was a mixture of diastereomers (3.3:1). FIGS. 14 and 15 show the $^1$H NMR spectrum and $^{13}$C NMR spectrum, respectively, of spiro-dihydropyrone 6b.

Major isomer: $^1$H NMR (400 MHz, CDCl$_3$, ppm) δ 7.27 (d, J=6 Hz, 1 H), 5.34 (d, J=6 Hz, 1 H), 2.98 (d, J=16 Hz, 1 H), 2.19 (br d, J=15 Hz, 1 H), 2.10 (d, J=16 Hz, 1 H), 1.40 (m, 8 H), 1.00 (d, J=6 Hz, 3H) $^{13}$C NMR (100 MHz, CDCl$_3$, ppm) δ 193.0, 161.3, 105.4, 82.9, 44.9, 38.9, 31.8, 29.6, 25.1, 21.4, 15.8.

Minor isomer: $^1$H NMR (400 MHz, CDCl$_3$, ppm) δ 7.26 (d, J=6 Hz, 1 H), 5.33 (d, J=6 Hz, 1 H), 2.66 (d, J=16 Hz, 1 H), 2.45 (br d, J=15 Hz, 1 H), 1.95 (d, J=16 Hz, 1 H), 1.40 (m, 8 H), 1.00 (d, J=6 Hz, 3H) $^{13}$C NMR (100 MHz, CDCl$_3$, ppm) δ 192.5, 161.5, 105.2, 77.3, 39.7, 39.2, 31.3, 30.1, 23.5, 22.2, 15.5.

Figure 16:
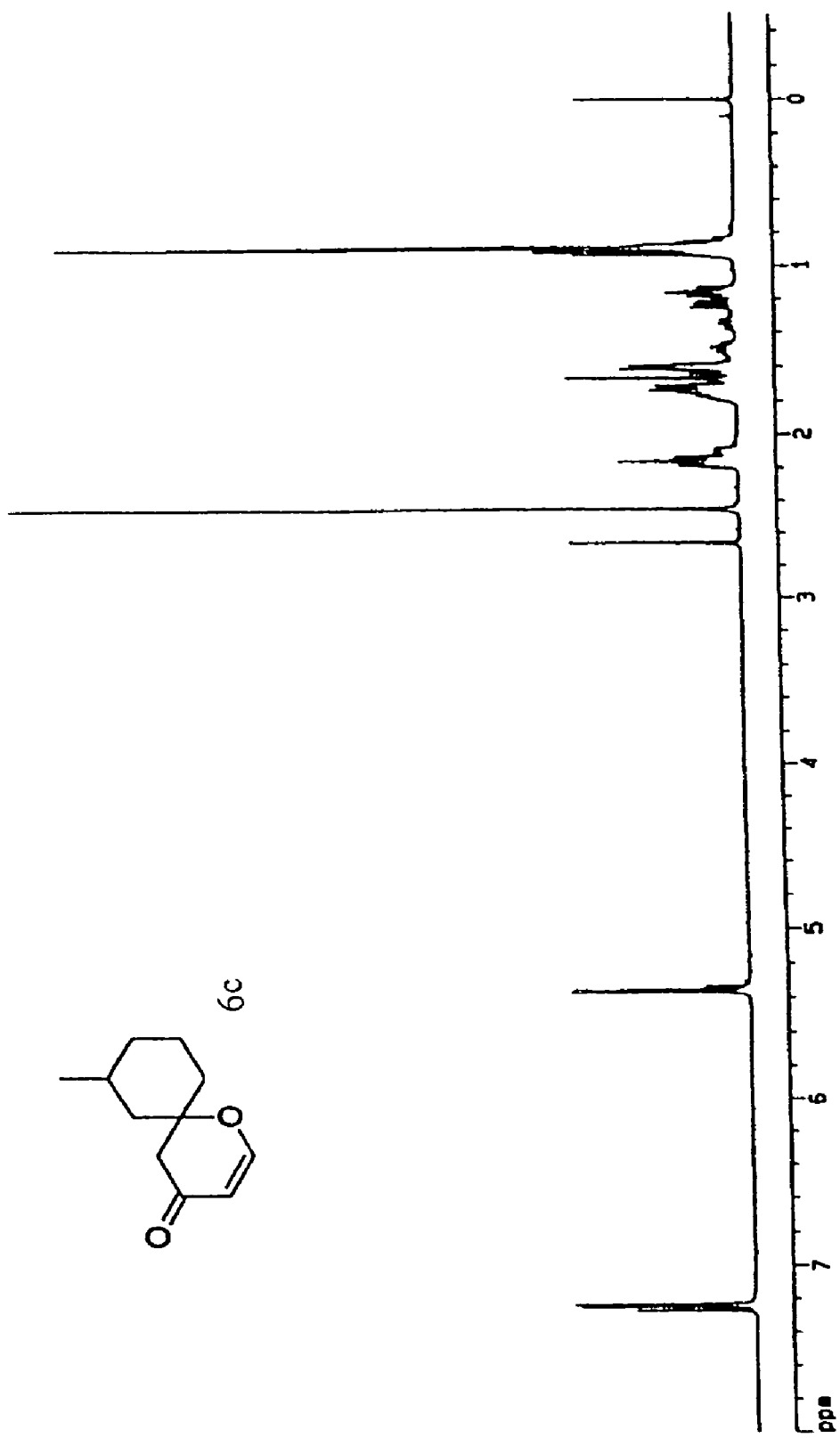
FIG. 16 shows a $^1$H NMR spectrum of spiro-dihydropyrone 6c.
Figure 17:
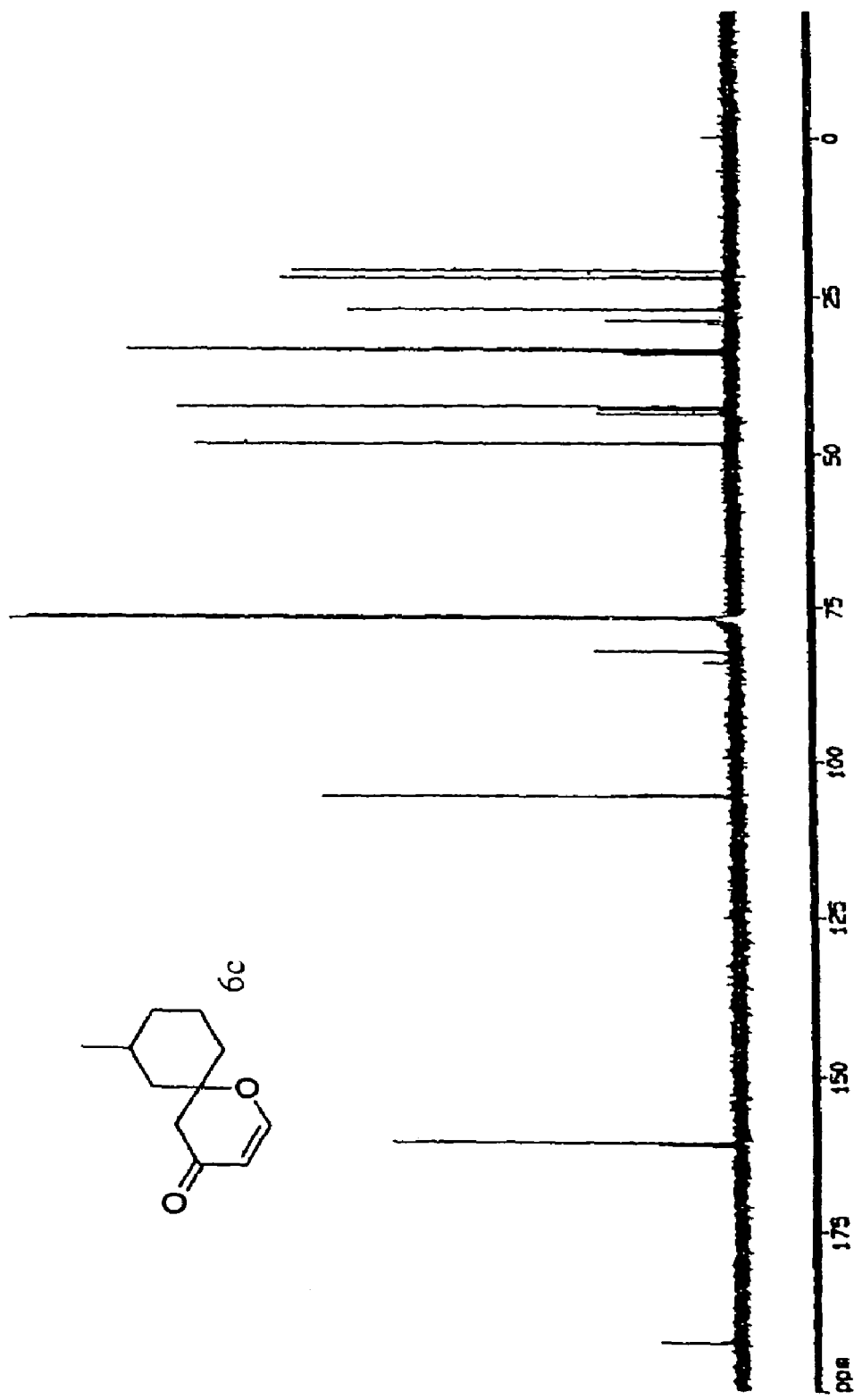
FIG. 17 shows a $^{13}$C NMR spectrum of spiro-dihydropyrone 6c.

6c (7-methyl-1-oxaspiro[5,5]undec-2-en-4-one): Flash column on silica gel (7% and 12% ethylacetate/hexane) gave 68 mg (75%) of 6d as a pale yellow oil. NMR showed that the product was a 4.2:1 mixture of diastereomers. FIGS. 16 and 17 show the $^1$H NMR spectrum and $^{13}$C NMR spectrum, respectively, of spiro-dihydropyrone 6c.

Major isomer: $^1$H NMR (500 MHz, CDCl$_3$, ppm) δ 7.24 (d, J=6 Hz, 1 H), 5.36 (d, J=6 Hz, 1 H), 2.46 (s, 2 H), 2.15 (m, 2 H), 1.76 (m, 2 H), 1.62 (m, 2 H), 1.20 (m, 1 H), 0.90 (d, J=6 Hz, 3 H), 0.89 (m, 2H). $^{13}$C NMR (125 MHz, CDCl$_3$, ppm) δ 192.5, 161.1, 105.7, 82.4, 48.5, 42.6, 33.8, 33.5, 27.3, 22.2, 20.9.

Minor isomer: $^1$H NMR (500 MHz, CDCl$_3$, ppm) δ 7.23 (d, J=6 Hz, 1 H), 5.34 (d, J=6 Hz, 1 H), 2.66 (s, 2 H), 2.05 (m, 2 H), 1.50 (m, 5 H), 0.93 (d, J=6 Hz, 3 H), 0.91 (m, 2H). $^{13}$C NMR (125 MHz, CDCl$_3$, ppm) δ 192.2, 161.5, 105.4, 84.2, 43.7, 43.0, 34.4, 34.0, 29.0, 22.2, 22.0.

Figure 18:
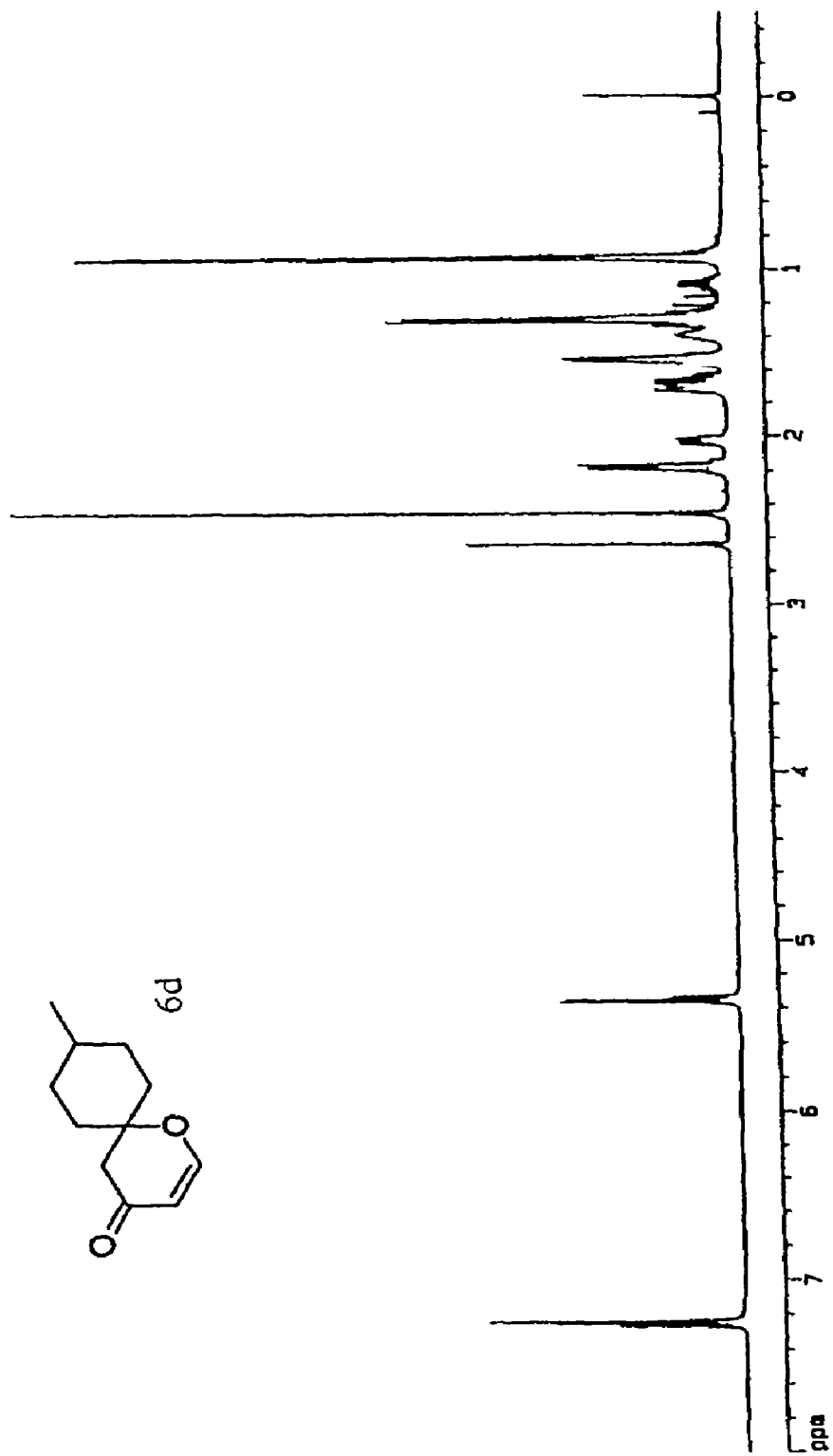
FIG. 18 shows a $^1$H NMR spectrum of spiro-dihydropyrone 6d.
Figure 19:
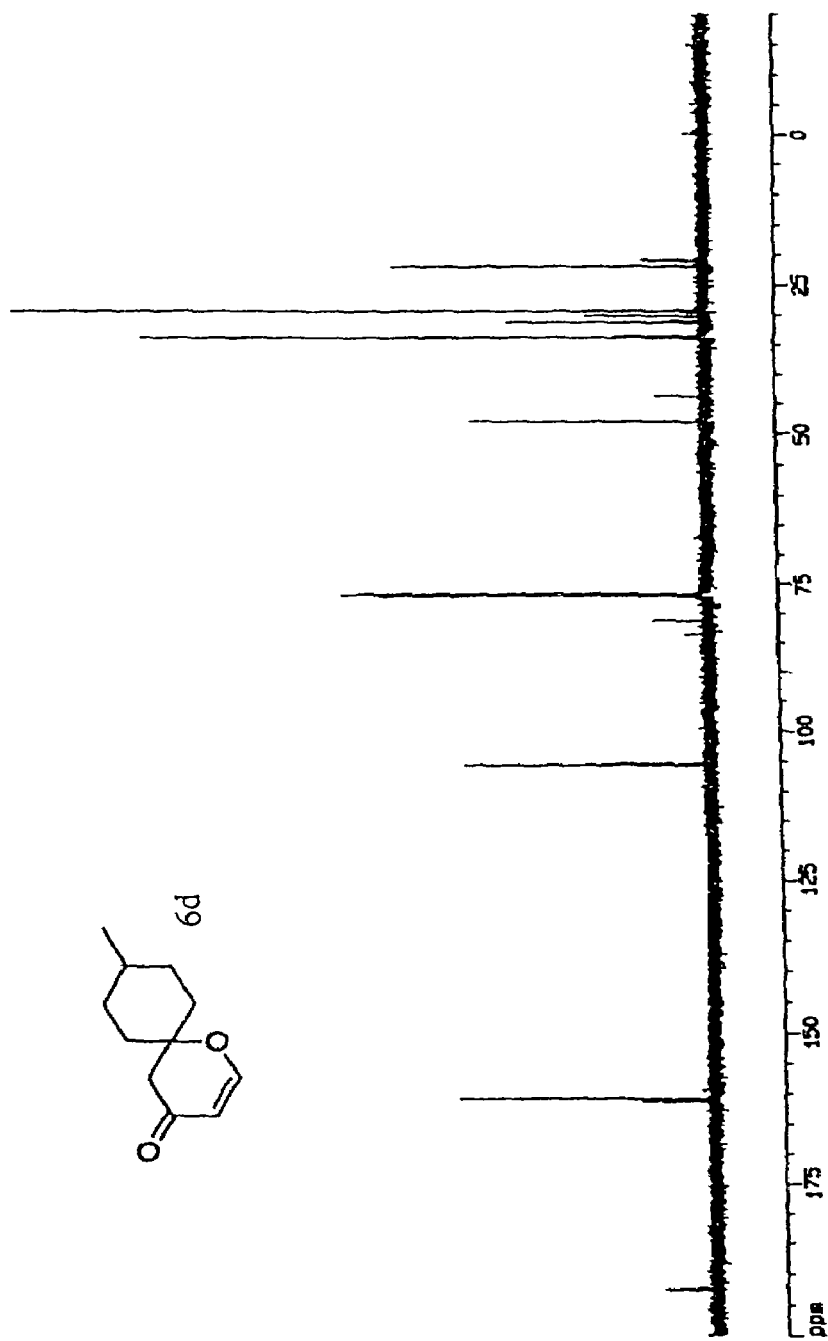
FIG. 19 shows a $^{13}$C NMR spectrum of spiro-dihydropyrone 6d.

6d (8-methyl-1-oxaspiro[5,5]undec-2-en-4-one): Flash column on silica gel (8% and 12% ethylacetate/hexane) gave 67 mg (74%) of 6d as light yellow oil. NMR showed that the product was a 2.8:1 mixture of diastereomers. FIGS. 18 and 19 show the $^1$H NMR spectrum and $^{13}$C NMR spectrum, respectively, of spiro-dihydropyrone 6d.

Major isomer: $^1$H NMR (500 MHz, CDCl$_3$, ppm) δ 7.25 (d, J=6 Hz, 1 H), 5.36 (d, J=6 Hz, 1 H), 2.45 (s, 2 H), 2.18 (m, 2 H), 1.70 (m, 1 H), 1.54 (m, 2 H), 1.31 (m, 4 H), 0.94 (d, J=6 Hz, 3H). $^{13}$C NMR (125 MHz, CDCl$_3$, ppm) δ 192.5, 161.0, 105.7, 81.4, 48.2, 33.9, 31.4, 29.5, 22.1.

Minor isomer: $^1$H NMR (500 MHz, CDCl$_3$, ppm) δ 7.24 (d, J=6 Hz, 1 H), 5.34 (d, J=6 Hz, 1 H), 2.64 (s, 2 H), 2.02 (m, 2 H), 1.40 (m, 7 H), 0.93 (d, J=6 Hz, 3H). $^{13}$C NMR (125 MHz, CDCl$_3$, ppm) δ 192.2, 161.5, 105.5, 83.6, 43.8, 33.7, 31.1, 30.3, 20.9.

Figure 20:
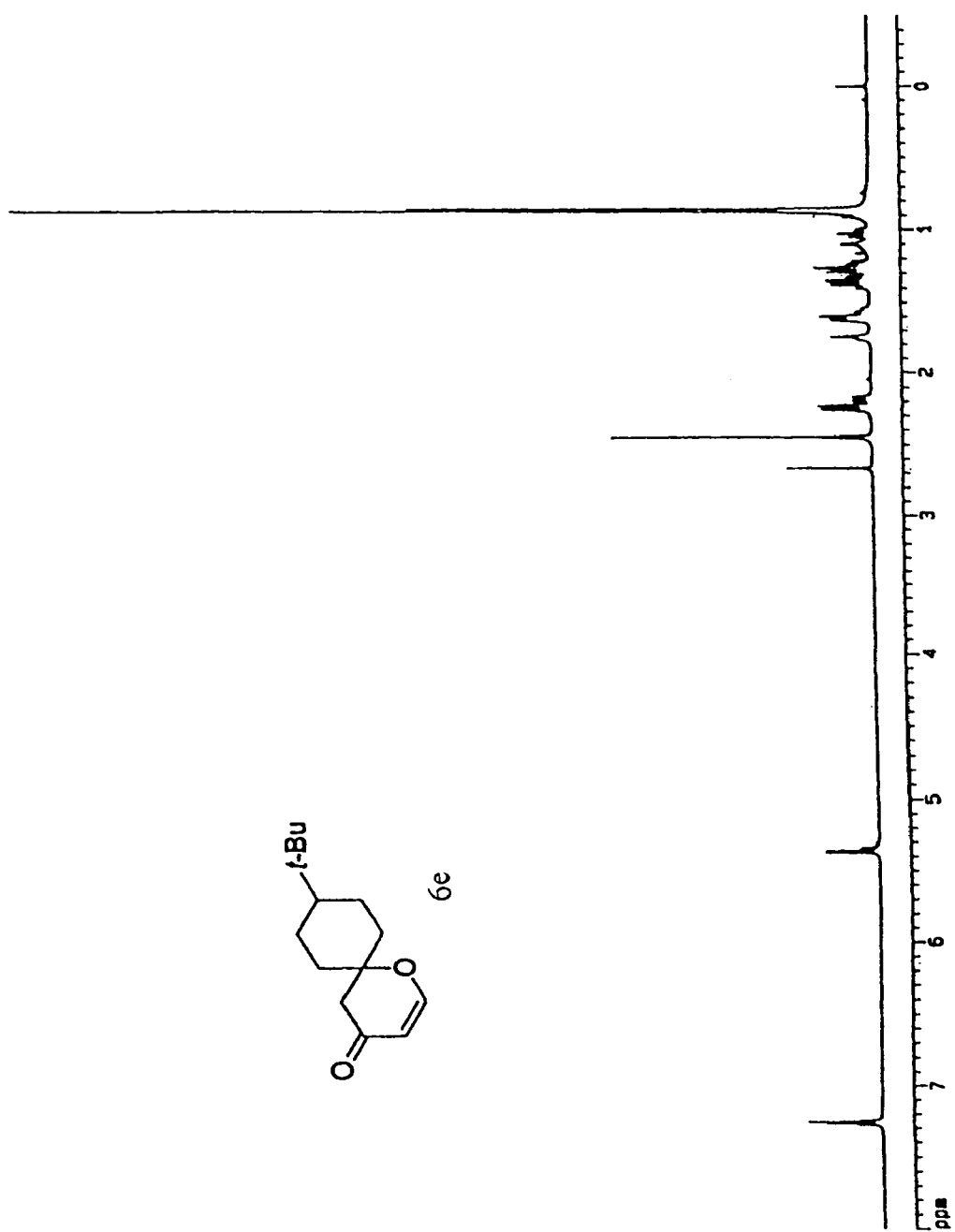
FIG. 20 shows a $^1$H NMR spectrum of spiro-dihydropyrone 6e.
Figure 21:
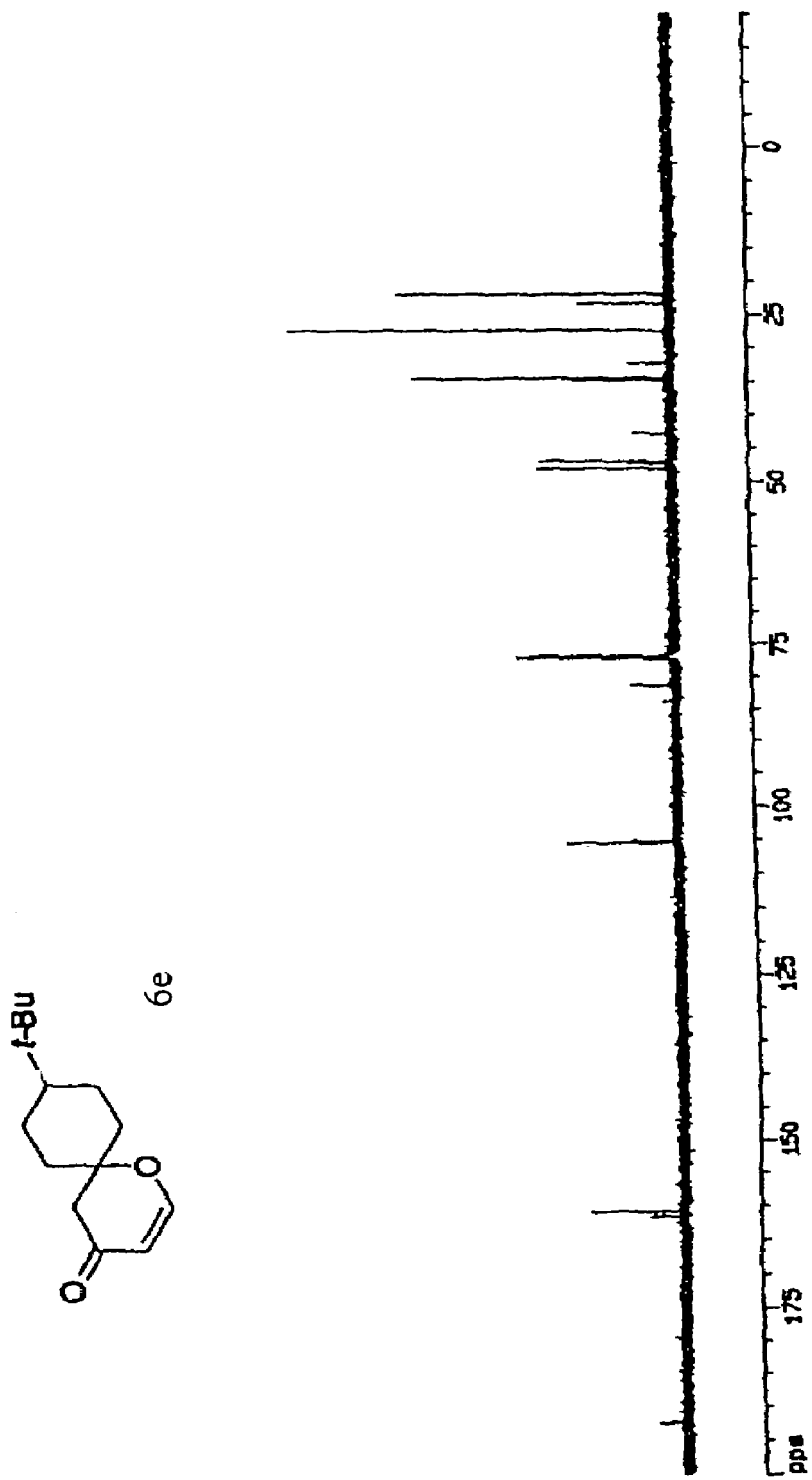
FIG. 21 shows a $^{13}$C NMR spectrum of spiro-dihydropyrone 6e.

6e (8-'Butyl-1-oxaspiro[5,5]undec-2-en-4-one): Flash column on silica gel (5% and 10% ethylacetate/hexane) gave 85 mg (74%) of product 6e as white solid. NMR showed that the product was a mixture of diastereomers (3:1). FIGS. 20 and 21 show the $^1$H NMR spectrum and $^{13}$C NMR spectrum, respectively, of spiro-dihydropyrone 6e.

Major isomer: $^1$H NMR (500 MHz, CDCl$_3$, ppm) δ 7.26 (d, J=6 Hz, 1 H), 5.37 (d, J=6 Hz, 1 H), 2.45 (s, 2 H), 2.25 (br d, J=14 Hz, 2 H), 1.61 (m, 2 H), 1.37 (m, 2 H), 1.27 (m, 2 H), 1.03 (m, 1 H), 0.87 (s, 9H). $^{13}$C NMR (125 MHz, CDCl$_3$, ppm) δ 192.6, 161.1, 105.7, 81.4, 48.2, 47.0, 34.5, 32.3, 27.5, 21.9.

Minor isomer: $^1$H NMR (500 MHz, CDCl$_3$, ppm) δ 7.26 (d, J=6 Hz, 1 H), 5.34 (d, J=6 Hz, 1 H), 2.66 (s, 2 H), 2.18 (br d, J=12 Hz, 2 H), 1.40 (m, 7 H), 0.86 (s, 9H). $^{13}$C NMR (125 MHz, CDCl$_3$, ppm) δ 192.7, 161.7, 105.4, 83.9, 47.4, 42.9, 34.9, 32.2, 27.5, 23.3.

Figure 22:
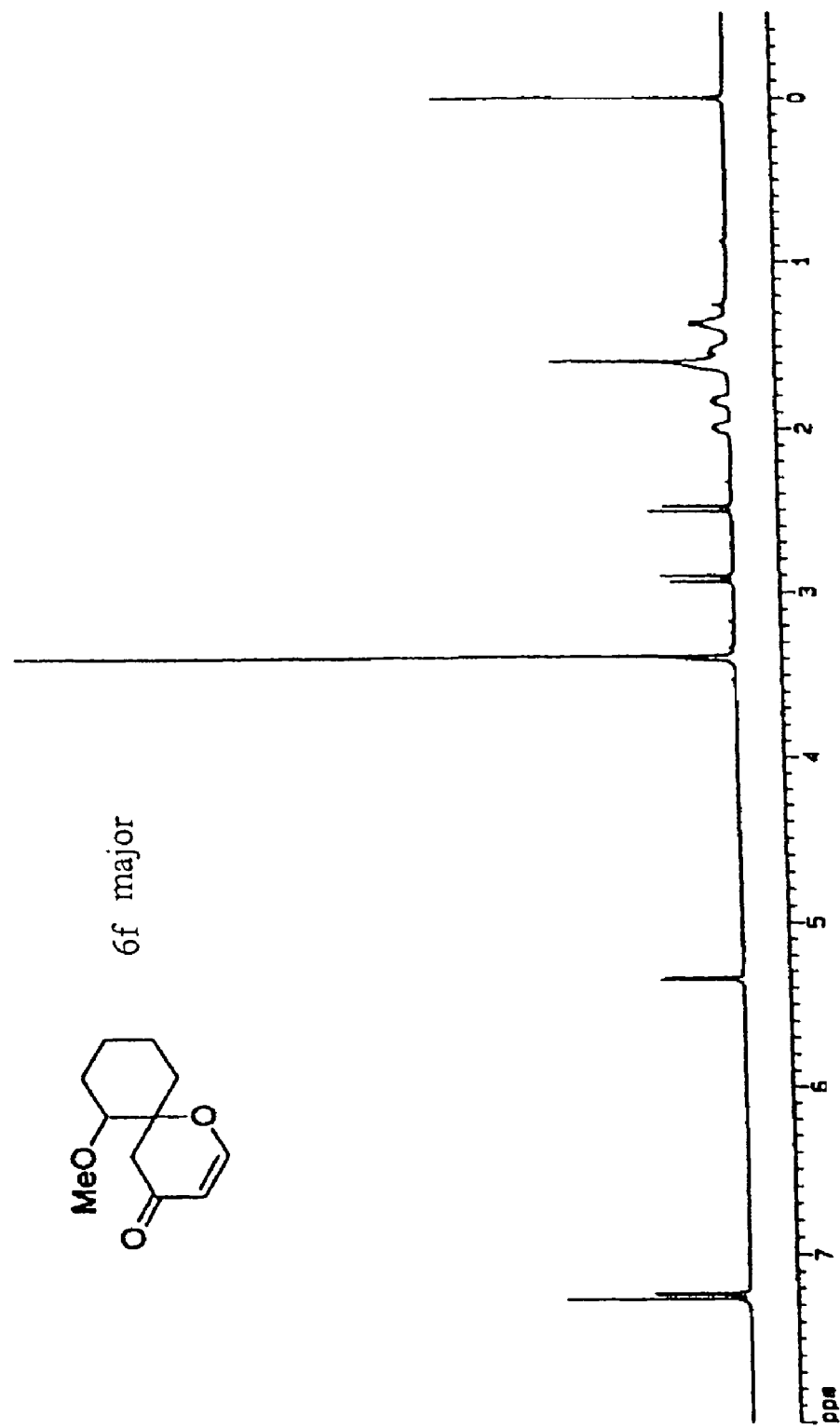
FIG. 22 shows a $^1$H NMR spectrum of a major isomer of spiro-dihydropyrone 6f.
Figure 23:
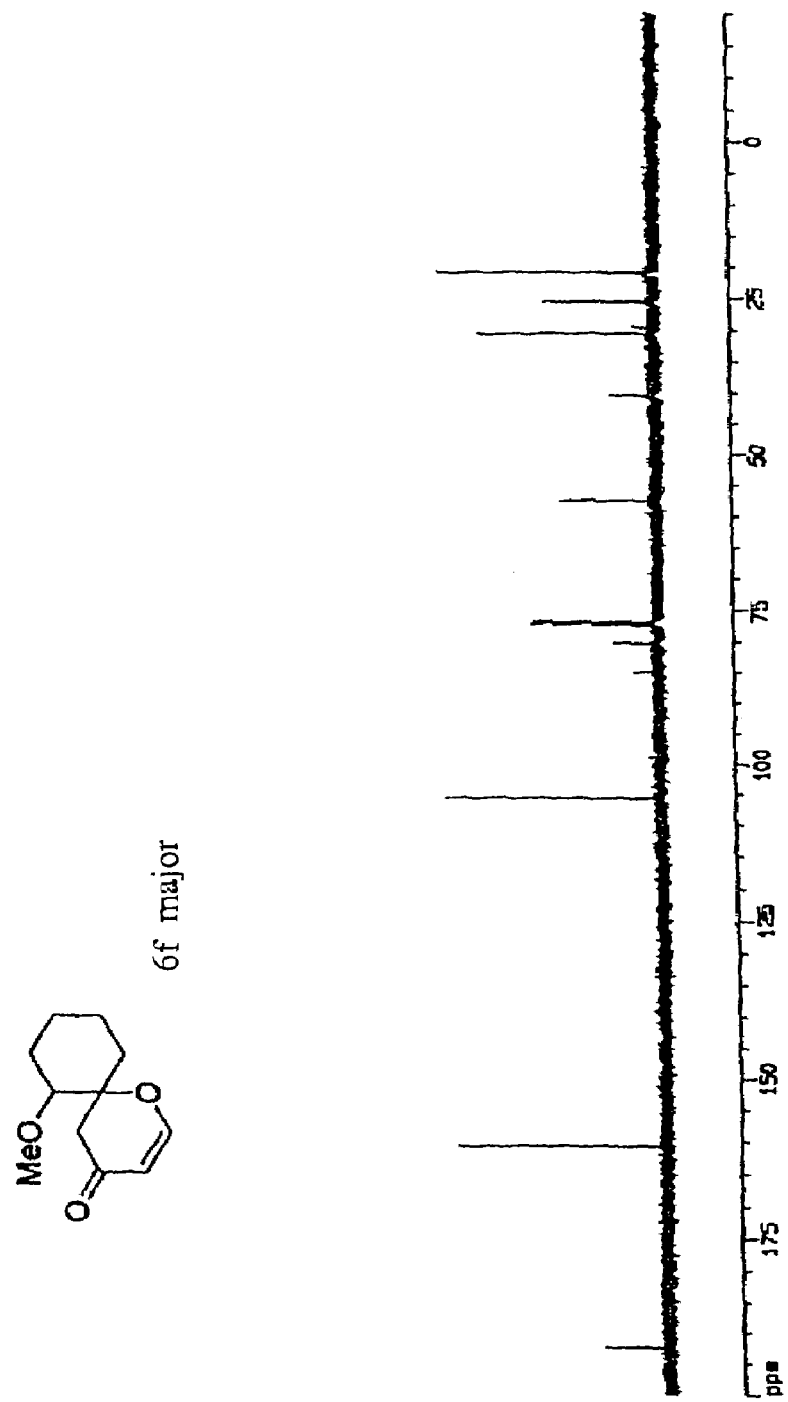
FIG. 23 shows a $^{13}$C NMR spectrum of a major spiro-dihydropyrone 6f.
Figure 24:
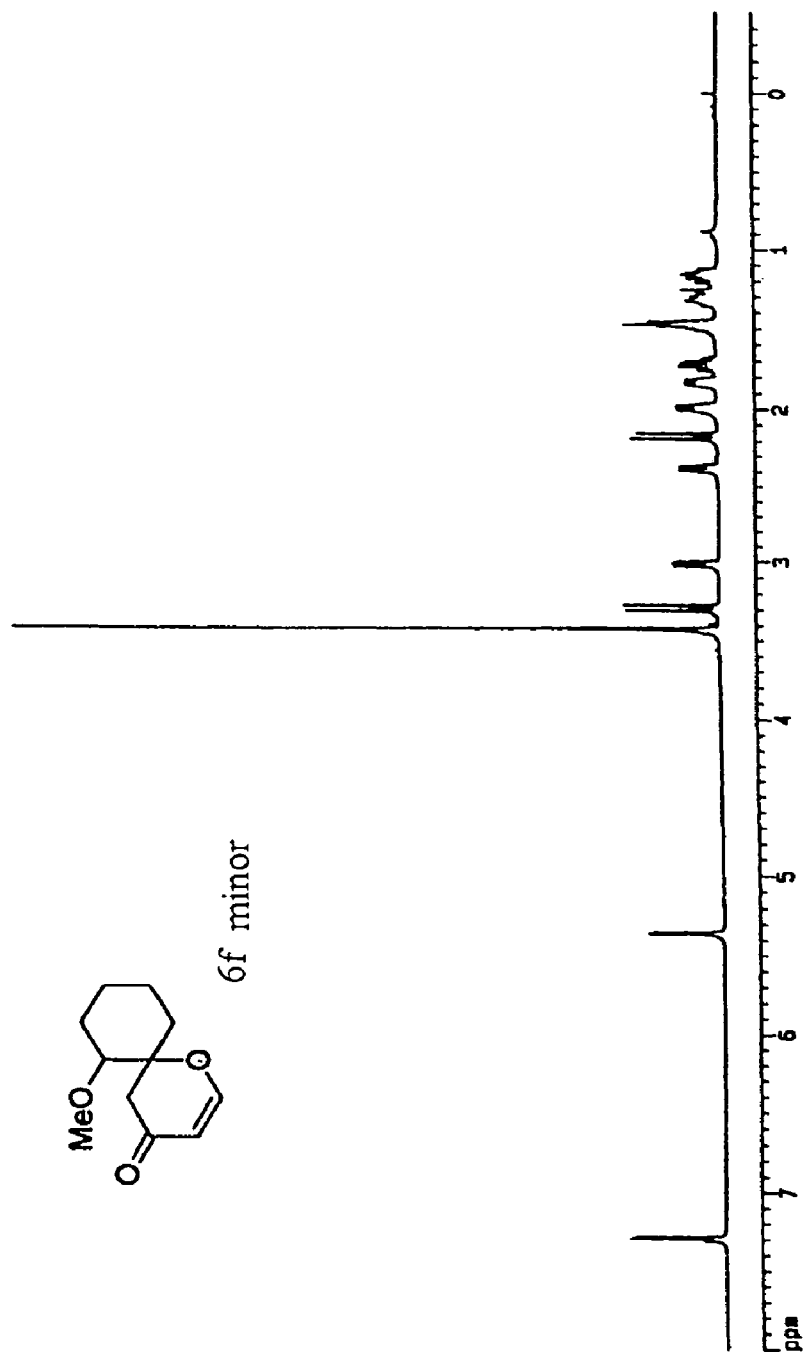
FIG. 24 shows a $^1$H NMR spectrum of a minor isomer of spiro-dihydropyrone 6f.
Figure 25:
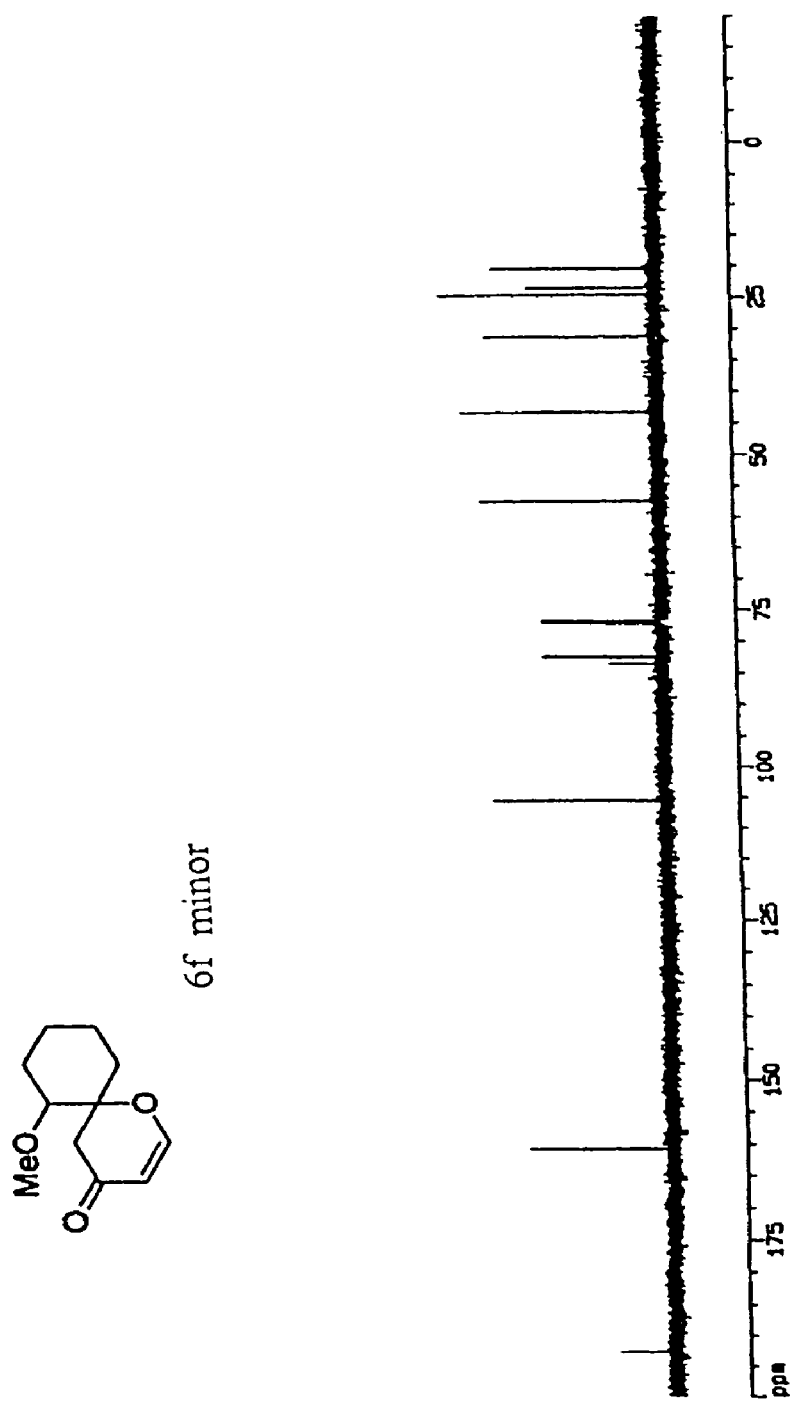
FIG. 25 shows a $^{13}$C NMR spectrum of a minor spiro-dihydropyrone 6f.

6f (6-methoxy-1-oxaspiro[5,5]undec-2-en-4-one): Flash column on silica gel (20% and 40% ethylacetate/hexane) gave 6f, as a 1.5:1 mixture of diastereomers (80 mg combined, 81%), both colorless oils. FIGS. 22 and 23 show the $^1$H NMR spectrum and $^{13}$C NMR spectrum, respectively, of the major isomer of spiro-dihydropyrone 6f. FIGS. 24 and 25 show the $^1$H NMR spectrum and $^{13}$C NMR spectrum, respectively, of the minor isomer of spiro-dihydropyrone 6f.

Major isomer: $^1$H NMR (500 MHz, CDCl$_3$, ppm) δ 7.23 (d, J=6 Hz, 1 H), 5.35 (d, J=6 Hz, 1 H), 3.40 (t, J=4 Hz, 1 H), 3.39 (s, 3 H), 2.92 (d, J=17 Hz, 1 H), 2.49 (d, J=17 Hz, 1 H), 2.00 (m, 1 H), 1.82 (m, 1 H), 1.59 (m, 4 H), 1.37 (m, 2H). $^{13}$C NMR (125 MHz, CDCl$_3$, ppm) δ 192.5, 160.8, 105.6, 84.9, 80.2, 57.6, 40.4, 30.6, 25.7, 21.2, 21.0.

Minor isomer: $^1$H NMR (500 MHz, CDCl$_3$, ppm) δ 7.29 (d, J=6 Hz, 1 H), 5.35 (d, J=6 Hz, 1 H), 3.42 (s, 3 H), 3.28 (d, J=13.5 Hz, 3 H), 3.01 (dd, J=11, 4 Hz, 1 H), 2.37 (br d, J=14 Hz, 1 H), 2.17 (d, J=13.5 Hz, 1 H), 1.98 (dq, J=13, 4 Hz, 1 H), 1.83 (m, 1 H), 1.72 (qd, J=11, 4 Hz, 1H). 1.47 (m, 2 H), 1.32 (m, 1 H), 1.16 (m, 1H). $^{13}$C NMR (125 MHz, CDCl$_3$, ppm) δ 192.7, 160.8, 105.5, 83.5, 82.5, 57.4, 43.3, 31.2, 24.6, 23.5, 20.4.

Figure 26:
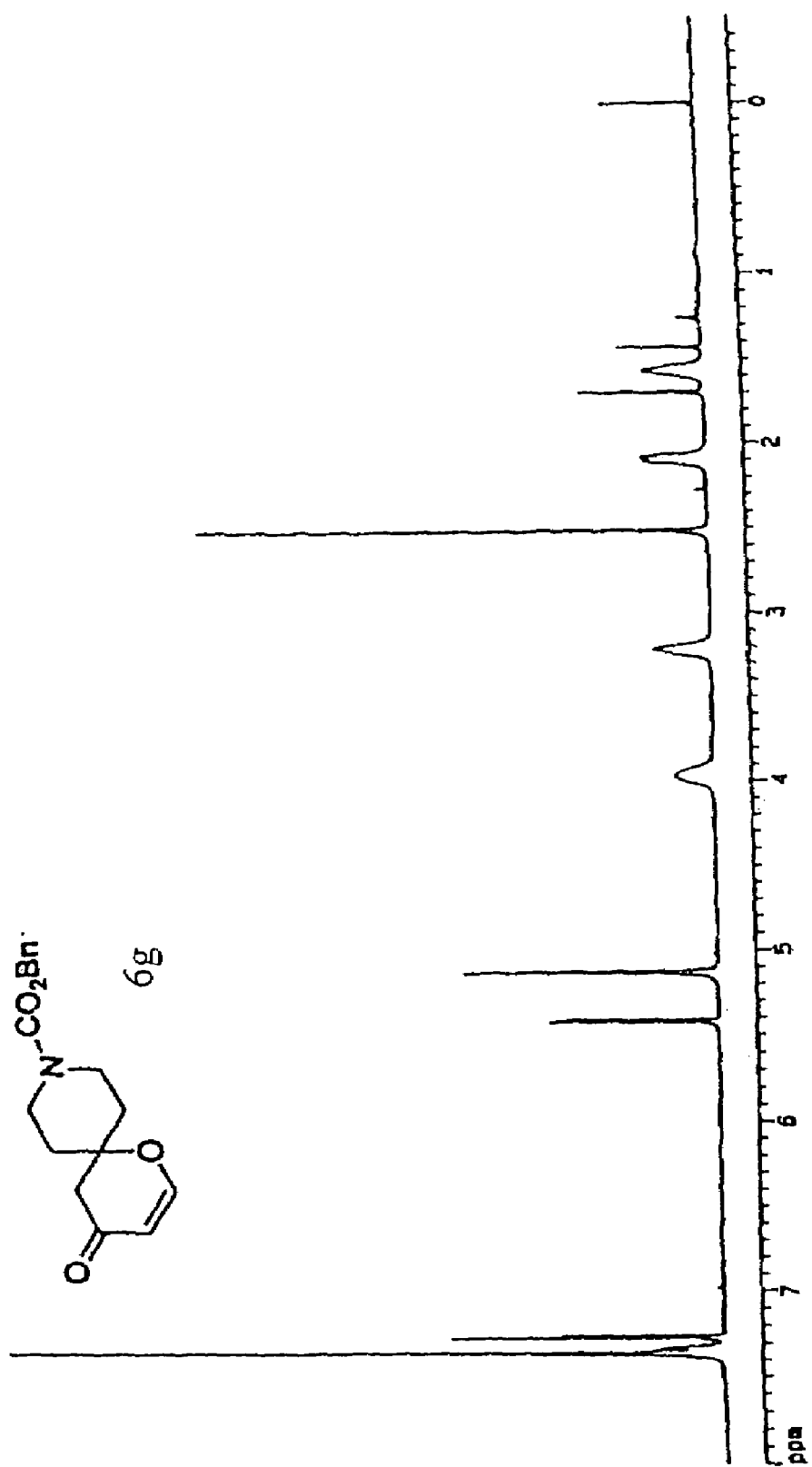
FIG. 26 shows a $^1$H NMR spectrum of spiro-dihydropyrone 6g.
Figure 27:
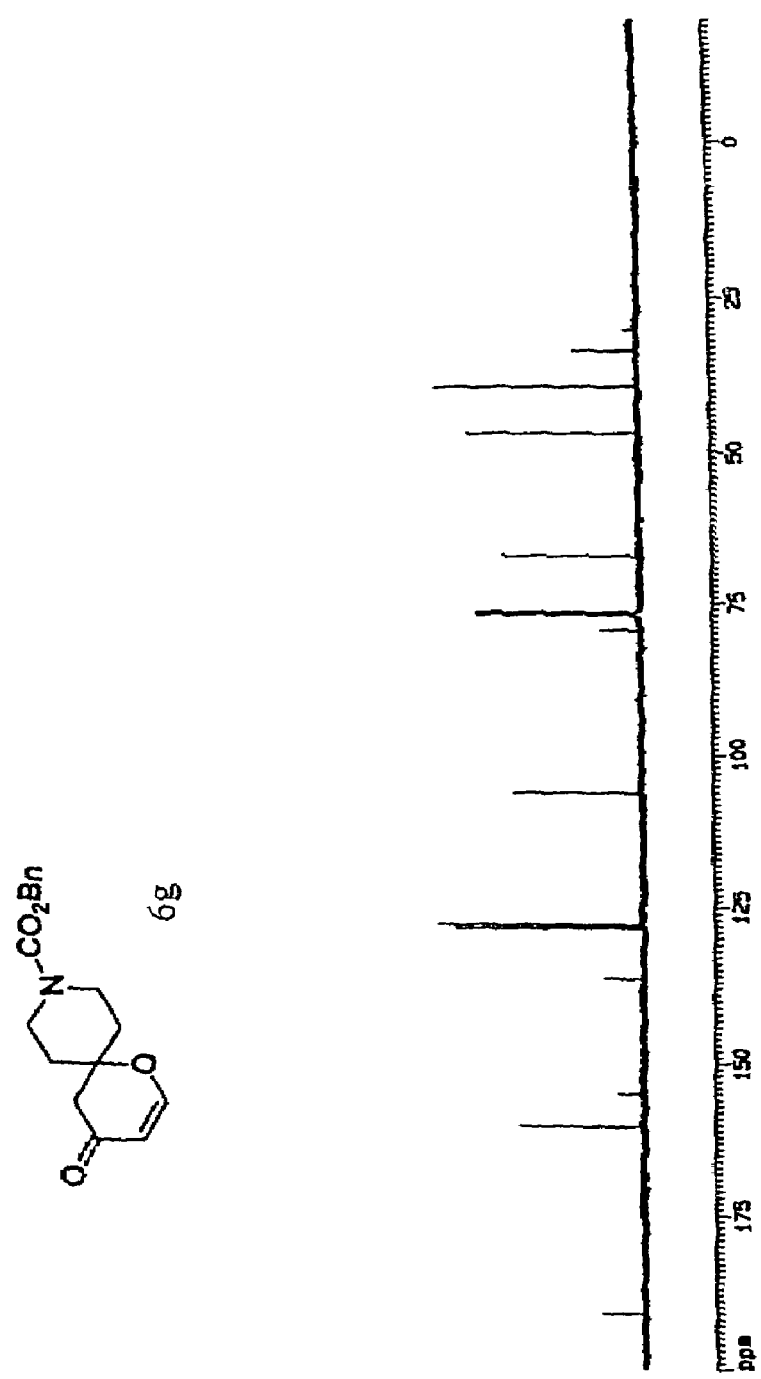
FIG. 27 shows a $^{13}$C NMR spectrum of spiro-dihydropyrone 6g.

6g (N-Benzyloxycarbonyl-8-aza-1-oxaspiro[5,5]undec-2-en-4-one): Flash column on silica gel (70% ethylacetate/hexane) gave 124 mg (82%) of the product, 6g. FIGS. 26 and 27 show the ¹H NMR spectrum and ¹³C NMR spectrum, respectively, of spiro-dihydropyrone 6g.

¹H NMR (500 MHz, CDCl₃, ppm) δ 7.35 (m, 5 H), 7.26 (d, J=6 Hz, 1 H), 5.42 (d, J=6 Hz, 1 H), 5.13 (s, 2 H), 3.97 (br, 2 H), 3.22 (br, 2 H), 2.52 (s, 2 H), 2.09 (br d, J=8 Hz, 2 H), 1.57 (br, 2H). ¹³C NMR (125 MHz, CDCl₃, ppm) δ 191.1, 160.4, 155.1, 136.5, 128.4, 128.1, 127.9, 106.3, 79.8, 67.2, 47.1, 39.3, 33.5.

Figure 28:
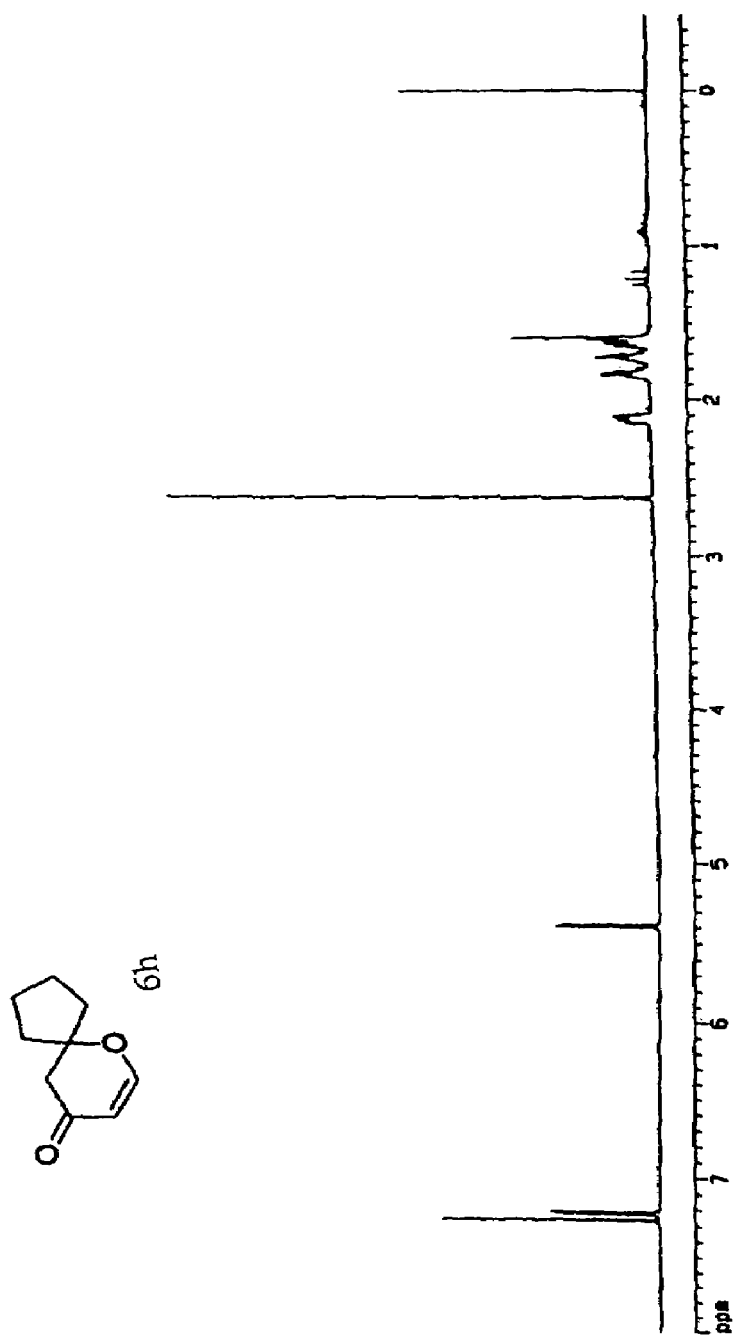
FIG. 28 shows a $^1$H NMR spectrum of spiro-dihydropyrone 6h.
Figure 29:
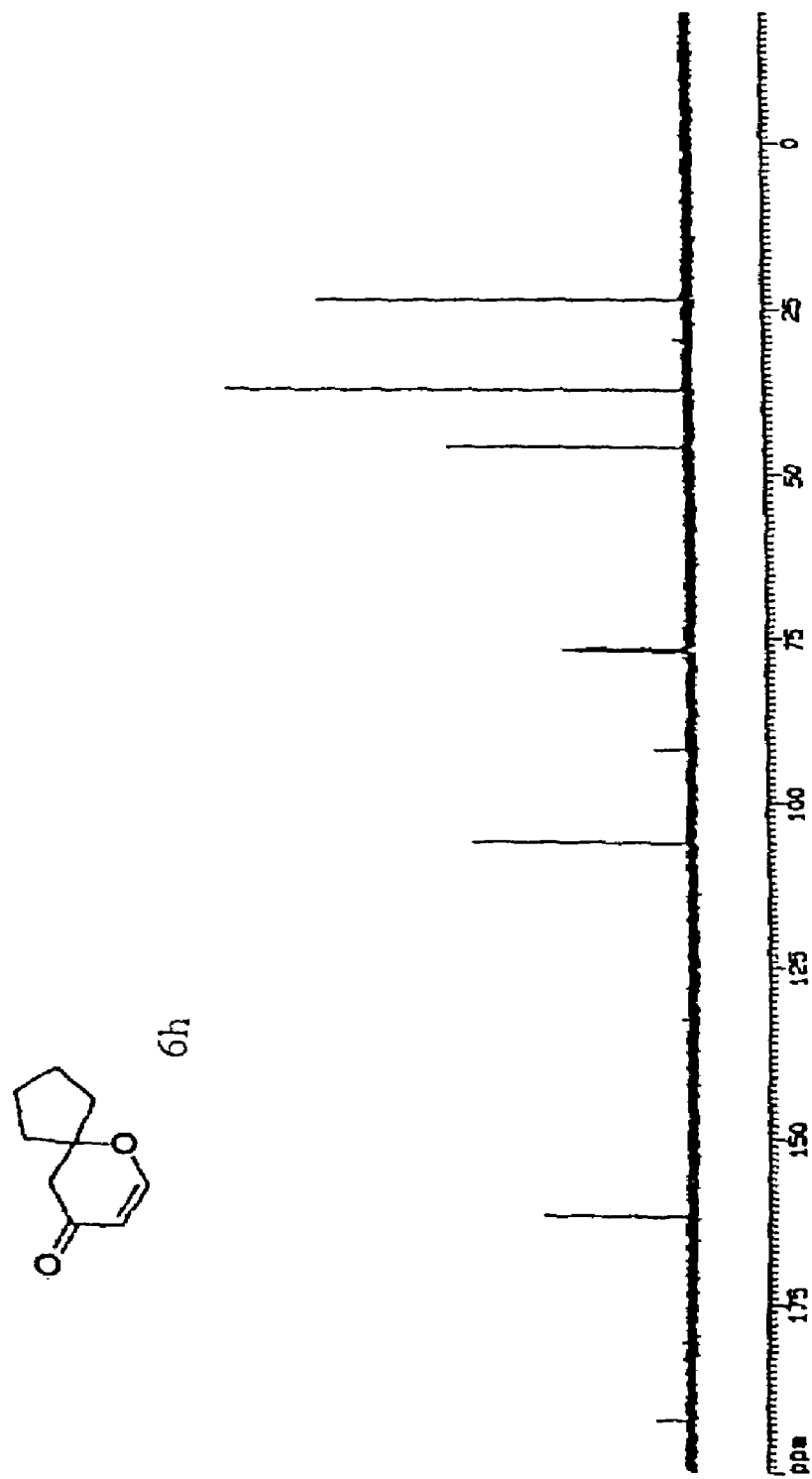
FIG. 29 shows a $^{13}$C NMR spectrum of spiro-dihydropyrone 6h.

6h (1-oxaspiro[5,5]deca-2-en-4-one): Flash column on silica gel (12% ethylacetate/hexane) gave 31 mg (41%) of the product, 6h, as a colorless oil. FIGS. 28 and 29 show the ¹H NMR spectrum and ¹³C NMR spectrum, respectively, of spiro-dihydropyrone 6h.

¹H NMR (500 MHz, CDCl₃, ppm) δ 7.22 (d, J=6 Hz, 1 H), 5.39 (d, J=6 Hz, 1 H), 2.62 (s, 2 H), 2.12 (m, 2 H), 1.83 (m, 2 H), 1.72 (m, 2 H), 1.62 (m, 2H). ¹³C NMR (125 MHz, CDCl₃, ppm) δ 192.7, 161.9, 106.2, 92.0, 45.9, 37.4, 23.7.

Figure 30:
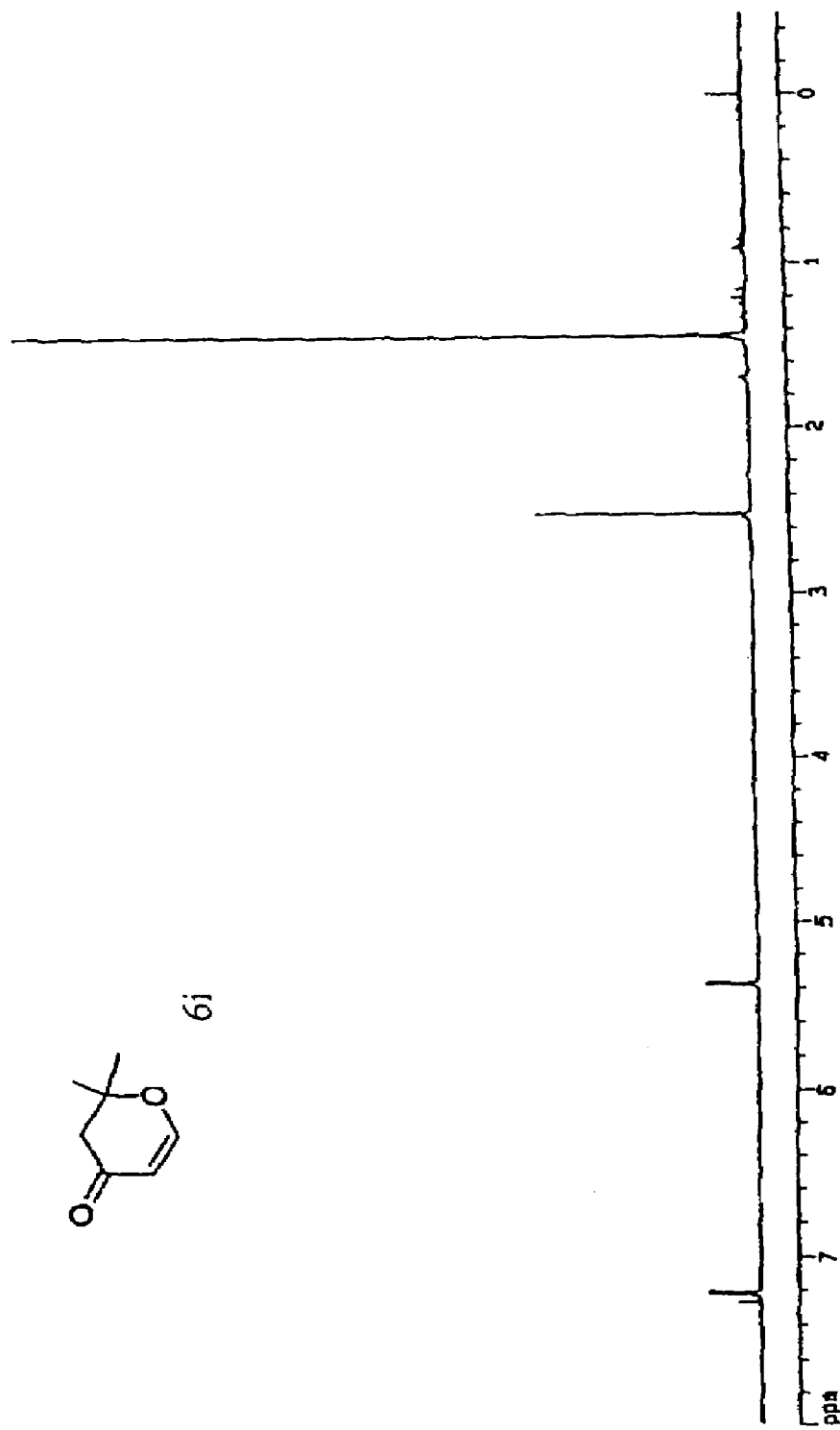
FIG. 30 shows a $^1$H NMR spectrum of spiro-dihydropyrone 6i.
Figure 31:
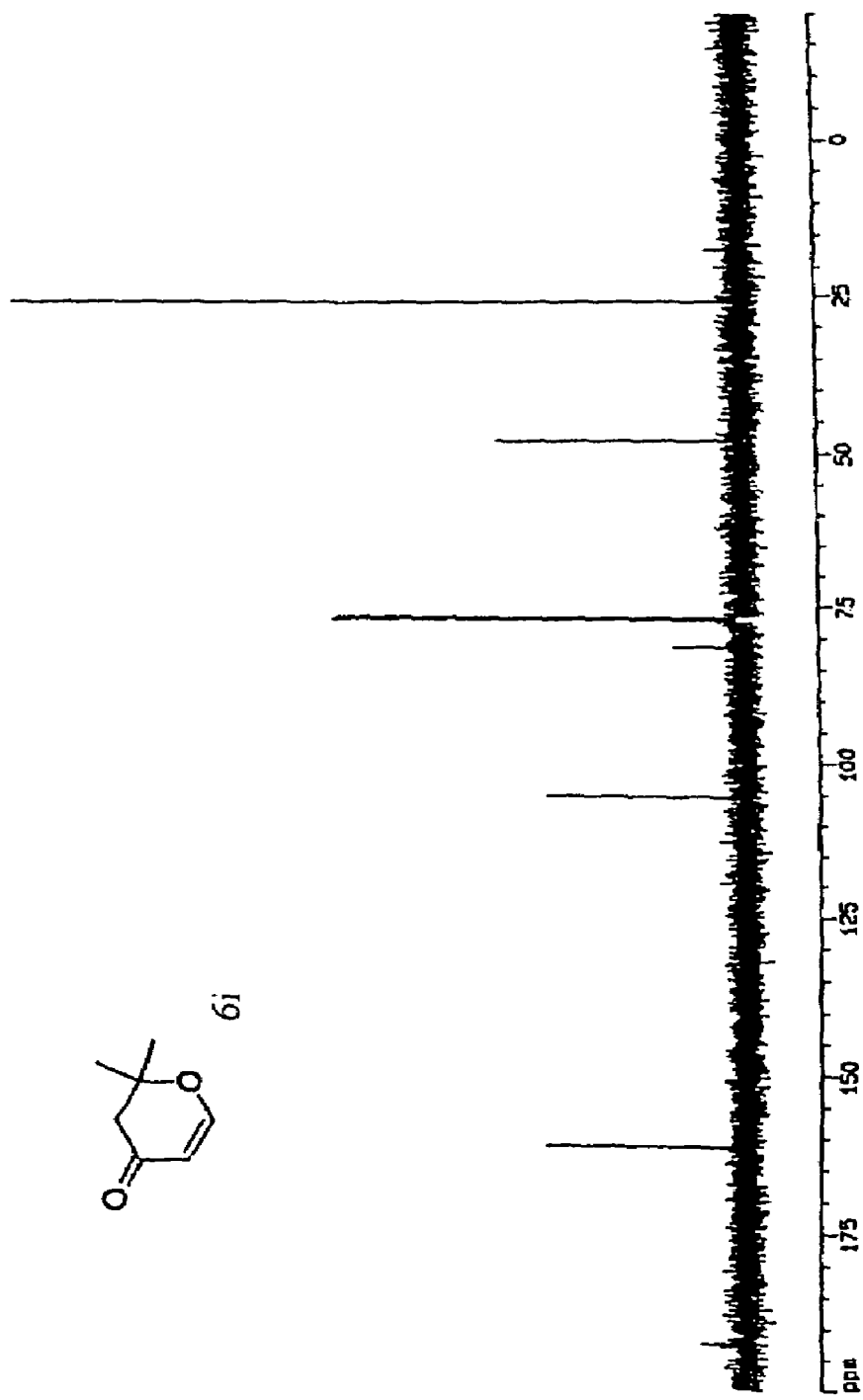
FIG. 31 shows a $^{13}$C NMR spectrum of spiro-dihydropyrone 6i.

6i 2,2-dimethyl-2,3-dihydro-pyran-4-one: Bulb to bulb distillation (60° C./8 mm Hg, ot) afforded 25 mg (40%) product 6i as colorless oil. FIGS. 30 and 31 show the ¹H NMR spectrum and ¹³C NMR spectrum, respectively, of dihydropyrone 6i.

¹H NMR (500 MHz, CDCl₃, ppm) δ 7.22 (d, J=6 Hz, 1 H), 5.38 (d, J=6 Hz, 1 H), 2.52 (s, 2 H), 1.44 (s, 6H). ¹³C NMR (125 MHz, CDCl₃, ppm) δ 192.4, 161.5, 105.3, 81.4, 48.0, 26.1.

Figure 32:
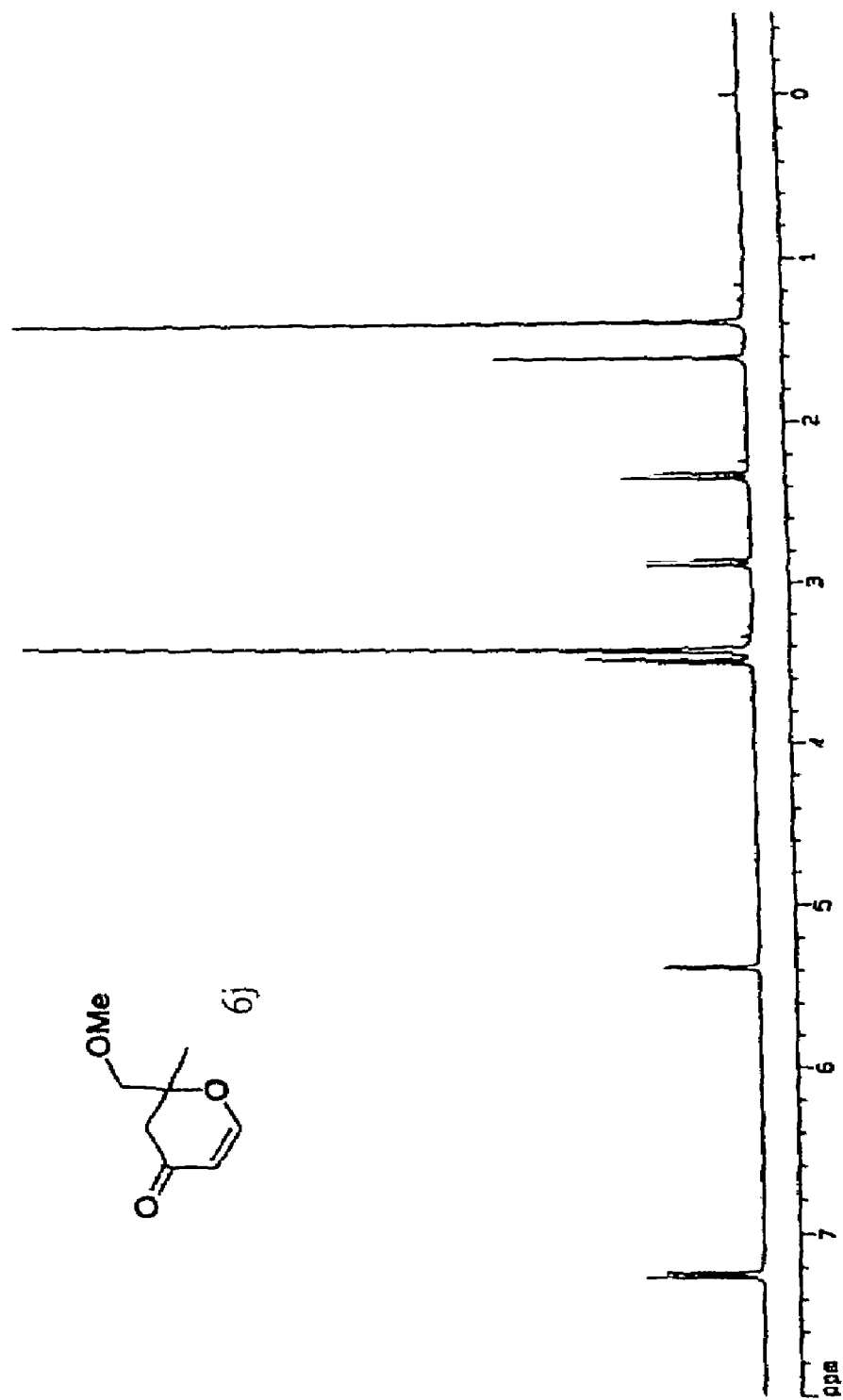
FIG. 32 shows a $^1$H NMR spectrum of spiro-dihydropyrone 6j.
Figure 33:
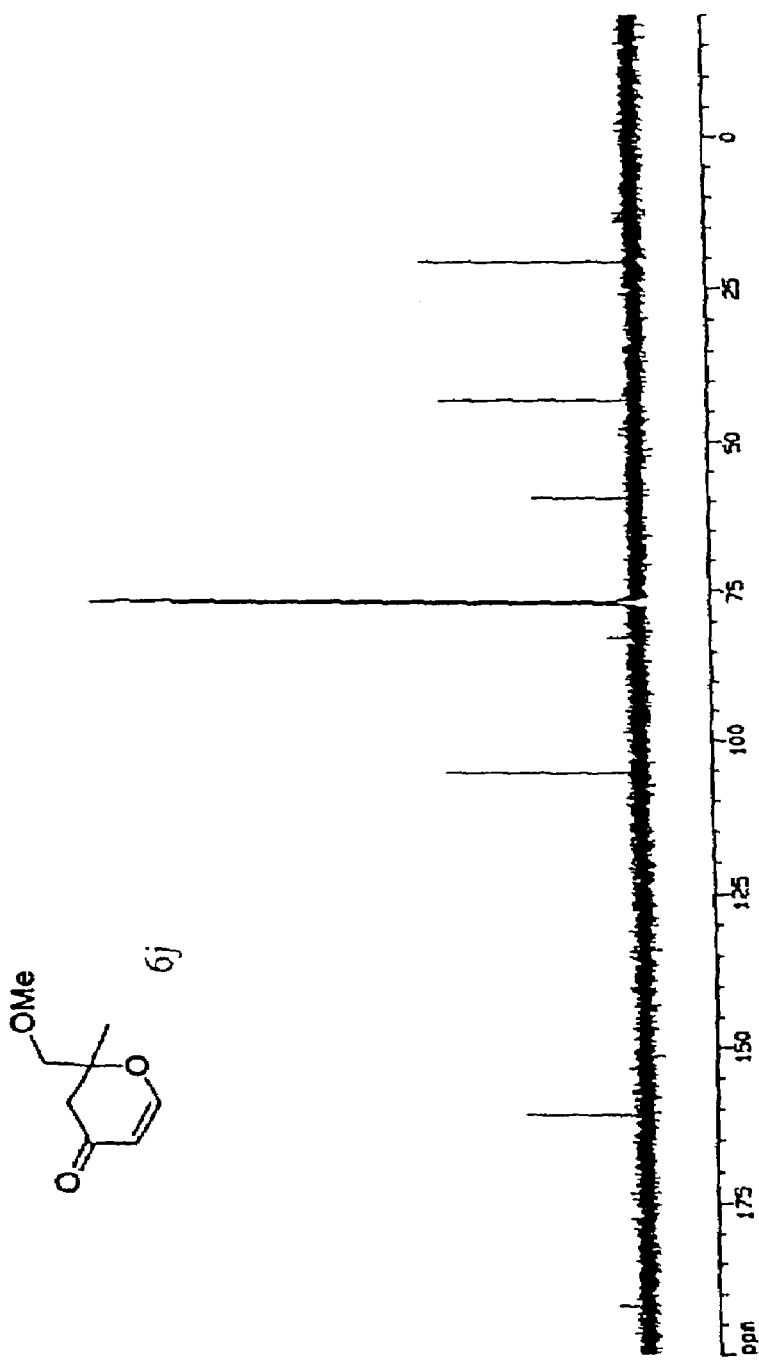
FIG. 33 shows a $^{13}$C NMR spectrum of spiro-dihydropyrone 6j.

6j 2-methoxy-2-methyl-2,3-dihydro-pyran-4-one: ¹H NMR (500 MHz, CDCl₃, ppm) δ 7.24 (d, J=6 Hz, 1 H), 5.38 (d, J=6 Hz, 1 H), 3.49 (d, J=10 Hz, 1 H), 3.43(s, 3 H), 3.42 (d, J=10 Hz, 1 H), 2.87 (d, J=16.5 Hz, 1H), 2.33 (d, J=16.5 Hz, 1 H), 1.39 (s, 3H) ¹³C NMR (125 MHz, CDCl₃, ppm) δ 192.0, 161.1, 105.6, 82.7, 76.9, 59.6, 43.2, 20.7. FIGS. 32 and 33 show the ¹H NMR spectrum and ¹³C NMR spectrum, respectively, of dihydropyrone 6j.

Figure 34:
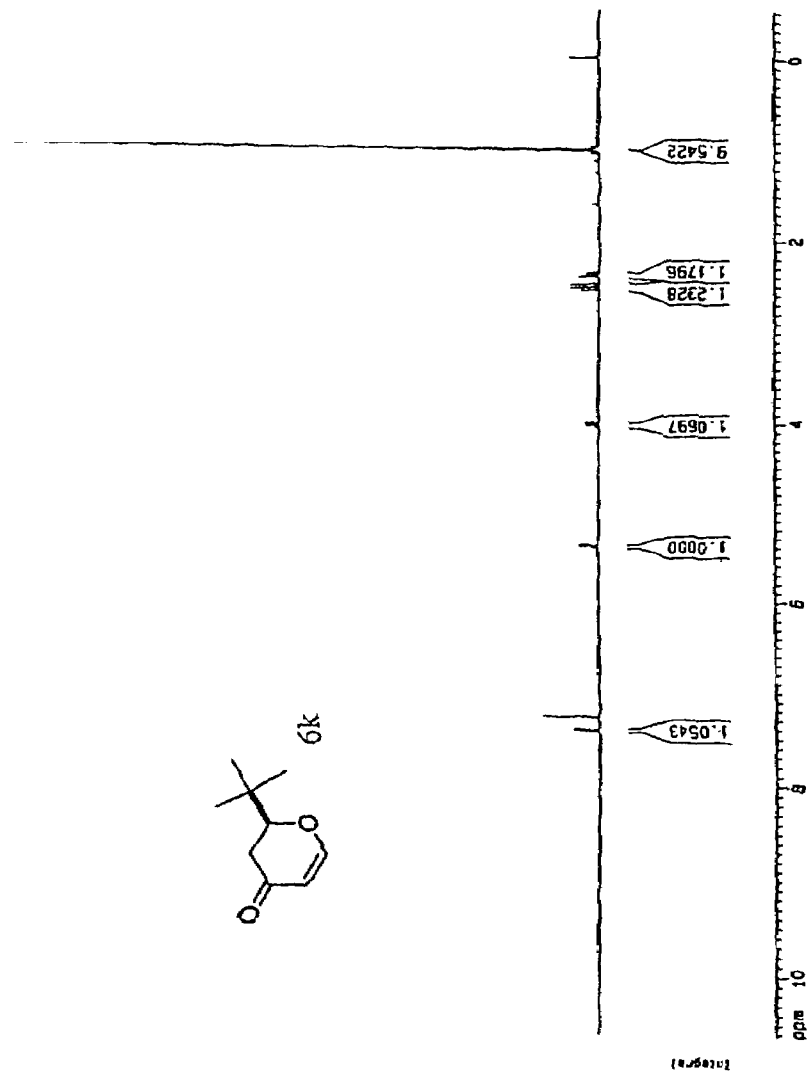
FIG. 34 shows a $^1$H NMR spectrum of spiro-dihydropyrone 6k.

6k (2-t-butyl-2,3-dihydro-pyran-4-one): Flash column on silica gel (15% ethylacetate/hexane) gave 60 mg (78%) of the product, 6k, as a slightly yellow oil. FIGS. 34 and 35 show the ¹H NMR spectrum and ¹³C NMR spectrum, respectively, of dihydropyrone 6k.

¹H NMR (500 MHz, CDCl₃, ppm) δ 7.41 (dd, J₁~0 Hz J₂=4 Hz, 1H), 5.40 (dd, J₁=1 Hz J₂=5 Hz, 1H), 4.03 (dd, J₁=3 Hz J₂=15 Hz, 1H), 2.53 (dd, J₁=15 Hz J₂=16 Hz, 1H), 2.39 (ddd, J₁=1 Hz J₂=3 Hz J₁=16 Hz, 1H), 1.00 (s, 9H). ¹³C NMR (125 MHz, CDCl₃, ppm) δ 193.6, 163.8, 106.6, 86.9, 37.2, 33.8, 25.4.

General Procedure for Enantioselective HDA Reactions Shown in Table 4

General: All liquid aldehydes were distilled prior to use. All solid aldehydes were recrystallized prior to use. PhCH₃ and CH₂Cl₂ were distilled over CaH₂. Acetyl chloride was distilled from N,N-dimethylaniline just prior to use. Melting points are uncorrected and were measured on a Fisher-Johns melting point apparatus. ¹H and ¹³C NMR were recorded at 400 or 500 MHz and 100 or 125 MHz respectively on a Bruker DRX-400 or 500 spectrometer. Proton chemical shifts were internally referenced to the residual proton resonance in CDCl₃ (δ 7.26). Carbon chemical shifts were internally referenced to the deuterated solvent signals in CDCl₃ (δ 77.00). Infrared spectra were obtained on a Nicolet 20 SXB FT-IR spectrometer. Silica gel (60 Å, 230–400 mesh) was obtained from Silicycle and used as received.

Procedure: To a solution of the aldehyde (1.0 mmol) and (4R,5R)-2,2-dimethyl-α,α,α',α'-tetra(naphtha-1-yl)-1,3-dioxolan-4,5-dimethanol (2) (Beck, A. K.; Bastani, B.; Plattner, D. A.; Petter, W.; Seebach, D.; Braunschweiger, H.; Gysi, P.; La Vecchia, L. *Chimia*, 1991, 45, 238) (0.1 mmol) in PhCH₃ (0.5 mL) at −78° C. (dry-ice/acetone cooling bath) was added (E)-1-dimethylamino-3-tert-butyldimethylsiloxy-1,3-butadiene (1) (Kozmin, S. A.; Janey, J. M.; Rawal, V. H. *J. Org. Chem.* 1999, 64, 3039) (0.5 mmol) dropwise. The resulting reaction mixture was kept at the indicated temperature for the specified period of time (Table 4). The mixture was then recooled to −78° C. prior to dilution with CH₂Cl₂ (1.0 mL). Freshly distilled acetyl chloride (1.0 mmol) was then added and the reaction mixture stirred at −78° C. for 15 min. The crude mixture was subsequently transferred directly on top of a silica gel column and eluted with EtOAc/hexanes to afford the desired dihydropyran-4-one.

4a ((S)-2,3-Dihydro-2-phenyl-4H-pyran-4-one), (Bednarski, M.; Danishefsky, S. J. *J. Am. Chem. Soc.*, 1986, 108, 7060; Corey, E. J.; Cywin, C. L.; Roper, T. D. *Tetrahedron Lett.*, 1992, 33, 6907):

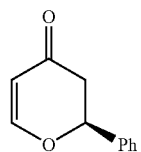

Figure 36:
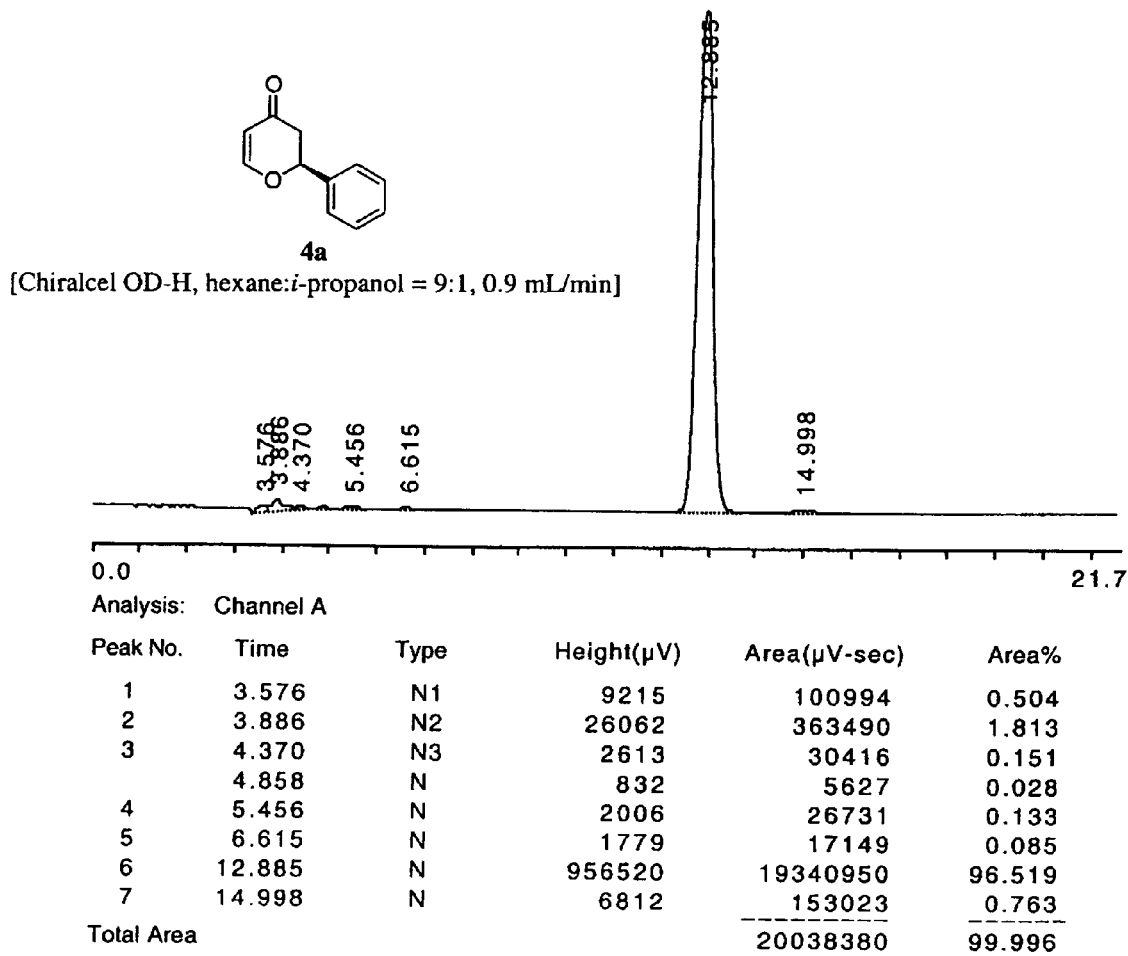
Figure 37:
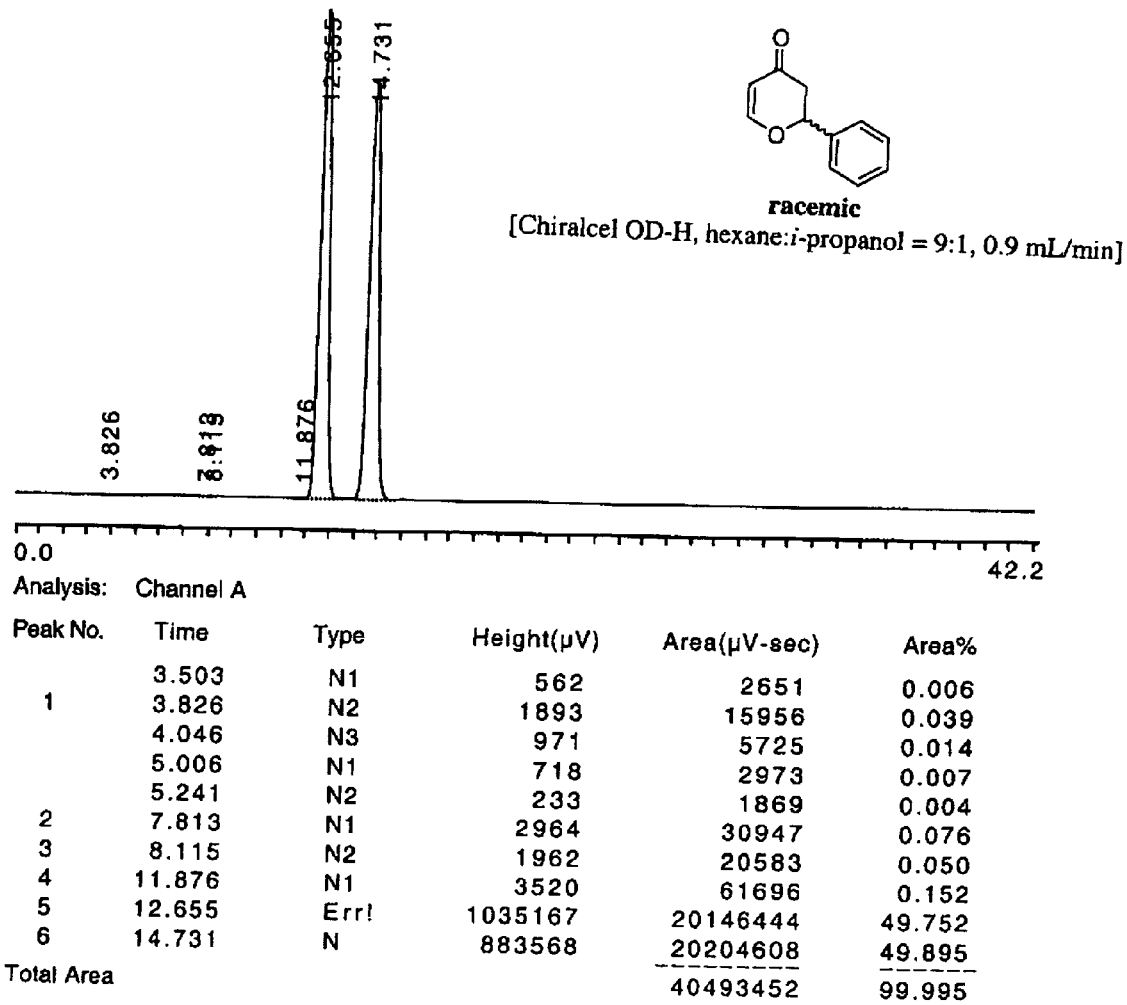

4a 4a was isolated as a clear, colorless oil: >98% ee [Chiralcel OD-H, hexane: i-propanol=10:1, 0.9 mL/min, t$_R$ (major) 12.9 min, t$_R$ (minor) 15.0 min]; [α]$_D^{24}$=+95.6° (c 0.35, CHCl₃); ¹H NMR (CDCl₃, 500 MHz) δ 7.59 (1H, d, J=6.5 Hz), 7.43 (5H, m), 5.54 (1H, dd, J=6.5, 1.0 Hz), 5.43 (1H, dd, J=14.0, 4.5 Hz), 2.92 (1H, dd, J=17.0, 14.0 Hz), 2.67 (1H, ddd, J=17.0, 4.5, 1.0 Hz); ¹³C NMR (CDCl₃, 125 MHz) δ 192.2, 163.2, 137.8, 128.9, 128.8, 126.1, 107.4, 81.1, 43.4; IR (film) ν 1676, 1595, 1403, 1269, 1228 cm⁻¹. FIG. 36 shows an HPLC scan of a single enantiomer of 4a and FIG. 37 shows an HPLC scan of racemic 4a.

4b (2,3-Dihydro-2-(4-Methoxyphenyl)-4H-pyran-4-one), (Wang, B.; Feng, X.; Huang, Y.; Liu, H.; Cui, X.; Jiang, Y. *J. Org. Chem.*, 2002, 67, 2175):

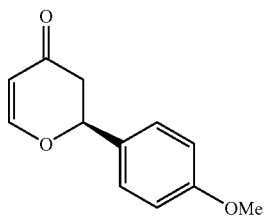

Figure 38:
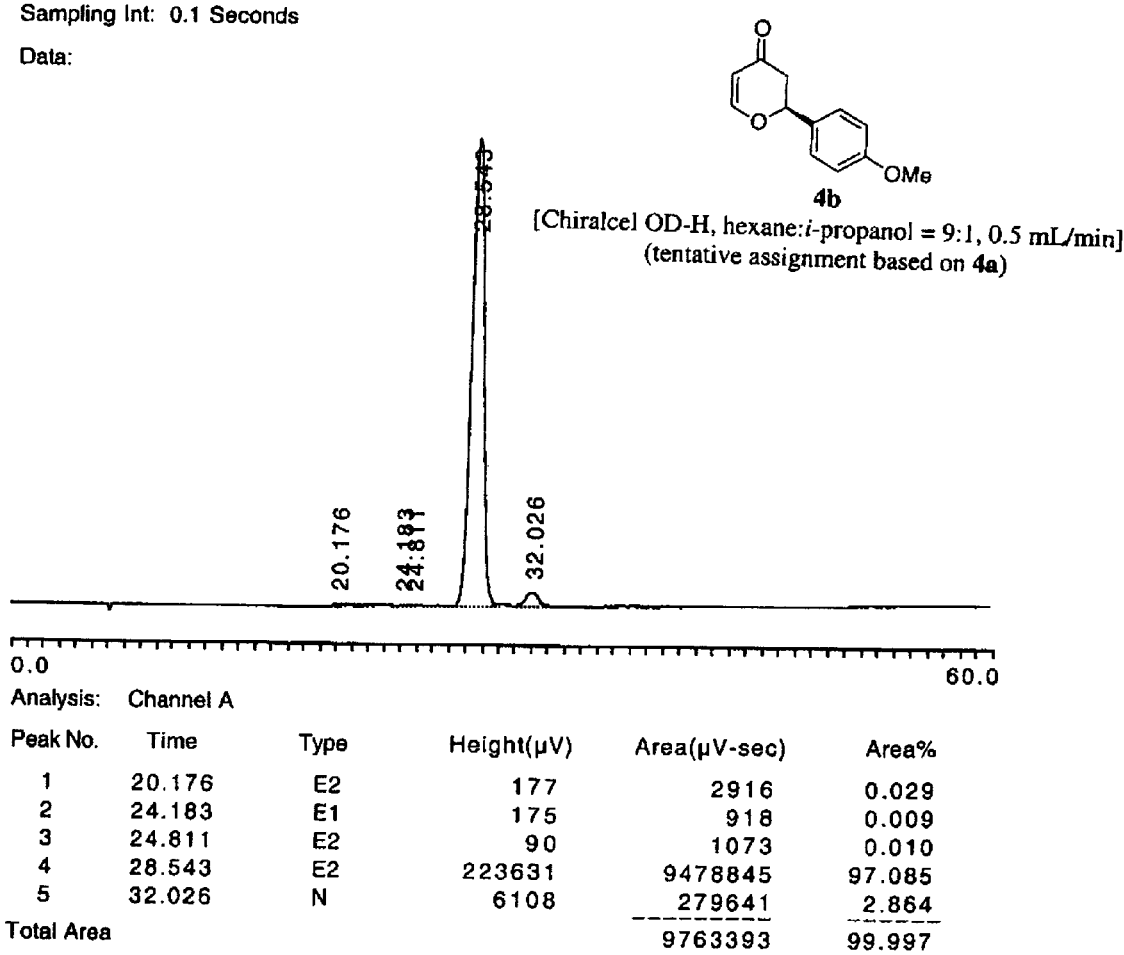
FIG. 38 shows an HPLC scan of a single enantiomer of 4b.
Figure 39:
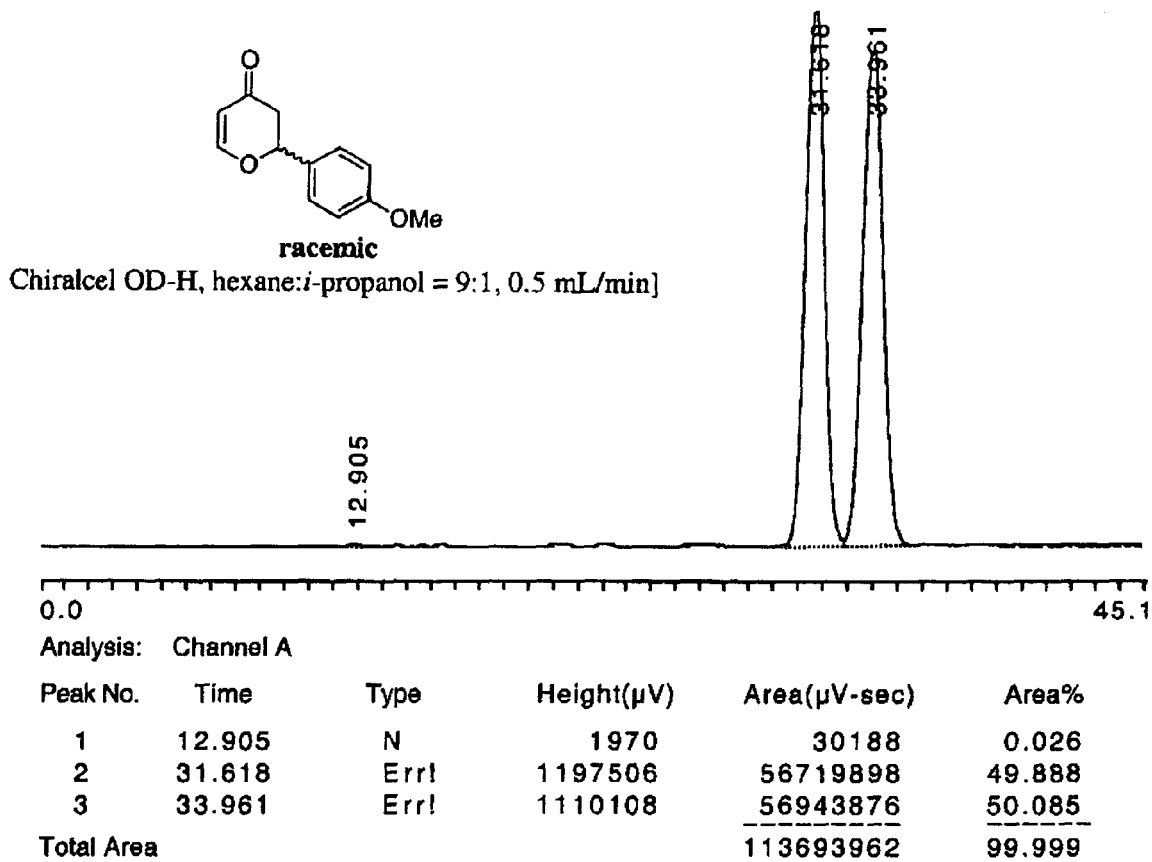
FIG. 39 shows an HPLC scan of racemic 4b.

4b 4b was isolated as a clear, colorless crystalline solid: 94% ee [Chiralcel OD-H, hexane:i-propanol=9:1, 0.5 mL/min, t$_R$ (major) 28.5 min, t$_R$ (minor) 32.0 min]; [α]$_D^{24}$=+148.20 (c 0.29, CHCl₃); m.p.=48–49° C. (CHCl₃); ¹H NMR (CDCl₃, 500 MHz) δ 7.45 (1H, d, J=6.0 Hz), 7.32 (2H, d, J=8.5 Hz), 6.93 (2H, d, J=8.5 Hz), 5.50 (1H, dd, J=6.0, 1.0 Hz), 5.36 (1H, dd, J=14.5, 3.5 Hz), 3.18 (3H, s), 2.92 (1H, dd, J=17.0, 14.5 Hz), 2.61 (1H, ddd, J=17.0, 3.5, 1.0 Hz); ¹³C NMR (CDCl₃, 125 MHz) δ 192.35, 163.24, 159.97, 129.71, 127.67, 114.07, 107.13, 80.79, 55.24, 43.05; IR (KBr) ν 3067, 2965, 2935, 2906, 2875, 2837, 1661, 1592, 1517, 1453, 1411, 1284, 1259, 1229, 1210, 1172, 1111, 1031, 991, 944, 931, 869, 819, 791 cm$^{-1}$. FIG. 38 shows an HPLC scan of a single enantiomer of 4b and FIG. 39 shows an HPLC scan of racemic 4b.

4c (2-(3-Bromophenyl)-2,3-dihydro-4H-pyran-4-one), (Long, J.; Hu, J.; Shen, X.; Ji, B.; Ding, K. *J. Am. Chem. Soc.*, 2002, 124; Aikawa, K.; Irie, R.; Katsuki, T. *Tetrahedron*, 2001, 57, 845):

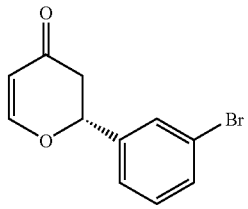

4c

Figure 41:
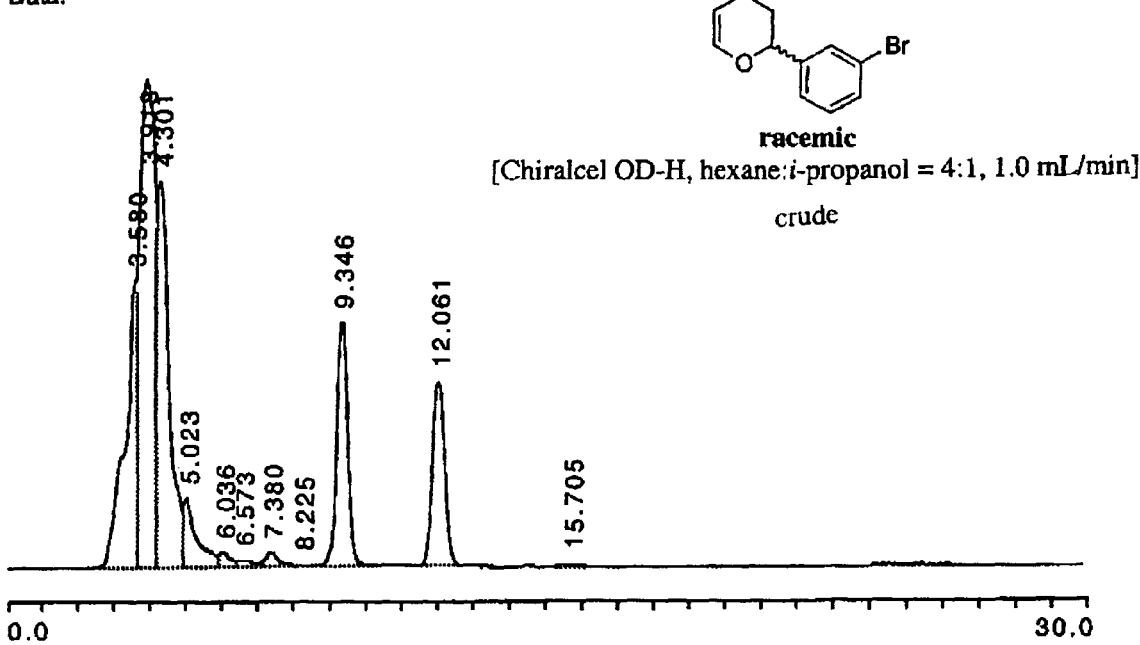
FIG. 41 shows an HPLC scan of racemic 4c.

N.B.: (4S,5S)-2,2-Dimethyl-α,α,α',α'-tetra(naphtha-1-yl)-1,3-dioxolan-4,5-dimethanol (ent-2) was used as the catalyst. 4c was isolated as a pale yellow oil: 97% ee [Chiralcel OD-H, hexane:i-propanol=19:1, 1.0 mL/min, $t_R$ (minor)=9.3 min, $t_R$ (major)=12.0 min]; $[\alpha]_D^{25}$=−73.9° (c 1.06, CHCl$_3$); $^1$H NMR (CDCl$_3$, 500 MHz) δ 7.58 (1H, m), 7.52 (1H, dt, J=7, 2 Hz), 7.48 (1H, d, J=7 Hz), 7.28 (2H, m), 5.54 (1H, dd, J=6, 1 Hz), 5.40 (1H, dd, J=15, 4 Hz), 2.86 (1H, dd, J=16, 14 Hz), 2.67 (1H, ddd, J=16, 4, 1 Hz); $^{13}$C NMR (CDCl$_3$, 125 MHz) δ 191.4, 162.8, 140.1, 132.0, 130.4, 129.2, 124.5, 122.9, 107.6, 80.1, 43.3; IR (film) ν 1683, 1593, 1402, 1270, 1226, 1038 cm$^{-1}$. FIG. 40 shows an HPLC scan of a single enantiomer of 4c and FIG. 41 shows an HPLC scan of racemic 4c.

4d (2,3-Dihydro-2-(4-trifluoromethylphenyl)-4H-pyran-4-one), (Kezuka, S.; Mita, T.; Ohtsuki, N.; Ikeno, T.; Yamada, T. *Bull. Chem. Soc. Jpn.*, 2001, 74, 1333):

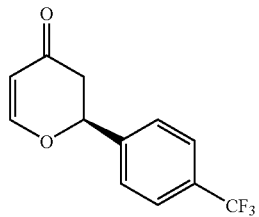

Figure 42:
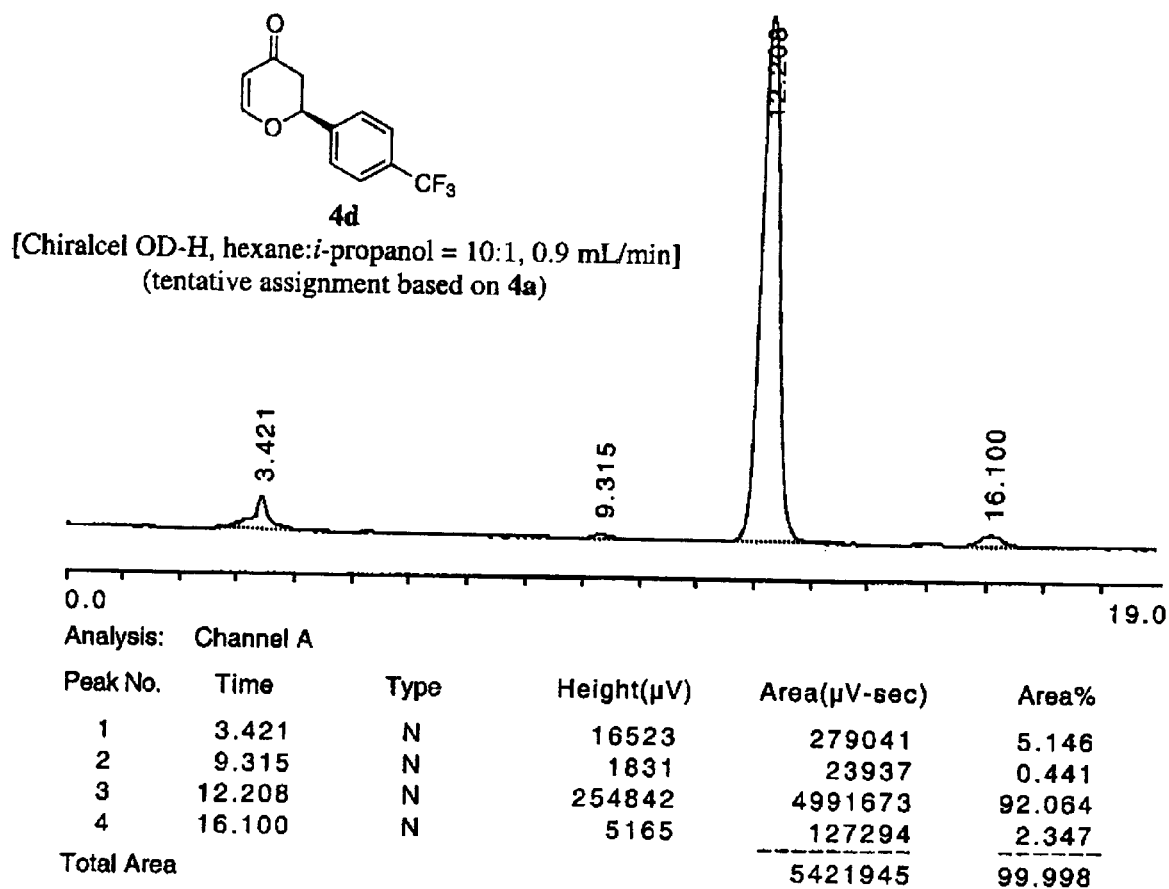
FIG. 42 shows an HPLC scan of a single enantiomer of 4d.

4d 4d was isolated as a clear, colorless crystalline solid: 95% ee [Chiralcel OD-H, hexane:i-propanol=10:1, 0.9 mL/min, $t_R$ (major) 12.2 min, $t_R$ (minor) 16.1 min]; $[\alpha]_D^{23}$=+77.20 (c 0.31, CHCl$_3$); m.p.=44–45° C. (CHCl$_3$); $^1$H NMR (CDCl$_3$, 500 MHz) δ 7.68 (2H, d, J=8.0 Hz), 7.53 (2H, d, J=8.0 Hz), 7.49 (1H, d, J=6.0 Hz), 5.55 (1H, dd, J=6.0, 1.0 Hz), 5.49 (1H, dd, J=14.5, 3.5 Hz), 2.85 (1H, dd, J=17.0, 14.5 Hz), 2.69 (1H, ddd, J=17.0, 3.5, 1.0 Hz); $^{13}$C NMR (CDCl$_3$, 125 MHz) δ 191.27, 162.81, 141.78, 130.98 (q, J=32.6 Hz), 126.23, 125.84 (q, J=3.8 Hz), 124.87, 107.65, 80.16, 43.37; IR (KBr) ν 3070, 3059, 2953, 2870, 1675, 1597, 1584, 1410, 1326, 1275, 1232, 1212, 1167, 1125, 1068, 1041, 1019, 940, 841 cm$^{-1}$. FIG. 42 shows an HPLC scan of a single enantiomer of 4d and FIG. 43 shows an HPLC scan of racemic 4d.

4e (2,3-Dihydro-2-(1-naphthyl)-4H-pyran-4-one), (Long, J.; Hu, J.; Shen, X.; Ji, B.; Ding, K. *J. Am. Chem. Soc.*, 2002, 124; Aikawa, K.; Irie, R.; Katsuki, T. *Tetrahedron*, 2001, 57, 845):

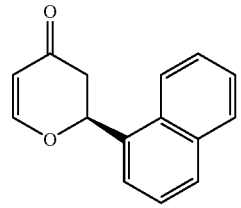

Figure 44:
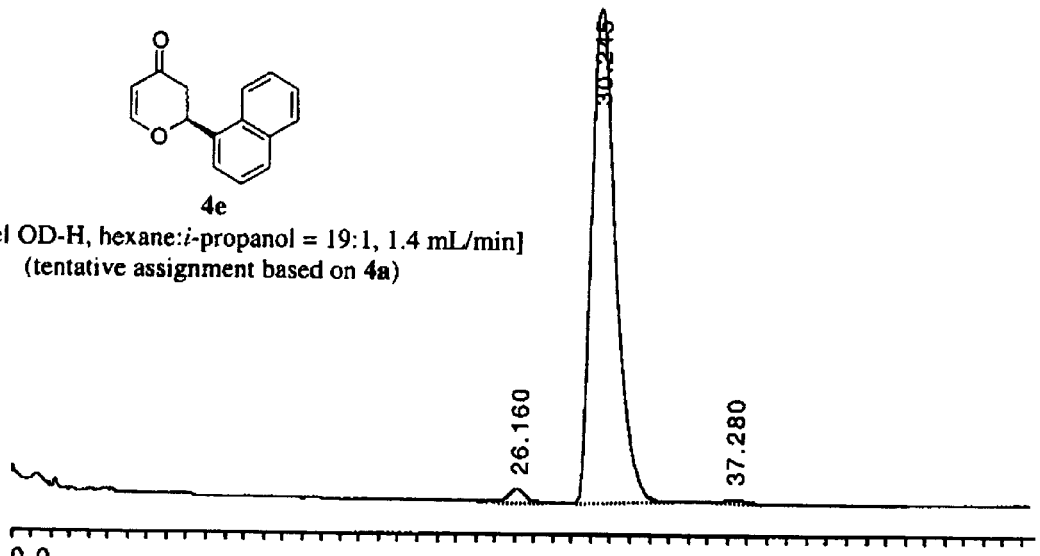
FIG. 44 shows an HPLC scan of a single enantiomer of 4e.
Figure 45:
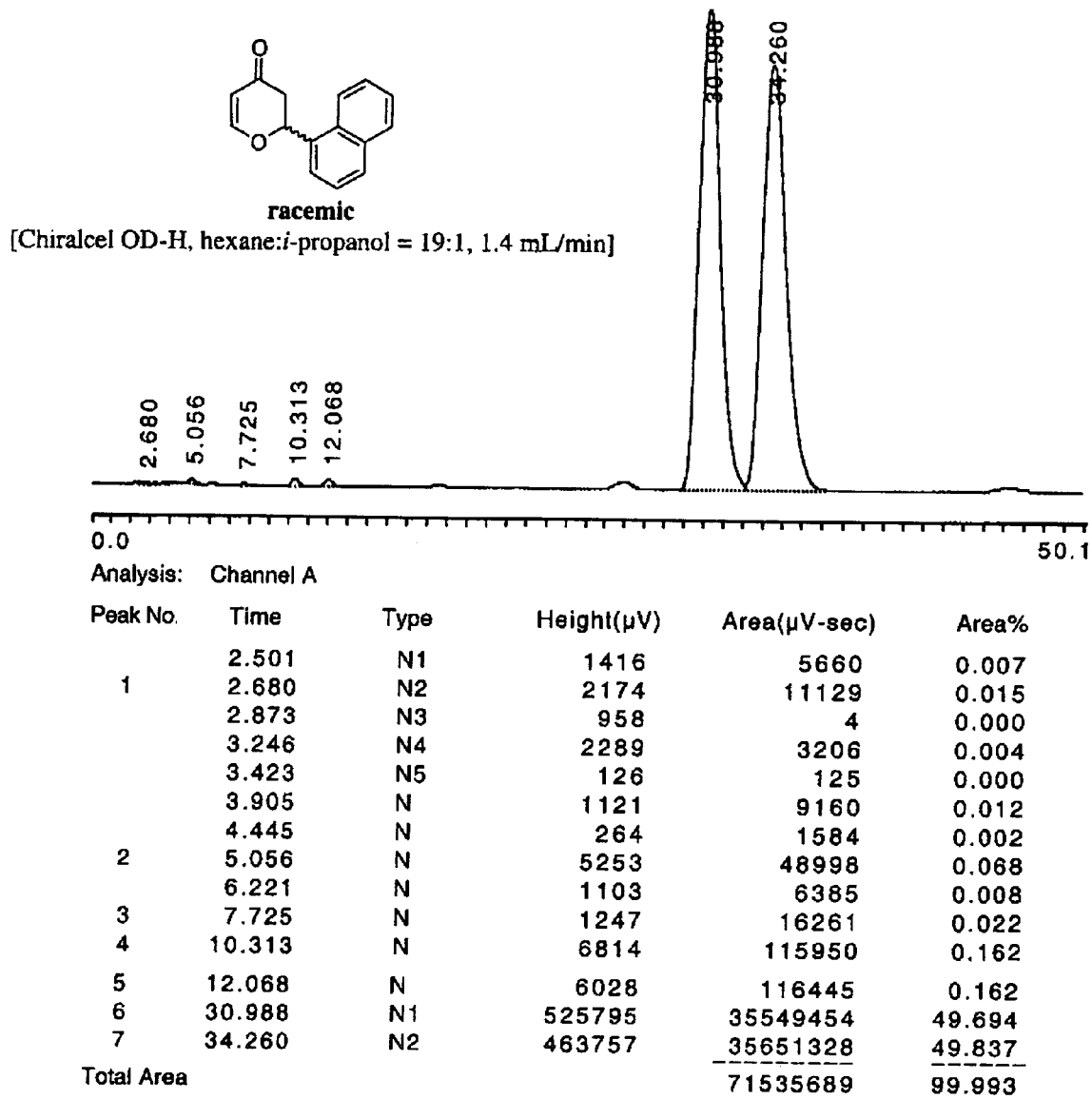
FIG. 45 shows an HPLC scan of racemic 4e.

4e 4e was isolated as a pale, yellow oil: 99% ee [Chiralcel OD-H, hexane:i-propanol=20:1, 1.4 mL/min, $t_R$ (major) 30.2 min, $t_R$ (minor) 37.3 min]; $[\alpha]_D^{23}$=−104.1° (c 0.30, CHCl$_3$); $^1$H NMR (CDCl$_3$, 500 MHz) δ 7.98 (1H, d, J=8.0 Hz), 7.95–7.87 (2H, m), 7.66 (1H, d, J=6.5 Hz), 7.60–7.50 (4H, m), 6.18 (1H, dd, J=14.0, 3.5 Hz), 5.62 (1H, dd, J=6.0, 1.0 Hz), 3.08 (1H, dd, J=17.0, 14.0 Hz), 2.87 (1H, ddd, J=17.0, 3.5, 1.0 Hz); $^{13}$C NMR (CDCl$_3$, 125 MHz) δ 192.33, 163.37, 133.76, 133.20, 129.98, 129.50, 129.08, 126.73, 126.00, 125.25, 123.84, 122.54, 107.49, 78.39, 42.68; IR (film) ν 3053, 2967, 2921, 1669, 1590, 1513, 1403, 1339, 1270, 1223, 1183, 1037, 983, 932, 863, 800, 776 cm$^{-1}$. FIG. 44 shows an HPLC scan of a single enantiomer of 4e and FIG. 45 shows an HPLC scan of racemic 4e.

4f (2,3-Dihydro-2-(2-naphthyl)-4H-pyran-4-one), (Hanamoto, T.; Furuno, H.; Sugimoto, Y.; Inanaga, J. *Synlett*, 1997, 79):

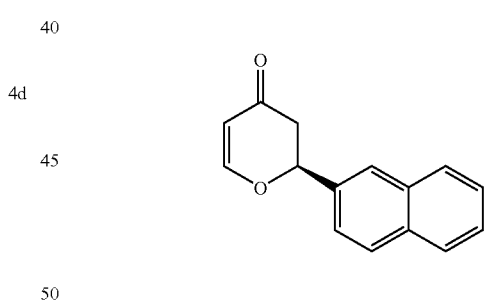

Figure 46:
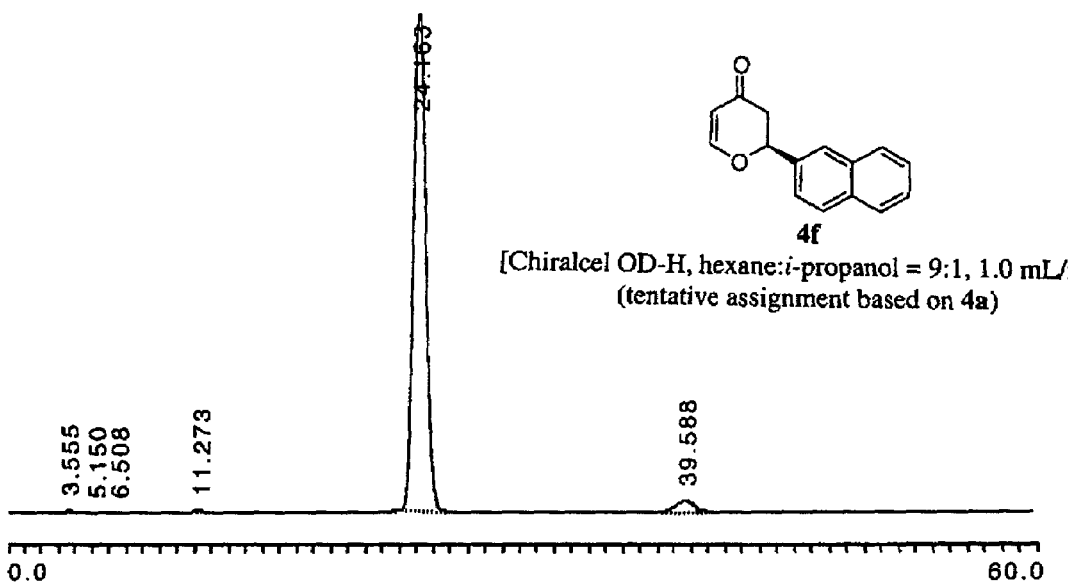
FIG. 46 shows an HPLC scan of a single enantiomer of 4f.
Figure 47:
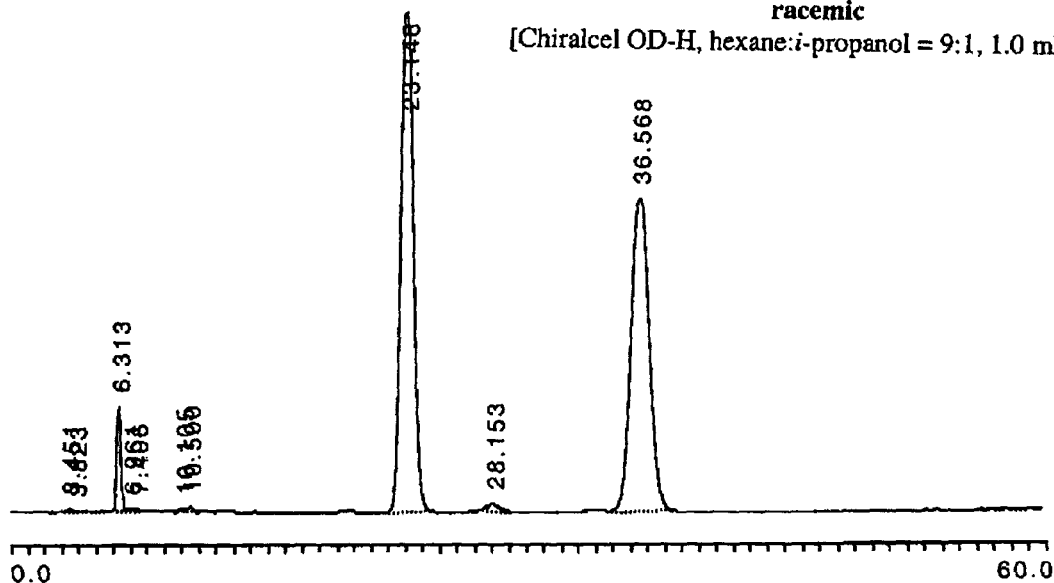
FIG. 47 shows an HPLC scan of racemic 4f.

4f 4f was isolated as a pale yellow, crystalline solid: 94% ee [Chiralcel OD-H, hexane:i-propanol=9:1, 1.0 mL/min, $t_R$ (major) 24.2 min, $t_R$ (minor) 39.6 min]; $[\alpha]_D^{25}$=+110.40 (c 0.13, CHCl$_3$); mp=115–117° C. (EtOAc/hexanes); $^1$H NMR (CDCl$_3$, 400 MHz) δ 7.92–7.83 (4H, m), 7.56–7.46 (4H, m), 5.60–5.54 (2H, m), 2.99 (1H, dd, J=17.0, 14.5 Hz), 2.74 (1H, ddd, J=8.5, 3.5, 1.0 Hz); $^{13}$C NMR (CDCl$_3$, 100 MHz) δ 192.11, 163.25, 135.19, 133.39, 133.09, 128.85, 128.18, 127.83, 126.72, 126.68, 125.46, 123.57, 107.46, 81.20, 43.41; IR (KBr) ν 3054, 2917, 1661, 1592, 1403, 1268, 1222, 1041, 991, 927, 900, 864, 825, 749 cm$^{-1}$. FIG. 46 shows an HPLC scan of a single enantiomer of 4f and FIG. 47 shows an HPLC scan of racemic 4f.

4g (S)-2,3-Dihydro-2-(2-furyl)-4H-pyran-4-one (Wang, B.; Feng, X.; Huang, Y.; Liu, H.; Cui, X.; Jiang, Y. *J. Org.*

Chem., 2002, 67, 2175; Long, J.; Hu, J.; Shen, X.; Ji, B.; Ding, K. J. Am. Chem. Soc., 2002, 124, 10; Schaus, S. E.; Branalt, J.; Jacobsen, E. N. J. Org. Chem., 1998, 63, 403):

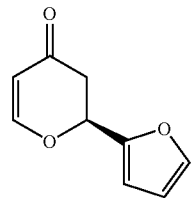

Figure 48:
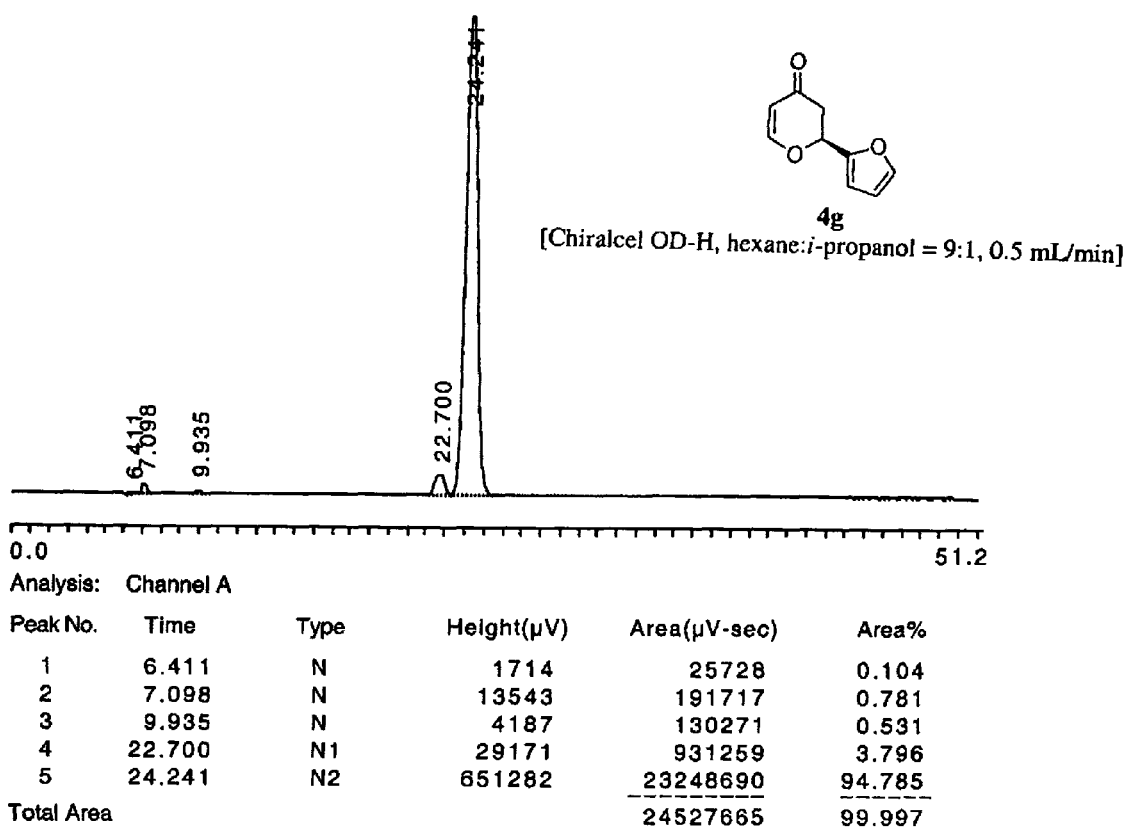
FIG. 48 shows an HPLC scan of a single enantiomer of 4g.
Figure 49:
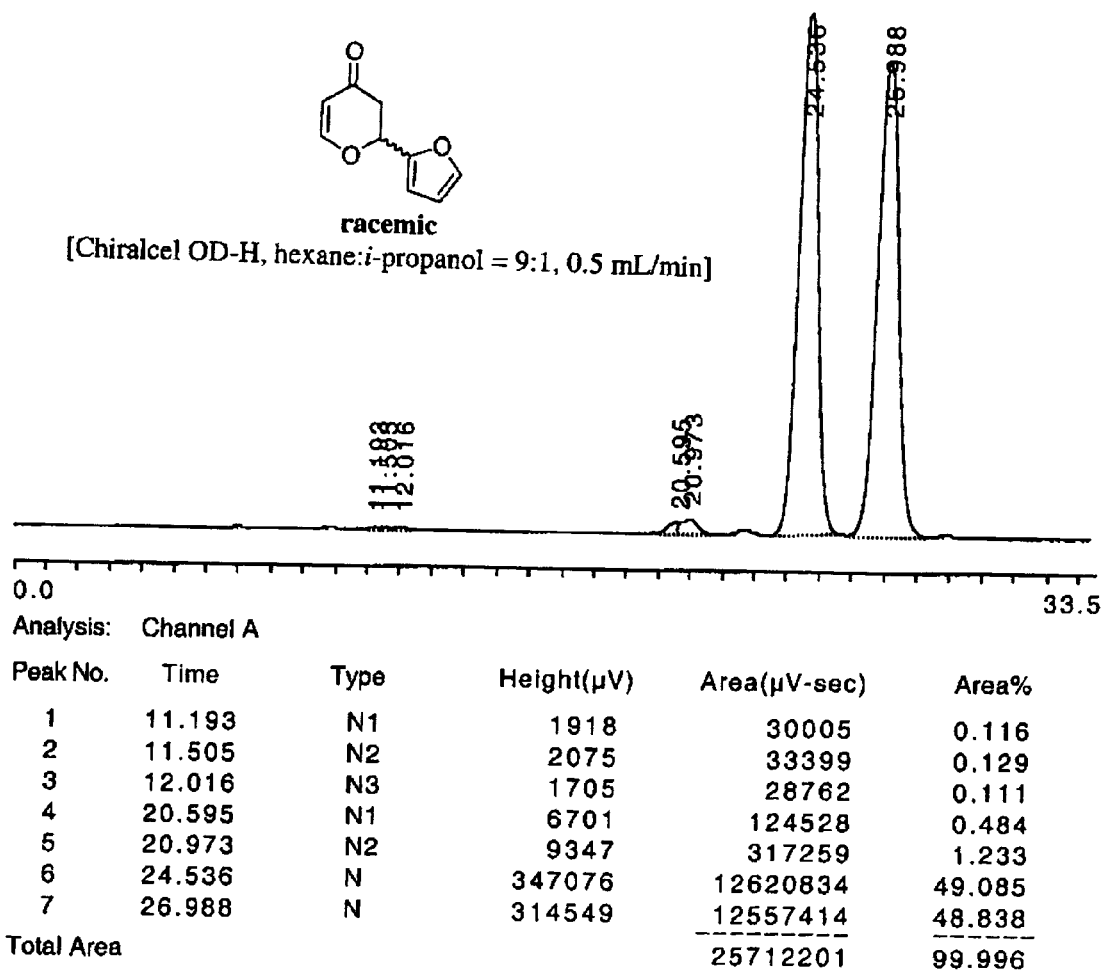
FIG. 49 shows an HPLC scan of racemic 4g.

4g 4g was isolated as a pale yellow, crystalline solid: 92% ee [Chiralcel OD-H, hexane:i-propanol=9:1, 0.5 mL/min, $t_R$ (minor) 22.7 min, $t_R$ (major) 24.2 min]; $[\alpha]_D^{25}$=+342.1° (c 0.10, CHCl$_3$); m.p.=67–69° C. (EtOAc/hexanes); $^1$H NMR (CDCl$_3$, 500 MHz) δ 7.48 (1H, dd, J=2.0, 1.0 Hz), 7.38 (1H, d, J=6.0 Hz), 6.46 (1H, d, J=4.0 Hz), 6.41 (1H, dd, J=3.0, 2.0), 5.51 (1H, dd, J=6.0, 1.0 Hz), 5.48 (1H, dd, J=13.5, 4.0 Hz), 3.10 (1H, dd, J=17.0, 13.5 Hz), 2.74 (1H, ddd, J=17.0, 4.0, 1.0 Hz); $^{13}$C NMR (CDCl$_3$, 125 MHz) δ 191.3, 162.4, 150.0, 143.6, 110.6, 109.7, 107.4, 73.5, 39.5; IR (KBr) υ 1677, 1596, 1403, 1272, 1209 cm$^{-1}$. FIG. 48 shows an HPLC scan of a single enantiomer of 4g and FIG. 49 shows an HPLC scan of racemic 4g.

4h ((S)-2-Cyclohexyl-2,3-Dihydro-4H-pyran-4-one), (Corey, E. J.; Cywin, C. L.; Roper, T. D. Tetrahedron Lett, 1992, 33, 6907; Aikawa, K.; Irie, R.; Katsuki, T. Tetrahedron, 2001, 57, 845):

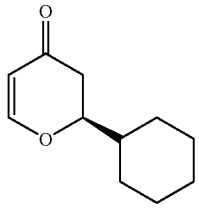

Figure 50:
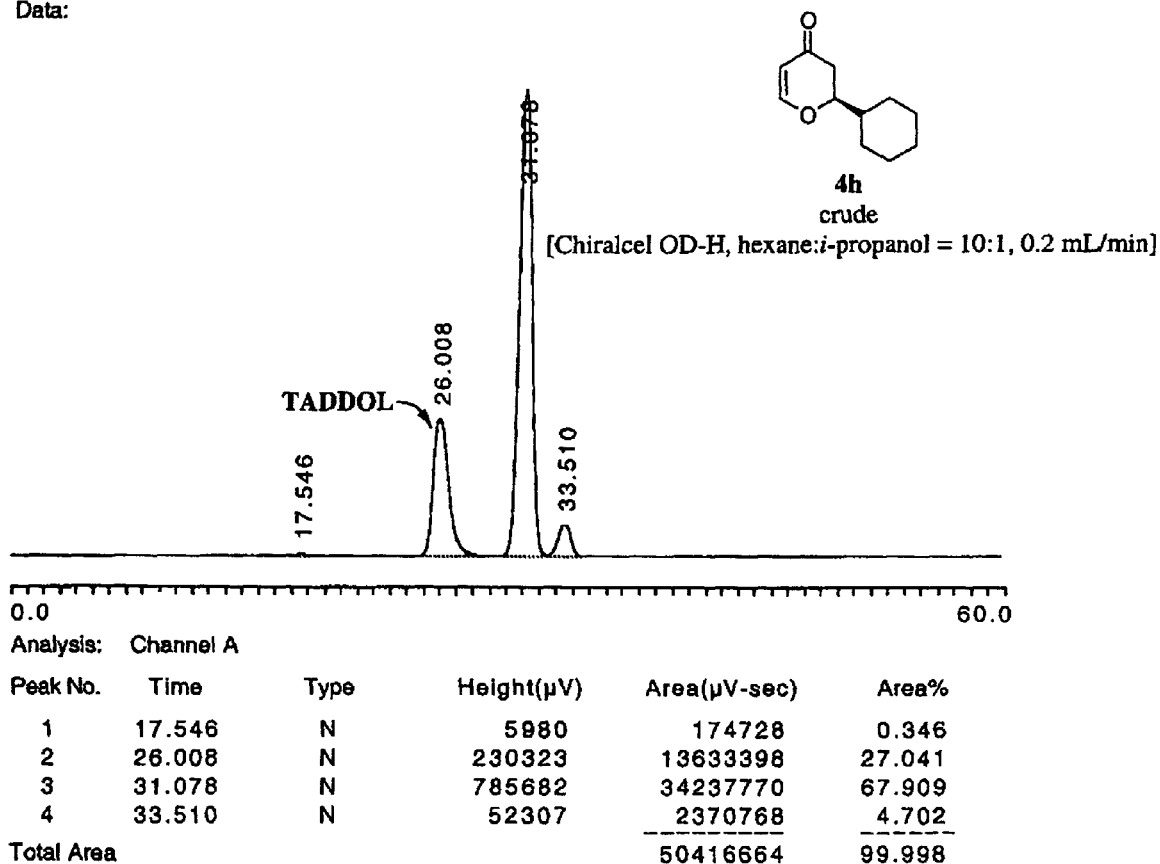
FIG. 50 shows an HPLC scan of a single enantiomer of 4h.
Figure 51:
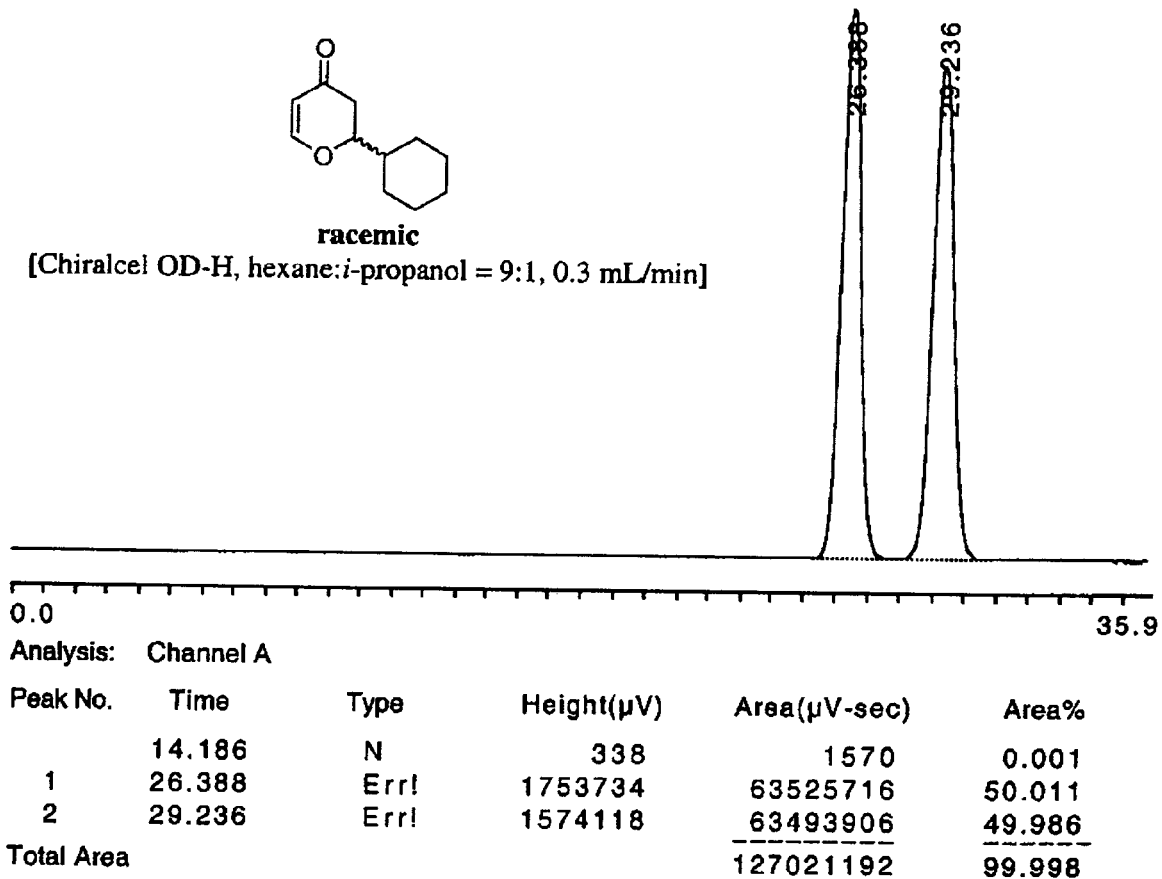
FIG. 51 shows an HPLC scan of racemic 4h.

4h 4h was isolated as a clear, pale yellow oil: 87% ee [Chiralcel OD-H, hexane:i-propanol=10:1, 0.2 mL/min, $t_R$ (major) 31.1 min, $t_R$ (minor) 33.5 min]; $[\alpha]_D^{25}$=+157.2° (c 0.41, CHCl$_3$); $^1$H NMR (CDCl$_3$, 500 MHz) δ 7.36 (1H, d, J=6.0 Hz), 5.38 (1H, dd, J=6.0, 1.0 Hz), 4.16 (1H, ddd, J=14.5, 5.5, 3.0 Hz), 2.54 (1H, dd, J=16.5, 14.5 Hz), 2.38 (1H, ddd, J=16.5, 3.0, 1.0 Hz), 1.91–1.84 (1H, m), 1.83–1.75 (2H, m), 1.74–1.62 (3H, m), 1.31–1.00 (5H, m); $^{13}$C NMR (CDCl$_3$, 125 MHz) δ 193.30, 163.59, 106.79, 83.55, 41.34, 39.07, 28.11, 27.99, 26.19, 25.83, 25.76; IR (film) υ 3050, 2928, 2854, 1681, 1596, 1450, 1407, 1278, 1215, 1189, 1038, 993, 910, 793 cm$^{-1}$. FIG. 50 shows an HPLC scan of a single enantiomer of 4h and FIG. 51 shows an HPLC scan of racemic 4h.

4i ((S)-2,3-Dihydro-2-n-propyl-4H-pyran-4-one), (Corey, E. J.; Cywin, C. L.; Roper, T. D. Tetrahedron Lett., 1992, 33, 6907):

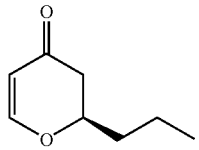

Figure 52:
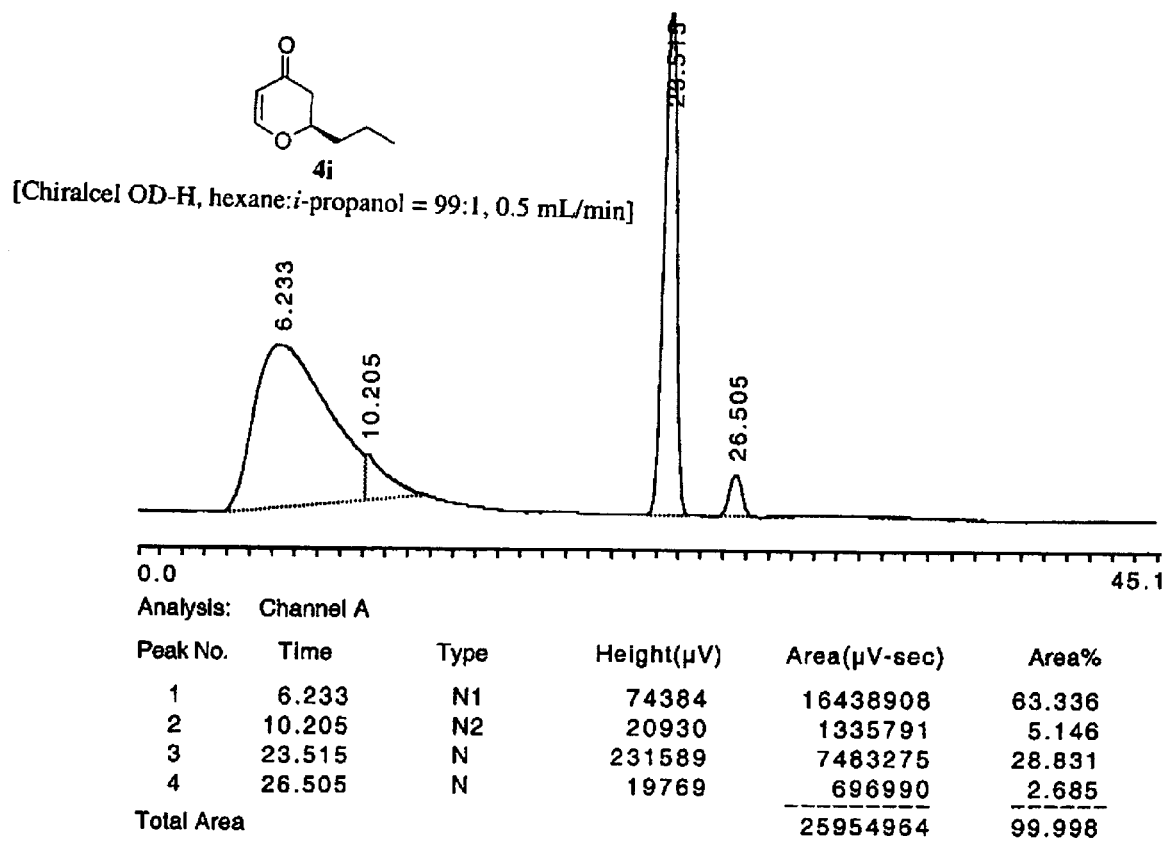
FIG. 52 shows an HPLC scan of a single enantiomer of 4i.
Figure 53:
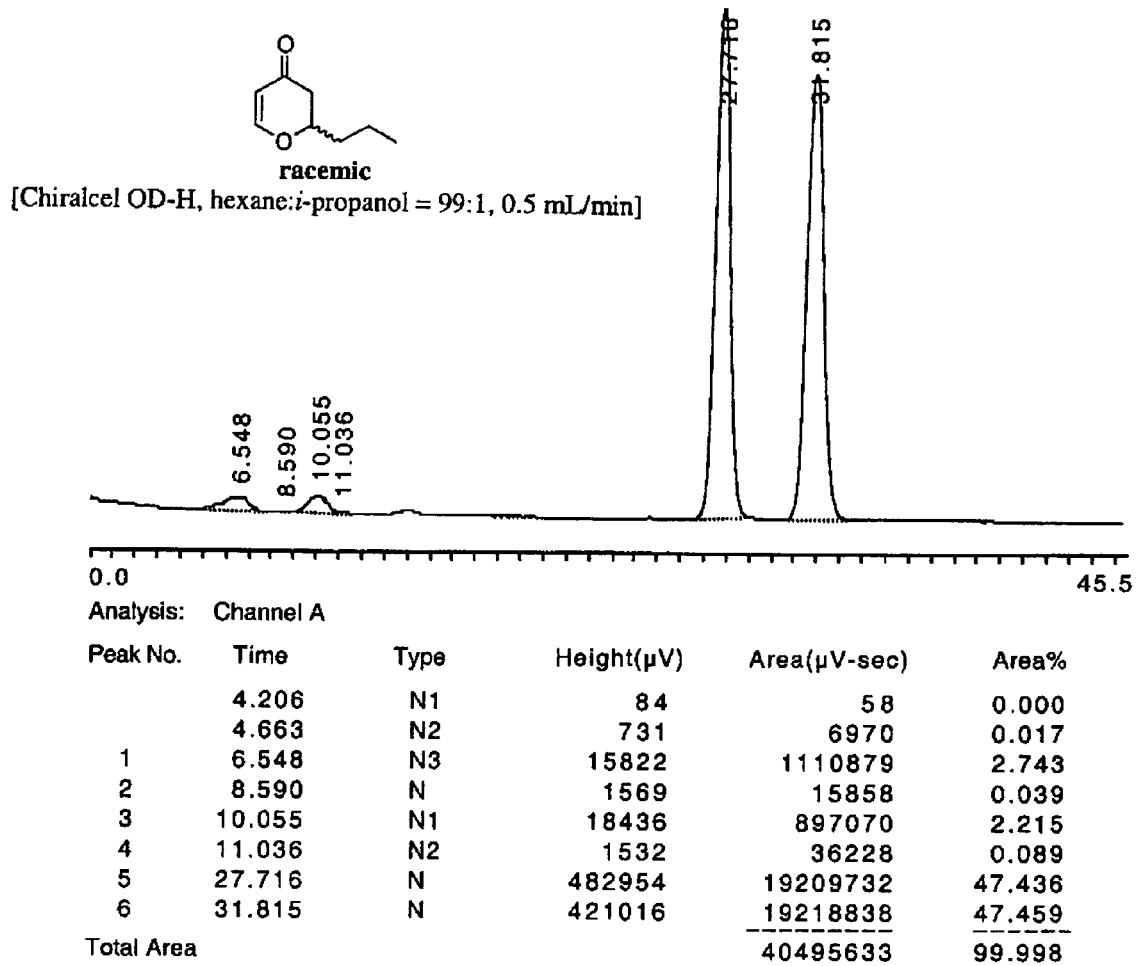
FIG. 53 shows an HPLC scan of racemic 4i.

4i 4i was isolated as a clear, pale yellow oil: 83% ee [Chiralcel OD-H, hexane:i-propanol=99:1, 1.0 mL/min, $t_R$ (major) 23.5 min, $t_R$ (minor) 26.5 min]; $[\alpha]_D^{25}$=+159.7° (c 0.74, CHCl$_3$); $^1$H NMR (CDCl$_3$, 500 MHz) δ 7.32 (1H, d, J=6.0 Hz), 5.36 (1H, dd, J=6.0, 1.0 Hz), 4.37 (1H, m), 2.47 (1H, dd, J=16.0 Hz, 12.5 Hz), 2.38 (1H, ddd, J=16.5, 4.0, 1.0 Hz), 1.77 (1H, m), 1.61 (1H, m), 1.44 (2H, m), 0.93 (3H, t, J=7.5 Hz); $^{13}$C NMR (CDCl$_3$, 125 MHz) δ 192.8, 163.3, 106.9, 79.3, 41.8, 36.4, 18.0, 13.7; IR (film) υ 1682, 1596, 1406, 1274, 1218, 1037 cm$^{-1}$. FIG. 52 shows an HPLC scan of a single enantiomer of 4i and FIG. 53 shows an HPLC scan of racemic 4i.

4j ((R)-2,3-Dihydro-2-[(E)-styryl]-4H-pyran-4-one), (Wang, B.; Feng, X.; Huang, Y.; Liu, H.; Cui, X.; Jiang, Y. J. Org. Chem., 2002, 67, 2175; Long, J.; Hu, J.; Shen, X.; Ji, B.; Ding, K. J. Am. Chem. Soc., 2002, 124, 10; Schaus, S. E.; Branalt, J.; Jacobsen, E. N. J. Org. Chem., 1998, 63, 403):

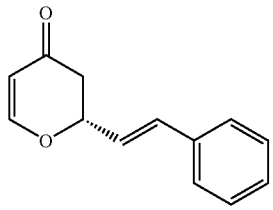

4j

Figure 54:
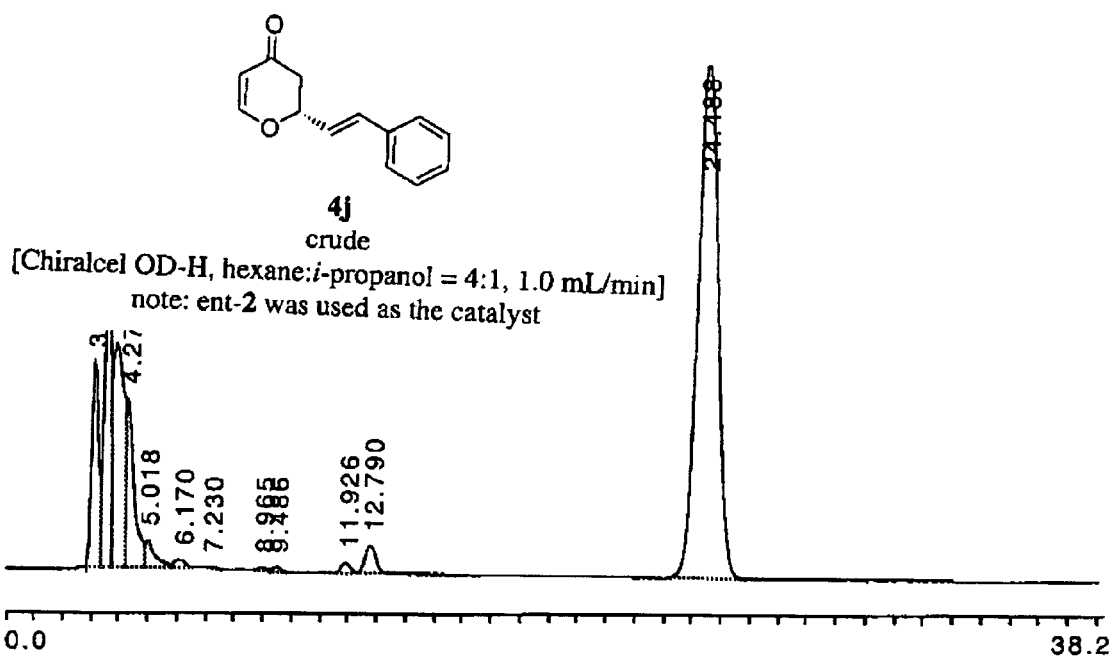
FIG. 54 shows an HPLC scan of a single enantiomer of 4j.

N.B.: (4S,5S)-2,2-Dimethyl-α,α,α'α'-tetra(naphtha-1-yl)-1, 3-dioxolan-4,5-dimethanol (ent-2) was used as the catalyst. 4j was isolated as a clear, pale yellow oil: 95% ee [Chiralcel OD-H, hexane:i-propanol=4:1, 1.0 mL/min, $t_R$ (minor) 12.8 min, $t_R$ (major) 24.5 min]; $[\alpha]_D^{25}$=−187.0° (c 0.58, CHCl$_3$); $^1$H NMR (CDCl$_3$, 500 MHz) δ 7.41 (3H, m), 7.35 (2H, t, J=8.0 Hz), 7.30 (1H, m), 6.72 (1H, d, J=16.0 Hz), 6.29 (1H, dd, J=16.0, 6.0 Hz), 5.47 (1H, d, J=6.0 Hz), 5.08 (1H, m), 2.74 (1H, dd, J=17.0, 13.0 Hz), 2.63 (1H, dd, J=17.0, 4.0 Hz); $^{13}$C NMR (CDCl$_3$, 125 MHz) δ 191.9, 162.9, 135.6, 133.8, 128.7, 128.5, 126.8, 125.0, 107.3, 79.7, 42.0; IR (film) υ 1675, 1593, 1405, 1268, 1217, 1038 cm$^{-1}$. FIG. 54 shows an HPLC scan of a single enantiomer of 4j and FIG. 55 shows an HPLC scan of racemic 4j.

General Procedure for TADDOL catalyzed Diels-Alder Reactions Shown in Table 5

To a solution of the acrolein (0.5 mmol) and the TADDOL (0.1 mmol) in PhCH$_3$ (0.75 mL) at −80° C. was added (E)-1-dimethylamino-3-tert-butyldimethylsiloxy-1,3-butadiene (1.0 mmol) dropwise. The resulting reaction mixture was stirred for 48 h at −80° C. Lithium aluminum hydride (1.0 M in Et$_2$O, 2.0 mL, 2.0 mmol) was then added at −80° C. The reaction mixture was stirred for 1 h at −80° C. and another 2 h at rt. The excess LiAlH$_4$ was carefully quenched with H$_2$O (0.5 mL) with frequent cooling of the mixture. The mixture was then diluted with Et$_2$O (20 mL). The solids were filtered off and washed with Et$_2$O (3×5 mL). The combined organic filtrates were concentrated in vacuo to afford a clear, colorless oil. This was taken up in acetonitrile (3.0 mL) and cooled in an ice-bath. HF (5% in CH$_3$CN, 0.75 mL) was then added and the mixture stirred for 1 h at 0° C. The solvent was then removed in vacuo and the residue chromatographed on silica gel to afford 503.

The enantiomeric excess was determined by Mosher ester analysis via integration of the aliphatic CH$_2$O protons.

To a solution of the acrolein (0.5 mmol) and the TADDOL (0.1 mmol) in PhCH$_3$ (0.75 mL) at −80° C. was added (E)-1-dimethylamino-3-tert-butyldimethylsiloxy-1,3-butadiene (1.0 mmol) dropwise. The resulting reaction mixture was stirred for 48 h at −80° C. HF (5% in CH$_3$CN, 0.75 mL) was then added and the mixture stirred for 1 h at −80° C. and another 1 h at rt. The solvent was then removed in vacuo and the residue chromatographed on silica gel to afford 504.

General Procedure for TADDOL Catalyzed Diels-Alder Reactions Shown in Table 6

To a solution of the acrolein (1.0 mmol) and the TADDOL (0.1 mmol) in PhCH$_3$ (0.75 mL) at −80° C. was added (E)-1-diethylamino-1,3-butadiene (0.5 mmol) dropwise. The resulting reaction mixture was stirred for 78 h at −80° C. Lithium aluminum hydride (1.0 M in Et$_2$O, 2.0 mL, 2.0 mmol) was then added at −80° C. The reaction mixture was stirred for 1 h at −80° C. and another 2 h at rt. The excess LiAlH$_4$ was carefully quenched with H$_2$O (0.5 mL) with frequent cooling of the mixture. The mixture was then diluted with Et$_2$O (20 mL). The solids were filtered off and washed with Et$_2$O (3×5 mL). The combined organic filtrates were concentrated in vacuo to afford a clear, colorless oil. This was taken up in acetonitrile (3.0 mL) and cooled in an ice-bath. HF (5% in CH$_3$CN, 0.75 mL) was then added and the mixture stirred for 1 h at 0° C. The solvent was then removed in vacuo and the residue chromatographed on silica gel to afford 507.

The enantiomeric excess was determined by Mosher ester analysis via integration of the aliphatic CH$_2$O protons.

General Procedure for the Addition of Alkynes to Aldehydes as Shown in Table 7

To a solution of the TADDOL (0.1 mmol) in THF (3 mL) was added diethylzinc (1.0 M in THF, 2.0 mL, 2.0 mmol). After the mixture was stirred for 1 h at rt, phenylacetylene (1.5 mmol) was added and the stirring continued for an additional 1 h. Benzaldehyde (1.0 mmol) was then added, and the reaction mixture was stirred for 18 h at rt. The reaction was then quenched with 1 N HCl and extracted with CH$_2$Cl$_2$. The organic layer was washed with brine, dried (MgSO$_4$), and concentrated in vacuo. Chromatography on silica gel then afforded the desired product.

The enantiomeric excess was determined by HPLC on a Chiralcel OD-H column.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

The invention claimed is:

1. A method of performing an asymmetric catalytic reaction comprising:
   combining a first reactant, a second reactant, and a catalytic amount of a metal-free chiral hydrogen-bond donor in a solvent to form a reaction mixture; and
   reacting the first reactant and the second reactant to form an enantiomeric excess of a reaction product.

2. The method of claim 1 wherein the reaction comprises a [4+2] cycloaddition.

3. The method of claim 1 wherein the reaction mixture is substantially free of metals.

4. The method of claim 2 wherein the first reactant comprises a diene and the second reactant comprises a heterodienophile.

5. The method of claim 4 wherein the heterodienophile comprises a carbonyl group.

6. The method of claim 4 wherein the heterodienophile comprises an aldehyde.

7. The method of claim 4 wherein the heterodienophile comprises a ketone.

8. The method of claim 4 wherein the heterodienophile comprises an α,β-unsaturated carbonyl compound.

9. The method of claim 4 wherein the heterodienophile comprises an α,β-unsaturated aldehyde.

10. The method of claim 1 wherein the chiral hydrogen-bond donor comprises a chiral alcohol.

11. The method of claim 10 wherein the chiral alcohol comprises a 1,3-diol group.

12. The method of claim 10 wherein the chiral alcohol comprises a 1,4-diol group.

13. The method of claim 10 wherein the chiral alcohol comprises a 1,6-diol group.

14. The method of claim 10 wherein the chiral alcohol comprises a TADDOL skeleton.

15. The method of claim 10 wherein the chiral alcohol is selected from the group consisting of TADDOL, 1-Napthyl-TADDOL, 2-Napthyl-TADDOL, TADDOL derivatives, BINOL, BINOL derivatives, tartaric acid dialkyl ester derivatives, and hydrobenzoin derivatives.

16. The method of claim 1 wherein the enantiomeric excess is at least 60%.

17. The method of claim 1 wherein the enantiomeric excess is at least 70%.

18. The method of claim 1 wherein the enantiomeric excess is at least 80%.

19. The method of claim 1 wherein the enantiomeric excess is at least 90%.

20. The method of claim 1 wherein the enantiomeric excess is at least 95%.

21. The method of claim 2 wherein the first reactant comprises an alkyne and the second reactant comprises an aldehyde.

22. The method of claim 21 further comprising adding an organometallic reagent to the reaction mixture.

23. The method of claim 22 wherein the organometallic reagent is diethyl zinc.

24. A reaction mixture comprising:
   a first reactant selected from the group consisting of diene and an alkyne;
   a second reactant selected from the group consisting of a dienophile and an aldehyde, wherein the second reactant is complementary in reactivity to the first reactant;
   a solvent; and
   a catalytic amount of a metal-free chiral hydrogen-bond donor.

25. The reaction mixture of claim 24 wherein the reaction mixture is substantially free of metals.

26. The reaction mixture of claim 24 wherein the first reactant comprises a diene and the second reactant comprises a dienophile.

27. The reaction mixture of claim 26 wherein the dienophile comprises a heterodienophile.

28. The reaction mixture of claim 27 wherein the heterodienophile comprises a carbonyl group.

29. The reaction mixture of claim 27 wherein the heterodienophile comprises an aldehyde.

30. The reaction mixture of claim 27 wherein the heterodienophile comprises an α,β-unsaturated aldehyde.

31. The reaction mixture of claim 24 wherein the first reactant comprises an alkyne and the second reactant comprises an aldehyde.

32. The reaction mixture of claim 31 wherein the reaction mixture further comprises an organometallic reagent.

33. The reaction mixture of claim 32 wherein the organometallic reagent comprises diethylzinc.

34. The reaction mixture of claim 24 wherein the chiral hydrogen-bond donor comprises a chiral alcohol.

35. The reaction mixture of claim 34 wherein the chiral alcohol comprises a 1,3-diol group.

36. The reaction mixture of claim 34 wherein the chiral alcohol comprises a 1,4-diol group.

37. The reaction mixture of claim 34 wherein the chiral alcohol comprises a 1,6-diol group.

38. The reaction mixture of claim 34 wherein the chiral alcohol comprises a TADDOL skeleton.

39. The reaction mixture of claim 34 wherein the chiral alcohol is selected from the group consisting of TADDOL, 1-Napthyl-TADDOL, 2-Napthyl-TADDOL, TADDOL derivatives, BINOL, BINOL derivatives, tartaric acid dialkyl ester derivatives, and hydrobenzoin derivatives.

* * * * *